(12) United States Patent
Anderle et al.

(10) Patent No.: US 8,377,375 B2
(45) Date of Patent: Feb. 19, 2013

(54) METHODS FOR THE INACTIVATION OF MICROORGANISMS IN BIOLOGICAL FLUIDS, FLOW THROUGH REACTORS AND METHODS OF CONTROLLING THE LIGHT SUM DOSE TO EFFECTIVELY INACTIVATE MICROORGANISMS IN BATCH REACTORS

(75) Inventors: Heinz Anderle, Klosterneuburg (AT); Peter Matthiessen, Vienna (AT); Hans-Peter Schwarz, Vienna (AT); Peter Turecek, Klosterneuburg (AT); Thomas Kreil, Klosterneuburg (AT); Daniel R. Boggs, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/100,570

(22) Filed: May 4, 2011

(65) Prior Publication Data

US 2011/0206554 A1    Aug. 25, 2011

Related U.S. Application Data

(62) Division of application No. 10/924,579, filed on Aug. 24, 2004, now Pat. No. 7,993,580.

(51) Int. Cl.
*A61L 2/00* (2006.01)
*G01N 31/16* (2006.01)
*G01N 23/00* (2006.01)
*G01N 11/00* (2006.01)
*A61N 5/00* (2006.01)

(52) U.S. Cl. .......... 422/3; 422/22; 422/24; 422/75; 422/82.05; 250/435; 250/436; 250/437; 250/455.11; 250/492.1; 73/1.02; 73/53.01

(58) Field of Classification Search ........... 422/3, 22, 422/24, 75, 82.05; 250/435, 436, 437, 455.11, 250/492.1; 73/1.02, 53.01
See application file for complete search history.

(56) References Cited

U.S. PATENT DOCUMENTS 2,725,482 A    11/1955   Levinson et al.
(Continued)

FOREIGN PATENT DOCUMENTS

CN    1287496 A    3/2001
DE    1 269 389 B    5/1968
(Continued)

OTHER PUBLICATIONS

Anderle, H. et al., "Assessment of the Efficacy of Virus Inactivation by UV-C Treatment of Therapeutic Proteins," *2nd International Congress on Ultraviolet Technologies*, Vienna, Jul. 9-11, 2003, 5 pages (2003).
(Continued)

*Primary Examiner* — Jill Warden
*Assistant Examiner* — Monzer Chorbaji
(74) *Attorney, Agent, or Firm* — Morgan, Lewis & Bockius LLP

(57) ABSTRACT

The present invention relates to a method for determining an effective dose of monochromatic or polychromatic light from one or more light sources to inactivate microorganisms present in a biological fluid, preferably a non-transparent fluid. Moreover, there is provided a method for the inactivation of microorganism in a biological fluid in a flow-through-reactor. Moreover, the invention advantageously provides a flow-through-reactor with one or more thermostated light sources. The invention further provides a method of controlling the light sum dose of monochromatic or polychromatic light emitted from one or more light sources to effectively inactivate microorganisms present in a biological fluid in a batch reactor.

24 Claims, 14 Drawing Sheets

U.S. PATENT DOCUMENTS

| | | | |
|---|---|---|---|
| 4,481,189 A | | 11/1984 | Prince |
| 4,540,573 A | | 9/1985 | Neurath et al. |
| 4,730,922 A | | 3/1988 | Bach et al. |
| 4,946,648 A | | 8/1990 | Dichtelmüller et al. |
| 5,567,616 A | | 10/1996 | Dill, II |
| 5,661,305 A | | 8/1997 | Lawrence et al. |
| 5,919,907 A | * | 7/1999 | Shanbrom ............... 530/362 |
| 6,540,967 B2 | | 4/2003 | Mausbach et al. |
| 6,576,201 B1 | | 6/2003 | Woo et al. |
| 6,586,172 B1 | * | 7/2003 | Gunn et al. ............... 435/2 |
| 6,596,542 B1 | * | 7/2003 | Schulz ............... 436/1 |
| 6,815,686 B1 | | 11/2004 | Echols et al. |
| 7,297,723 B2 | * | 11/2007 | Wilke et al. ............... 522/6 |
| 2003/0049809 A1 | | 3/2003 | Kaiser et al. |
| 2003/0147770 A1 | | 8/2003 | Brown et al. |
| 2004/0126273 A1 | * | 7/2004 | Forney et al. ............... 422/22 |
| 2006/0045796 A1 | | 3/2006 | Anderle et al. |

FOREIGN PATENT DOCUMENTS

| | | |
|---|---|---|
| EP | 0 607 941 A2 | 7/1994 |
| GB | 0007681.0 | 3/2000 |
| JP | 11-286453 A | 10/1999 |
| WO | WO 94/28210 A1 | 12/1994 |
| WO | WO 97/33629 A1 | 9/1997 |
| WO | WO 00/04930 A2 | 2/2000 |
| WO | WO 00/04930 A3 | 2/2000 |
| WO | WO 00/20045 A1 | 4/2000 |
| WO | WO 00/62025 A1 | 10/2000 |
| WO | WO 01/74407 A1 | 10/2001 |
| WO | WO 02/38191 A2 | 5/2002 |
| WO | WO 02/068917 A2 | 9/2002 |
| WO | WO 03/007998 A1 | 1/2003 |
| WO | WO 2004/075931 A2 | 9/2004 |

OTHER PUBLICATIONS

Asahina et al.; "Effect of Medium Pressure and Low Pressure Ultraviolet Systems on the Inactivation of Selected Bacteriophages"; *Proceedings of the "Disinfection 2002" conference*, Alexandria, VA: Water Environment Federation, (2002).

Battigelli et al., "The Inactivation of Hepatitis a Virus and Other Model Viruses by UV Irradiation"; *Water. Sci. Tech.*, vol. 27, No. 3-4, pp. 339-342 (1993).

Benesi, E., "Design of a Centrifugal Filmer for the Ultraviolet Irradiation of Liquids," *General Motors Engineering Journal*, 3, 7 pages (1956).

Bering et al.; "Methoden zur Messung der Wirksamkeit violetter und ultravioletter Strahlequellen"; *Strahlentherapie*, pp. 189-207 (1912).

Bitton, G. et al., "Effect of Several Clay Minerals and Humic Acid on the Survival of *Klebsiella aerogenes* Exposed to Ultraviolet Irradiation," *Applied Microbiology*, 23:5, pp. 870-874 (1972).

Bolton, J.R., "Ultraviolet Principles and Applications," *EPA Newsletter*, No. 66, pp. 9-36 (1999).

Bolton, J.R. et al., "Standardization of Methods for Fluence (UV Dose) Determination in Bench-Scale UV Experiments," *Journal of Environmental Engineering*, 129:3, pp. 209-215 (2003).

Bowen, E.J., *The Chemical Aspects of Light*, 2nd Revised Edition, Oxford, Clarendon Press, pp. 282-283 (1949).

Brauer, H.D. et al., "A New Reusable Chemical Actinometer for UV Irradiation in the 248-334 nm Range," *Photochemistry and Photobiology*, 37:5, pp. 587-591 (1983).

Brooks, S.C., "The Kinetics of Inactivation of Complement by Light," *The Journal of General Physiology*, 3, pp. 169-183 (1920).

Brummelhuis, H.G.J., "Preparation of the Prothrombin Complex," *Methods of Plasma Protein Fractionation*, edited by J.M. Curling, London: Academic Press, pp. 117-128 (1980).

Cabaj, A. et al., "Measurement of Ultraviolet Radiation with Biological Dosemeters," *Radiation Protection Dosimetry*, 91:1-3, pp. 139-142 (2000).

Caillet-Fauquet, P. et al., "Continuous-Flow UVC Irradiation: A New, Effective, Protein Activity-Preserving System for Inactivation Bacteria and Viruses, Including Erythrovirus B19," *Journal of Virological Methods*, 118, pp. 131-139 (2004).

Calvert, J.G. et al., "Precision Actinometry at Low Light Intensities with Malachite Green Leucocyanide," *Journal of the American Chemical Society*, 74, pp. 2101-2103 (1952).

Cortelyou et al; "Effects of Ultraviolet Irradiation on Large Populations of Certain Water-Borne Bacteria in Motion", *Appl. Environ. Microbiol.*, V. 2, pp. 227-235 (1954).

Cortelyou, J.R. et al., "The Effects of Ultraviolet Irradiation on Large Populations of Certain Water-Borne Bacteria in Motion," *Applied Microbiology*, 2, pp. 269-273 (1954).

Dainton, F.S. et al., "Use of Nitrous Oxide to Discriminate Between Various Forms of Hydrogen Atoms Existing in Aqueous Solutions of Potassium Iodide Irradiated with Ultra-Violet Light," *Nature*, 186, No. 4728, p. 879 (1960).

Della Contrada, J., "Invention Could Revolutionize Decontamination and Purification of Liquids," *University of Buffalo Reporter*, No. 35:27, online edition, 2 pages (2004).

European Search Report, Appln. No. EP 10008758.4-2113, Publ. No. EP1784229, Publ. Date Mar. 2, 2006.

European Search Report, Appln. No. EP 10009727.8-2113, Publ. No. EP2266630 (A1), Publ. Date: Dec. 29, 2010.

Favaro, G., "Actinometry: Concepts and Experiments," *Drugs: Photochemistry and Photostability*, Special Publications of the Royal Society of Chemistry 225, pp. 295-304 (1998).

FDA (Food and Drug Administration, US Department of Health and Human Services), "Kinetics of Microbial Inactivation for Alternative Food Processing Technologies: Ultraviolet Light," *Kinetics of Microbial Inactivation for Alternative Food Processing Technologies*, Washington, DC, 8 pages (2000).

Fisher, G.J. et al., "A Calorimetric Determination of the Quantum Yield for the Ionization of Malachite Green Cyanide by Ultraviolet Radiation," *Photochemistry and Photobiology*, 6, pp. 757-767 (1967).

Forney, L.J. et al., "Optimum Photolysis in Taylor-Couette Flow," *American Institute of Chemical Engineers Journal*, 49, No. 3, pp. 727-733 (2003).

Forney, L.J. et al., "Ultraviolet Disinfection: Similitude in Taylor-Couette and Channel Flow," *Environmental Science and Technology*, vol. 37, No. 21, Nov. 1, 2003, pp. 5015-5020.

Gauglitz, G. et al., "Azobenzene as a Convenient Actinometer: Evaluation Values for UV Mercury Lines and for the $N_2$ Laser Line," *Journal of Photochemistry*, 15, pp. 255-257 (1981).

Gauglitz, G., "Modern Chemical Actinometry," *EPA Newsletter*, pp. 49-53 (1983).

Gauglitz, G. et al., Photokinetische Grundlagen Moderner Chemischer Aktinometer (Photokinetic Bases of Modern Chemical Actinometers), *Zeitschrift fuer Physikalische Chemie, Neue Folge*, 139, pp. 237-246 (1984). (English Abstract).

Gauglitz, G. et al., "Chemical Actinometry in the UV by Azobenzene in Concentrated Solution: A Convenient Method," *Journal of Photochemistry*, 30, pp. 121-125 (1985).

Habel, K. et al., "A Continuous Flow Method of Exposing Antigens to Ultraviolet Radiation," *Journal of Immunology*, 56, pp. 273-279 (1947).

Hackradt, A., "Uber die kolorimetrische Ausdosierung kunstlicher Lichtquellen auf Grund der Zersetzung einer Jodwasserstofflosung", *Strahlentherapie*, V. 12, pp. 843-845 (1922).

Harm, W., "Biological Effects of Ultraviolet Radiation", *IUPAB Biophysics Series*, Cambridge University Press, New York, 57 pages (1980).

Harrington, W.O. et al., "Reduction of the Microbial Population of Apple Cider by Ultraviolet Irradiation," *Food Technology*, 22, No. 1451, pp. 117-120 (1968).

Hatchard et al., "A New Sensitive Chemical Actinometer. II. Potassium Ferrioxalate as a Standard Chemical Actinometer", Proceedings of the Royal Society of London A, pp. 518-536 (1956).

Hiatt, C.W., "Photodynamic Inactivation of Viruses," *Transactions of the New York Academy of Sciences*, 23, pp. 66-78 (1960).

Hosseini et al; "Inactivating Advetitious Viruses While Preserving Biological Activity", *BioPharm. International*, Dec. 2002, pp. 35-40 (2002).

International Search Report for PCT/EP2005/008467 (May 17, 2006).

Jankowski, J.J. et al., "Nitrate and Nitrite Ultraviolet Actinometers," *Photochemistry and Photobiology*, 1999, vol. 70, No. 3, pp. 319-328.

Jankowski et al., "Development and Intercalibration of Ultraviolet Solar Actinometers", *Photochemistry and Photobiology*, vol. 71(4), pp. 431-440 (2000).

Kirk, A.D. et al., "Errors in Ferrioxalate Actinometry," *Analytical Chemistry*, No. 55, pp. 2428-2429 (1983).

Koutchma, T. et al., "Effectiveness of UV Disinfection of Juice," *IUVA News*, 4, No. 5, pp. 21-23 (2002).

Koutchma, T. et al., "Ultraviolet Disinfection of Juice Products in Laminar and Turbulent Flow Reactors," *Innovative Food Science & Emerging Technologies*, 5, No. 2, pp. 179-189 (2004).

Kuhn, H.J. et al., "Chemical Actinometry," *Pure & Applied Chemistry*, 61, No. 2, pp. 187-210 (1989).

Latarjet et al., "Precisions sur L'inactivation des Bacteriophages par les Rayons Ultraviolets", *Annales de l'Institut Pasteur*, V. 71, pp. 336-339 (1945).

Leuker, G.; "Description and Application of Biodosimetry—a Testing Procedure for UV Systems," *Journal of Water SRT—Aqua* 48(4): 154-160, 1999.

Mack, S.D. et al., "Studies in the Cold Sterilization of Liquid Foods Using Mercury Resonance Radiation: II. Apple Juice," *Food Research*, 24, pp. 383-391 (1959).

Mark, G. et al., "The photolysis of potassium peroxodisulphate in aqueous solution in the presence of *tert*-butanol: a simple actinometer for 254 nm radiation." *Journal of Photochemistry and Photobiology A: Chemistry*, Dec. 20, 1990, vol. 55, No. 2, pp. 157-168, Abstract Only, 2 pages.

Moroson, et al., "A Sensitive Chemical Actinometer for Ultra-Violet Radiation," *Nature*, vol. 204 (Nov. 14) pp. 676-678 (1964).

Morowitz, H.J., "Absorption Effects in Volume Irradiation of Microorganisms," *Science*, 111, pp. 229-230 (1950).

Murray et al., "Effect of Ultraviolet Radiation on the Infectivity of Icterogenic Plasma", *Journal of the American Medical Association*, vol. 157 (1), pp. 8-14, (1955).

Oppenheimer, F. et al., "The Ultraviolet Irradiation of Biological Fluids in Thin-Flowing Films," *American Journal of Public Health*, 49, No. 7, pp. 903-923 (1959).

Qualls, R.G. et al., "Bioassay and Dose Measurement in UV Disinfection," *Applied and Environmental Microbiology*, 45, No. 3, pp. 872-877 (1983).

Rahn, R.O., "Use of Potassium Iodide as a Chemical Actinometer," *Photochemistry and Photobiology*, vol. 58:6, pp. 874-880 (1993).

Rahn, R.O., "Potassium Iodide as a Chemical Actinometer for 254 nm Radiation: Use of Iodate as Electron Scavenger," *Photochemistry and Photobiology*, 66:4, pp. 450-455 (1997).

Rahn, R.O. et al., "Dosimetry of Room-Air Germicidal (254 nm) Radiation Using Spherical Actinometry," *Photochemistry and Photobiology*, vol. 70(3), pp. 314-318 (1999).

Rahn, R.O. et al., "Quantum Yield of the Iodide-Iodate Chemical Actinometer: Dependence on Wavelength and Concentration," *Photochemistry and Photobiology*, vol. 78(2), pp. 146-152 (2003).

Rideal, E.K. et al., "The Photochemistry of Native Proteins," *Proceedings of the Royal Society Series*, A 205, pp. 391-408 (1951).

Rivers et al., "Ultra-Violet Light and Vaccine Virus. II. The Effect of Monochromatic Ultra-Violet Light upon Vaccine Virus." Journal of Experimental Medicine, vol. 47, pp. 45-49, (1928).

Schenck et al., "Structure of Polyvinylpyrrolidone-Iodine (Povidone-Iodine)", *Journal of Pharmaceutical Sciences*, vol. 68 (12), pp. 1505-1509 (1979).

Schulz, C.R. et al., "Development of a Flow-Through Chemical Actinometer System for Measuring Irradiance in UV Reactors," *Conference Proceedings (on CD-ROM) of the International Ultraviolet Association's 1st International Congress on Ultraviolet Technologies*, Washington DC, Jun. 15-16, 2001, 1 page (2001).

Sczechowski, J.G. et al., "A Taylor Vortex Reactor for Heterogenous Photocatalysis," *Chemical Engineering Science*, vol. 50:20, pp. 3163-3173 (1995).

Somer et al., "Inactivation of Bacteriophages in Water by Means of Non-Ionizing (Uv-253.7nm) and Ionizing (Gamma) Radiation: A Comparative Approach," *Wat. Res.* vol. 35(13), pp. 3109-3116 (2001).

Taylor, A.R., "Effects of Nonionizing Radiations on Animal Viruses," *Annals of the New York Academy of Sciences*, 83, pp. 670-683 (1960).

Wang, J. et al., "Virus Inactivation and Protein Recovery in a Novel Ultraviolet-C Reactor," *Vox Sanguinis*, 86, pp. 230-238 (2004).

Wright, H.B. et al., "UV Dose Required to Achieve Incremental Log Inactivation of Bacteria Viruses, and Protozoa," *Trojan Technologies Inc.*, London, Ontario, Canada, 5 pages (2001).

Yarus et al., "Ultraviolet Sensitivity of the Biological Activity of φX174 Virus, Single-Stranded DNA, and RF DNA", *Biophysical Journal*, vol. 7 (3), pp. 267-278 (1967).

\* cited by examiner

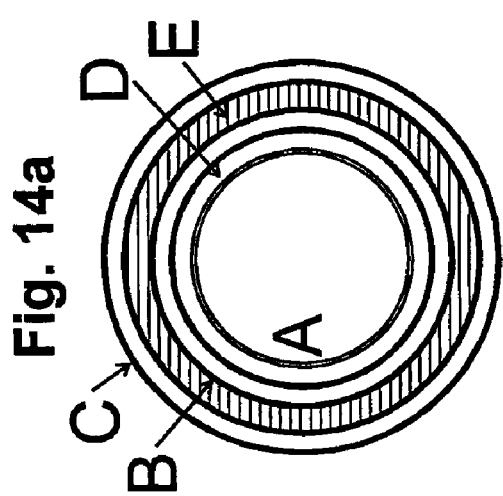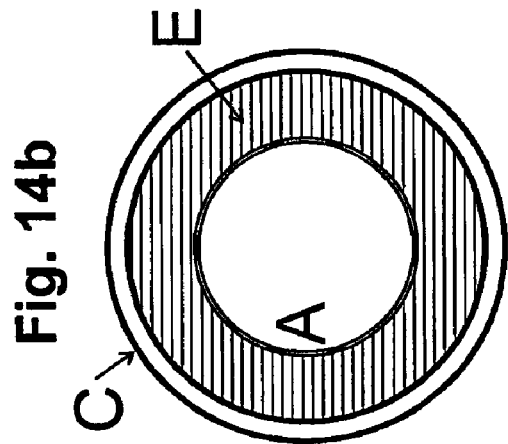

ion, or impose a transversal mixing on the longitudinally flowing fluid to effect an even illumination by transporting all volume fractions to the shallow illuminated outer liquid layer.

Caillet-Fauquet et al. (2004) describe a flow through UV-C irradiation method for inactivating bacteria and viruses using encephalomyocarditis virus spiked samples for biodosimetry or an by the Dean vortices superimposing on the fluid flow. Such a helical envelope-reactor is described in the US Patent application 2003/0049809 A1. The dose received by the solution pumped through the reactor was calculated from the lamp intensity measurement by ferrioxalate actinometry, the absorbance, and the residence time (Wang et al. 2004).

There have been several attempts in the past to determine the energy of light effective during the irradiation. Light energy can be measured either by a photosensitive electronic sensor, or by a photochemical reaction effected by the light photons, or by its inactivation of an indicator microorganism present in or added to the biological fluid itself. Other theoretical methods comprise mathematical modeling simply by multiplying the residence time of a volume element with the intensity to calculate the dose, or in a more refined approach, by flow modeling to resolve residence time and dose.

Chemical actinometry measures the effect of light on a photochemical reactant mixture (Kuhn et al. 1989; Favaro 1998). In general, established photochemical actinometers with known quantum yield and temperature dependence can surpass electronic devices in reproducibility and stability. Photochemical reaction products should be measured on-line most conveniently e.g. by spectrophotometry or chemical sensors (Gauglitz 1983).

A preferred approach employs total opacity of the actinometric solution at the measured wavelength, so that the photochemical reaction occurs only at the very surface (Kuhn et al. 1989; Favaro 1998). Therefore sufficiently high reactant concentrations are preferred.

In a vaccine flow-through UV reactor for the inactivation of influenza viruses, the uridine actinometer was used to measure the lamp intensity (Zheleznova 1979).

Taylor-vortex generating devices have also been investigated as photochemical reactors for heterogeneous and homogeneous photochemical processes (Sczechowski et al. 1995, Forney and Pierson 2003). For the actinometric examination of the reactor, either the ferroixalate or the iodide/iodate actinometer was used. However, an absorbance-matching calibration to determine the dose effective in the iodide solution was neither done nor proposed (Forney and Pierson 2003).

For UVC measurement, the classical actinometers are uranyl oxalate (Bowen 1949, Kuhn et al. 1989) and the ferrioxalate actinometer, but use of the first is limited by the Uranium radiotoxicity, and of the latter by UV-B, UV-A, and visible light sensitivity (Kirk and Namasivayam, 1983). Hydrogen sulfite or hydrogen cyanide adducts of triphenylmethane dyes also are as well known as UV-C-sensitive actinometers. For example, the colorless malachite green leucocyanide dissolved in ethanol does not show a long-wave UV or visible light sensitivity, but the green photo product absorbs additionally in the UV-C range (Calvert and Rechen 1952, Fisher et al. 1967). Azobenzene (Actinochrome 2R 245/440) in methanol enables a reuse of the actinometric solution (Gauglitz and Hubig 1981, 1984, 1985) as well as heterocoerdianthrone endoperoxide (Actinochrome 1R 248/334) (Brauer and Schmidt 1983). Despite the elegance of these complex organic compounds dissolved in organic solvents, it has been postulated that actinometric substances and solutions should be non-toxic and non-hazardous.

Immediately after various ultraviolet lamps became available in the beginning of the $20^{th}$ century, acidic iodide solutions have been used as chemical actinometers (Bering and Meyer 1912). The low quantum yield of 0.05 lead to the use of nitrous oxide ($N_2O$) as an electron scavenger (Dainton and Sills 1960, Rahn 1993). A more recent approach of opaque UV-C actinometry is the iodate-stabilized photodecomposition of iodide (Rahn 1997, Rahn et al. 1999, 2003). The triodide formed from iodide photolysis at 253.7 nm is determined spectrophotometrically at 352 nm or higher wavelengths (375 nm, 400 nm). This system has the advantage of insensitivity to wavelengths over 300 nm.

The use of an actinometer solution has been proposed to replace UV-sensors by flow-through or static probes containing the actinometer solution, which are inserted into the irradiation reactor. The concentrated actinometer solution, e.g. the iodide/iodate actinometer according to U.S. Pat. No. 6,596,542 or an uridine solution (Schulz et al. 2001) is pumped through a UV-transparent tube receiving the UV light from the lamp, or contained in a cell with a transparent window facing the UV lamp to be exposed for a defined time, and the photo products are then measured in a spectrophotometer. These sensors, however, measure only the fraction of radiation incident on them, but not the average fluence (light dose) effective on the fluid to be irradiated while contained within the irradiation reactor.

The use of a water-soluble triphenyl methane dye (4,4',4"-tris-di-β-hydroxyethylaminotriphenyl acetonitrile) as an added actinometer substance is described for the "cold-sterilization" of microorganisms in fruit ciders, juices and plant saps by flow-through UV-C irradiation (Koutchma and Adhikari 2002). Equipment for this process is commercially available, e.g. the "CiderSure" or the "Sap Steady" thin-film irradiators manufactured by FPE Inc. of Macedon, N.Y., or the "Light Processed System" coiled tube irradiator manufactured by Salcor Inc., Fallbrook, Calif. Ciders and juices obtained from squeezed fruits show high turbidity from suspended particles, and high UV-C absorption from dissolved phenolic compounds and from ascorbic acid, and also a viscosity similar to protein solutions. Clarified apple juice has an absorption coefficient of 9/cm at 253.7 nm. The actinometer substance is added to the highly absorbing juice and irradiated in a collimated-beam apparatus, as used for the absolute UV inactivation kinetics determination of microorganisms in non-absorbing suspension (Bolton and Linden 2003). The absorption of the actinometer photoproduct at 600 nm increases, but in fact the added actinometer substance will only receive the light quanta fraction corresponding to its absorbance fraction of the total absorbance. The effective dose is then calculated from the destruction of the added actinometer dye. As it can be deduced from an "absorbed dose" of 190 mJ/cm$^2$ inactivating no more than 3 $\log_{10}$ colony-forming units (cfu) *E. coli* K12/mL in apple juice in a petri dish, the addition of an actinometer substance to the sample itself delivers obviously false results for the effective dose. In non-absorbing suspension, 5 $\log_{10}$ cfu/mL *E. coli* are inactivated at ~10 mJ/cm$^2$ (Wright and Sakamoto 1999). However, the dose effective in the solution must be the same as the dose effective on the microorganism. The proposed addition of an actinometer substance to an already absorbing medium is therefore not capable to accomplish an exact effective dose measurement.

The biological dosimetry using a photoinactivatable microorganism was the first method to determine the applied dose in the irradiation of plasma, although details on the dosimetry using *Aerobacter aerogenes* (outdated name for *Klebsiella pneumoniae*) were not given. In addition, single-stranded DNA bacteriophages of the microviridae family such as S13 and Phi-X (phi chi) 174 give a linear decrease of titer with an increasing UV irradiation dose. Biodosimetry based on the inactivation of bacteriophages (e.g. Phi-X 174 or the single-stranded RNA bacteriophage MS2), or the inactivation of *Bacillus subtilis* spores, has been developed for testing flow-through ultraviolet water disinfectors. The dose-dependent un-attenuated inactivation rate of the bacteriophage Phi-X 174 in a dilute and UV-C transparent buffer suspension agitated horizontally in 33 mm petri dishes in the homogeneous radiation field of a 9 W UV-C lamp at an irradiance of 0.225 mW/cm2 was determined to be −0.44 ($\log_{10}$ pfu/mL)/(mJ/cm$^2$) (Anderle et al. 2004).

The commercial thin-layer irradiator "CiderSure" (manufactured by FPE Inc., Rochester, N.Y.) used for fruit juices, essentially consists of an outer stainless-steel tube and an inner quartz tube, both in concentric and parallel mount to the centered tubular UV light source, where the fluid flows longitudinally through the annular gap in-between. It is validated by biodosimetry for every type of fruit juice and cider to adjust the flow-rate required for a >5 $\log_{10}$ colony forming units/mL reduction of $E.\ coli$ O157:H7. Additionally, the light intensity loss over time is compensated by flow rate correction because the dose H is usually assumed as intensity Exresidence time t (FDA 2000). However, this biodosimetric validation alone would not enable an optimization of the flow-through-reactor to achieve a narrow residence-time distribution thus avoiding excessive over-irradiation of the fluid. Even with nutritional fluids, this should be avoided, because UV over-dosage can generate an undesired off-flavor rendering the product unpalatable.

With all the aforementioned flow-through-devices, there are however rheological and technical limitations to overcome. Every volume element entering the irradiation zone is longitudinally dispersed into a faster flowing fraction, which receives a lower dose through its shorter residence time, and a slower tailing fraction, which receives a higher dose, and the volume fractions in between. FIG. 7 in U.S. Pat. No. 6,576,201 gives an example of a residence-time distribution dependent on the rotation rate of the inner cylinder in the Taylor vortex-generating cell. A dose too low can incompletely destroy the viable microorganisms and effect an incomplete inactivation. A dose too high can destroy the substances of interests, such as vitamins and flavors in juices, proteins in blood derivatives, or antigens in vaccines. Therefore it is desirable to optimize the irradiation process to make it sufficiently effective to destroy all target microorganisms and safe to preserve all substances of interest. A method to optimize such a process is therefore particularly desirable.

Another technical limitation of the aforementioned flow-through and batch reactor devices is the aging of the light sources used, which can lose a fraction of their initial light output during their operating lifetime. To compensate for that effect, an integrating counter has been used to ensure a constant and reproducible light dosage, however irrespective of the absorbance of the solution to be irradiated (Rideal and Roberts 1951). Moreover, the inactivation may be discontinued during operation due to a malfunctioning of a least one of the light sources. Although this decay and/or the switching off is detectable with an electronic light-sensitive sensor alone, the determination of its effect on the light dose effective on the fluid to be treated would require a measurement of such a dose to establish the relation between lamp intensity, absorbance, and dose decay, and to compensate such a decay by changing other process variables such as the flow rate. These devices also require re-validation at certain time intervals to ensure a consistent and effective operation. A method for measuring, controlling and compensating such fluctuations in light irradiation during light inactivation of microorganisms in a biological fluid, preferably in relationship to the absorbance of the biological fluid to be irradiated a batch reactor, and also a method for controlling that the inactivation process is carried out effectively despite fluctuations of the light irradiation are therefore particularly desirable.

Moreover, the light sources develop a considerable amount of thermal energy during operation of the irradiation devices such as batch-reactors and flow-through-reactors. The heating of the lamps in turn leads to considerable fluctuations of the light emission. In the low-pressure Hg vapor lamp, for example, the major part of the lamp power is converted into heat, and only around a third into light emission. Although low-pressure Hg vapor lamps seldom overheat beyond 60° C., temperature-sensitive substances of interest can suffer damage even by moderate heat. Direct cooling of only the flow conduit in the photoinactivation reactor will not thermostat the lamp and stabilize the intensity, and an adjustment of the lamp voltage to stabilize the intensity would not remove the heat, or the excessive heat. Accordingly, it would also be particularly desirable to develop flow-through-reactors which would be able to decrease the fluctuations of light irradiation caused by the heating of the light sources and which would preferably be able to keep the temperature of the lamp essentially constant or at least less fluctuating. Such a thermostatization has only been attempted with the 6-lamp centrifugal film irradiator as disclosed in U.S. Pat. No. 2,725,482 (Benesi 1956) where a water-cooled heatpipe for every lamp removed the excess heat. Other flow-through irradiators such as the Dill irradiator (U.S. Pat. No. 5,567,616), the baffled or other motionless mixer-elements containing tube type irradiator (U.S. Pat. No. 6,586,172), or the helical tube-type irradiator (WO 02/38191) have obviously been intended and disclosed only without a direct lamp thermostatization. In U.S. Pat. No. 6,586,172 assisted air-flow cooling (ventilation) is envisaged, which is however less effective than direct liquid thermostatization. The effectiveness depends on the ambient air temperature. In free-flowing thin-film irradiators the stream of coolant air may evaporate the water in the biological fluid. Liquid lamp thermostatization may ensure immediate operation at the maximum pathogenicidal intensity without burn-in time, as e.g. for low-pressure Hg vapor lamps with the maximum UV-C (253.7 nm) yield at 41.5° C., or may filter out infrared radiation, as e.g. from incandescent light sources, which would otherwise be absorbed and converted to excessive heat by the biological fluid.

In 1960, one of the leading experts in thin-film UV-C-irradiated vaccine technology stated: "In order to calculate the absolute quantity of energy involved in the virus inactivation itself, there must be some manner of quantitating the relative amounts of ultraviolet energy absorbed by the virus and the culture medium. This has not been possible as yet; furthermore the absolute exposure is dependent upon a number of variable factors: viscosity, temperature, surface tension, and frictional resistance of flow" (Taylor 1960). While such protein solutions or virus suspensions are usually clear or very slightly opalescent colloids, other fluids may constitute suspensions of filterable solids in a liquid. An investigation of the effect of various clay minerals on the inactivation of $Klebsiella\ aerogenes$ bacteria in water has demonstrated a protection of the bacteria by UV-absorbing clays, but no such effect by UV-scattering clays (Bitton 1972). As recently shown for turbid apple cider and clear apple juice, the turbidity of such suspensions has the effect that at a similar apparent absorbance as measured in a spectrophotometer, microorganisms are inactivated faster in the turbid than in the clear fluid (Koutchma et al. 2004). The absolute exposure apparently depends also on the fraction of light scattered by the particles into the solution. Up until now no determination of the photochemically effective dose on microorganisms in a fluid sample has been reported in scientific or patent literature.

Accordingly, a method for the determining the effective dose for inactivating microorganisms contained in a biological fluid, in particular a non-transparent biological fluid, preferably a method carried out in a flow through-reactor is desirable. Moreover, it is an object to provide a method for effectively inactivating microorganisms contained in a biological fluid, in particular a non-transparent biological fluid, preferably while leaving biologically active substances of interest unaffected.

SUMMARY OF THE INVENTION

The solution to the above technical problems is achieved by the embodiments characterized in the claims and in particular, by providing in a first aspect of the invention a method for determining an effective dose of monochromatic or polychromatic light from one or more light sources to inactivate microorganisms present in a biological fluid, comprising measuring the effect of the monochromatic or polychromatic light on a dosimetric solution, wherein the inactivation is carried out in a flow-through-reactor.

According to another aspect there is provided a method for the inactivation of microorganism in a biological fluid in a flow-through-reactor, comprising irradiating the biological fluid with an effective dose of monochromatic or polychromatic light from one or more light sources, wherein the effective dose is determined according to the method described in the preceding section and in detail below.

According to another aspect there is provided a method for determining an effective dose of monochromatic or polychromatic light from one or more light sources to inactivate microorganisms present in a non-transparent biological fluid, comprising measuring the effect of the monochromatic or polychromatic light on a dosimetric solution matching the turbidity of the biological fluid at the photoinactivating wavelengths used, the turbidity and absorbance of the biological fluid, the turbidity and the viscosity of the biological fluid, the turbidity and the absorbance and the viscosity of the biological fluid, the absorbance of the biological fluid, or the viscosity and absorbance of the biological fluid, based on a light dose calibration by i) irradiating the dosimetric solution in a layer of an optical path-length sufficiently thin to absorb only a fraction of the incident light at a predetermined defined irradiance for a defined time to apply a defined fluence (light dose) resulting in a change of a measurable physical or chemical magnitude, and ii) by reading out the dose corresponding to the change in the magnitude measured during or after the light irradiation of the dosimetric solution in the light irradiation reactor, wherein step i) is executed before step ii) or vice versa.

According to another aspect there is provided a method for the inactivation of microorganism in a non-transparent biological fluid, comprising irradiating the biological fluid with an effective dose of monochromatic or polychromatic light from one or more light sources, wherein the effective dose is determined according to the method described in the preceding section and in detail below.

According to still another aspect there is provided a UV-photoinactivation flow-through-reactor, in which one or more light sources are encased by an envelope thermostat, through which envelope thermostat a thermostated and essentially light-transparent liquid is flowing to remove heat from the lamp, thereby ensuring an essentially constant lamp intensity.

Moreover, it is further provided a method of controlling the light sum dose of monochromatic or polychromatic light emitted from one or more light sources to effectively inactivate microorganisms present in a biological fluid in a batch reactor, comprising the steps of:

a) determining the absorption-dependent irradiation source target light sum dose based on the effective dose of monochromatic or polychromatic light to inactivate microorganisms present in the biological fluid, the irradiation light dose rate and the irradiation time necessary to effectively inactivate the microorganisms in the batch reactor;

b) recording the irradiation light dose rate and the irradiation time during inactivation of the microorganisms present in the biological fluid in the batch reactor;

c) calculating the absorption-dependent irradiation source light sum dose based on the measurements in step b);

d) comparing the absorption-dependent irradiation source light sum dose determined in step c) with the absorption-dependent irradiation source target light sum dose determined in step a); and e) discontinuing light exposure of the biological fluid once the absorption-dependent irradiation source light sum dose is equal to or greater than the absorption-dependent irradiation source target light sum dose.

Other objects, features and advantages of the present invention will become apparent from the following detailed description. It should be understood, however, that the detailed description and the specific examples, while indicating preferred embodiments of the invention, are given by way of illustration only. Various changes and modifications within the spirit and scope of the invention will also become apparent to those skilled in the art from this detailed description.

BRIEF DESCRIPTION OF THE DRAWINGS

The accompanying drawings, which are incorporated in and constitute a part of the specification, illustrate one embodiment of the invention, and, together with the general description given above and the detailed description of this embodiment given below, serve to explain the principles of the invention. Thus, for a more complete understanding of the present invention, the objects and advantages thereof, reference is now made to the following descriptions taken in connection with the accompanying drawings in which:

FIG. 14 depicts a cross-sectional view of tubular lamp thermostatization arrangements (FIGS. 14a and 14b) for use with a thermostating liquid.

DETAILED DESCRIPTION OF THE INVENTION

Figure 1:
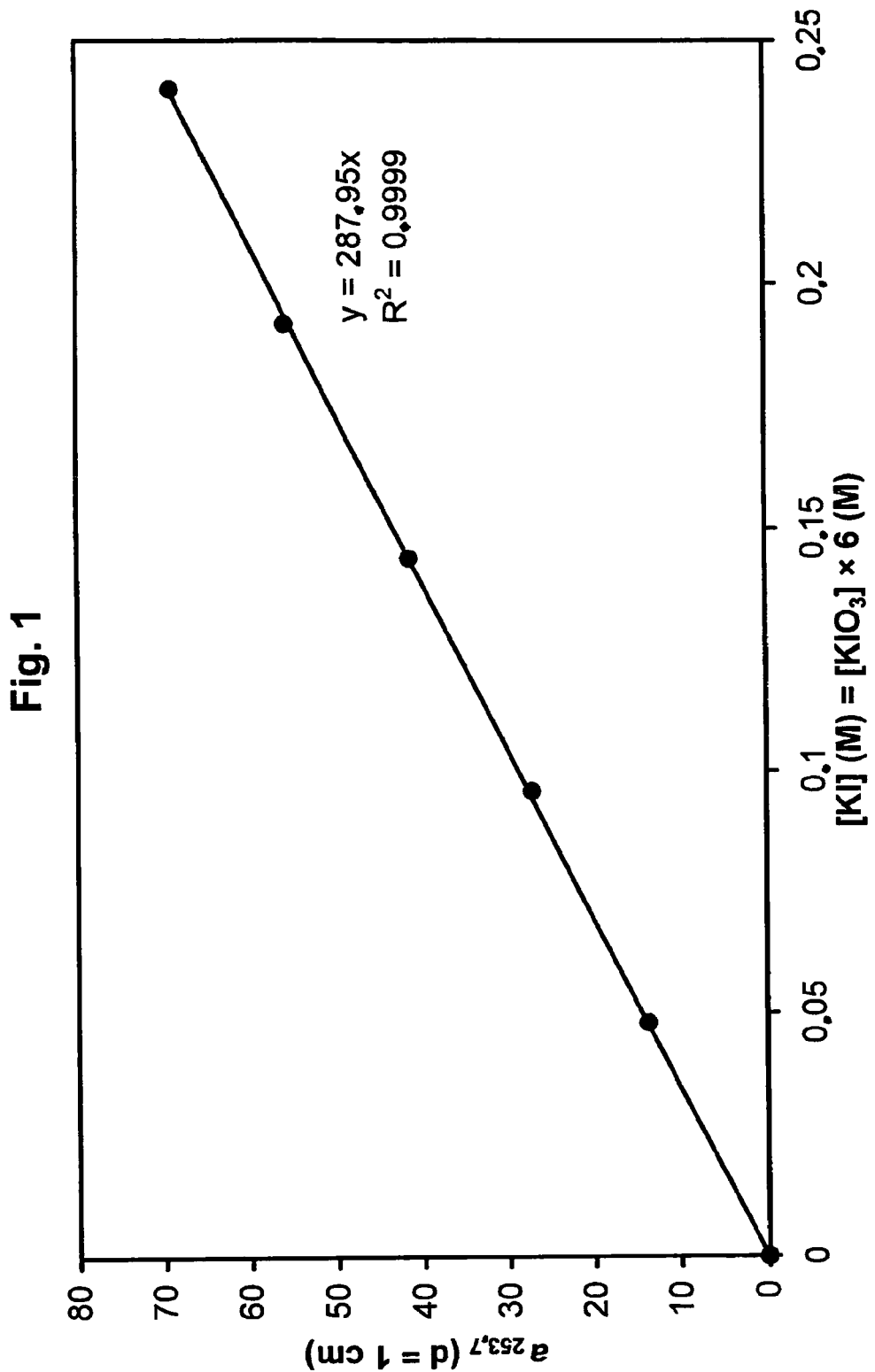
FIG. 1 depicts the linear relation between an absorption coefficient and the iodide/iodate concentration (cf. Example 1).

In a first aspect the invention provides a method for determining an effective dose of monochromatic or polychromatic light from one or more light sources to inactivate microorganisms present in a biological fluid, comprising measuring the effect of the monochromatic or polychromatic light on a dosimetric solution, wherein the inactivation is carried out in a flow-through-reactor. Preferably, the effect of light on the dosimetric solution is determined by a method comprising measuring the effect of the monochromatic or polychromatic light on a dosimetric solution matching the absorbance of the biological fluid at the photoinactivating wavelengths used, or the absorbance and the viscosity of the biological fluid, based on a light dose calibration by i) irradiating the dosimetric solution in a layer of an optical path-length sufficiently thin to absorb only a fraction of the incident light at a predetermined defined irradiance for a defined time to apply a defined fluence (light dose) resulting in a change of a measurable physical or chemical magnitude, and ii) by reading out the dose corresponding to the change in the magnitude measured during or after the light irradiation of the dosimetric solution in the light irradiation reactor, wherein step i) is executed before step ii) or vice versa. Preferred embodiments are provided in Examples 1, 2, and 17.

A microorganism refers to any microorganisms selected from species of the monera kingdom, spores of the species of the monera kingdom, non-pathogenic or microorganisms species of the fungi kingdom, spores of the species of the fungi kingdom, archaea, prokaryotes, preferably bacteria, eukaryotes, viruses to ensure that such or similar microorganisms are killed or reduced in activity, and bacteriophages. Preferably the viruses are selected from Parvoviridae viruses, Minute Murine Virus (MMV), Canine Parvovirus (CPV), Bovine Parvovirus (BPV), Porcine Parvovirus (PPV), Feline Parvovirus (FPV)), Circoviridae viruses, Circinoviridae viruses, Picornaviridae viruses, preferable Hepatitis A Virus (HAV) and Encephalomyocarditis Virus (EMV), Anelloviridae viruses, Encephalomyocarditis Virus (EMV)), Enteroviridae RNA viruses, Microviridae DNA bacteriophages, and Leviviridae RNA bacteriophages. Preferred microorganisms are lipid-enveloped single-stranded or double-stranded, lipid enveloped or non-enveloped viruses.

A biological fluid refers to any natural or artificial biological fluid, such biological fluids comprising milk, whey and milk protein fractions, and the whole fluid and fractions of blood, blood products, plasma, plasma fractions, serum, fluids derived from blood, fluids derived from plasma, fluids derived from serum, fluids containing protein fractions, spinal and cerebral fluid, lymph, saliva, semen, urine, prokaryotic cell culture supernatant, eukaryotic cell culture supernatant, prokaryotic cell lysate, eukaryotic cell lysate, or liquid derivatives of such aforementioned fluids.

A particularly preferred biological fluid according to the invention is a therapeutic fluid which refers to any fluid intended for external, enteral or parenteral therapeutical use, which essentially is not transparent at the photoinactivating wavelength and sensitive to excessive dosage of photoinactivating radiant energy. These fluids include blood, blood products, plasma, plasma fractions, serum and fluids derived from blood, plasma and serum. Transparent and clear fluids such as water, physiological saline, Ringer's lactate, or glucose solution will tolerate over-irradiation and do not always require an exact light dosage.

Another particularly preferred biological fluid according to the invention is a cosmetic fluid which refers to any fluid intended for external use, which essentially is not transparent, i.e. absorbing or turbid, or absorbing and turbid, at the photoinactivating wavelength and sensitive to excessive dosage of photoinactivating radiant energy. Transparent and clear fluids, such as alcohol-water fragrance, may tolerate over-irradiation and do not always require an exact light dosage.

A further particularly preferred biological fluid according to the invention is a nutritional fluid which refers to any fluid intended for oral or nasal intake, preferably for nutritional or thirst-quenching or refreshment use, which essentially is not transparent, i.e.

absorbing or turbid, or absorbing and turbid, at the photoinactivating wavelength and sensitive to excessive dosage of photoinactivating radiant energy and includes milk, whey, milk products, products derived from milk, fruit juices, products derived from fruit, vegetable juices, products derived from vegetable, native plant sap, transgenic plant sap, synthetic beverages, processed beverages, fermented beverages, and alcoholic beverages. Transparent fluids such as tap water, bottled mineral water, or lemonade made from citric acid, carbon dioxide, and sugar dissolved in water will generally tolerate over-irradiation and do not always require an exact light dosage.

Another particularly preferred biological fluid according to the invention is a diagnostic fluid or a fluid derived there from, i.e. liquid diagnostics and diagnostic kits such as antibody solutions or liquids containing components thereof. Transparent diagnostic fluids, such as distilled water, an inorganic salt buffer, or pro-coagulant calcium chloride solution, may tolerate over-irradiation and do not always require an exact light dosage.

The biological fluid according to the invention preferably is a biological fluid which attenuates the pathogenicidal light to an extent that the light intensity is readily attenuated along the optical path length in the pathogen photoinactivation reactor. This attenuation may either be caused by molecular chromophores contained in the biological fluid, such as amino acids, proteins, nucleotides, nucleic acids, or dyes, or of molecular chromophores of added substances, such as photosensitizers or photoprotectants, or by turbidity from light-scattering and absorbing macromolecules and suspended particles, or by a combination of all these contributing parameters. This attenuation depends on the optical path length. A fluid with a decadic absorption coefficient of 1/cm will absorb only 5.5% of the incident light in an shallow 0.5 mm liquid layer, and will therefore behave as essentially transparent, but will absorb 95.7% of the incident light in a 10 cm deep liquid layer. Preferably, any biological fluid that attenuates more than about 5%, preferably more than about 10%, even more preferably more than about 20% of the incident light along the reactor optical path length requires chemical dosimetry to determine the effective dose according to the invention. According to the exponential light attenuation, the initial intensity has become extinct to $1/1024$ after the 10-fold half-optical path length d½, which reduces the initial intensity to 50%. Preferably, the biological fluids used for UV pathogen inactivation are highly opaque to UV light at about 253.7 nm such as serum-free cell culture supernatant for vaccines (a253.7=5/cm, d½=0.06 cm), prothrombin complex eluate (Brummelhuis 1980) (a253.7=7.5/cm, d½=0.04 cm), fruit juices such as apple juice (a253.7=10/cm, d½=0.03 cm), or plasma (a253.7=25/cm, d½=0.012 cm). This means that after about 6 mm, preferably about 4 mm, more preferably about 3 mm, more preferably about 1.2 mm, the incident UV light energy has essentially been consumed completely, making these biological fluids very opaque.

Biological fluids may contain natural or artificially added substances, which do not cause or inhibit nucleic acid photodamage to microorganisms, but exert a beneficial protecting effect to preserve the components of interest upon light irradiation, and most notably upon UV-light irradiation, by acting as reactive oxygen radical quenchers, e.g. flavonoids such as rutin (Erdmann 1956, WO94/28210), vitamins such as ascorbic acid (Erdmann 1956), and creatinine (JP 11286453-A). However, if these additives supplement an additional absorbance at the wavelength used, too little pathogenicidal light energy might actually reach the microorganisms, if the additional absorbance is not compensated in the applied light dose. An excess of applied energy readily damages the proteins. Therefore the UV or visible light dose required for sufficient microorganism inactivation has not to be exceeded and must be calculated as accurately as possible, as detailed in Examples 1, 2, 11, 12, and 15 to 17.

Light, monochromatic light, or polychromatic light refers to energy in the electromagnetic spectrum, preferably those wavelengths and frequencies within the UV and visible range.

The photochemical methods to inactivate such microorganisms used according to the invention comprise the irradiation with
- short-wave ultraviolet light in the UV-C region between about 200 and about 280 nm, preferably of a germicidal wavelength close to the maximum sensitivity of the nucleic acids at about 265 nm,
- medium-wave ultraviolet light in the UVB region between about 280 and about 320 nm,
- long-wave ultraviolet light in the UV-A region between about 320 and about 400 nm or visible light between about 400 and about 700 nm in the presence of at least one natural or added photosensitizer, or
- pulsed monochromatic coherent or incoherent light, or pulsed broad-spectrum light in the aforementioned wavelength regions. Preferably, the light is emitted continuously.

According to a preferred embodiment of the method for determining an effective dose of light to inactivate microorganisms present in a biological fluid, about 100%, preferably about 80%, preferably about 60%, preferably about 50%, preferably about 30%, or less of the incident irradiance is absorbed along the optical path length.

The amount of light absorbed by such a biological fluid is expressed by the transmission or the absorbance at a defined wavelength 1 and optical path length d, usually 1 cm. From the transmission T, which cannot exceed 100%, the decadic absorbance A is calculated by $A=-\log_{10} T$, and for d=1 cm, A becomes the decadic absorption coefficient al in units of 1/cm. In the most germicidal short-wave ultraviolet around 265 nm, the absorption can reduce the maximum light penetration depth to less than 1 mm.

The light sources used for the methods and reactors according to the invention are usually tubular, based on a metal-vapor discharge lamp. Low-pressure metal vapor lamps, which generate only a modest amount of heat, are preferable for biological fluids, which can be sensitive to heat, especially excess heat. The emission from such a lamp is preferably monochromatic, as from the low-pressure sodium-vapor lamp with its orange light at 589 nm, or the low-pressure mercury vapor lamp with its UVC light at 253.7 nm. The latter can also be coated inside with a phosphor to obtain e.g. a fluorescent white, actinic blue+UVA, blacklight UV-A, or UV-B broadband or narrow-band emission spectrum. Other pathogenicidal light sources suitable for the invention comprise medium and high pressure metal vapor lamps, flash discharge tubes, water-submersed arcs, lasers, excimer lamps, light-emitting diodes, incandescent lamps, and the like.

The total absorbance of such a biological fluid as measured in a spectrophotometer may be composed of the molecular absorbance by the molecular chromophores and in the case of hazy, cloudy or turbid fluids additionally of the turbidity, i.e. the light scattering and attenuation by colloidally dispersed macromolecules and suspended particles. For suspensions of particles (e.g. cellular debris) in absorbing solutions such as unfiltered and turbid fruit ciders, the turbidity can be measured by subtracting the absorbance of the clarification-filtered cider from the absorbance of the unfiltered cider (cf. Example 10).

Photosensitizers are substances which either react directly with the microorganisms, such as psoralen and its derivatives, or which generate a reactive molecule from another component present in the solution, such as singlet oxygen from dissolved oxygen, or a solvated electron from the solvent. The latter class of photo sensitizers comprises phenothiazine dyes, acridines, flavins, porphyrins, and phtalocyanines.

The sensitivity of the microorganism towards light depends on its genome size, its nucleic acid type, and its ability to repair the inflicted photodamage. In general, spores of molds and bacteria as well as eukaryotic cells are most resistant, viruses are less resistant, and vegetative bacteria are most sensitive. The fluence required to reduce the microorganism viability to about the desired orders of magnitude is therefore different for different microorganisms. The fluence is the energy incident onto an area, e.g. a cross-sectional area of the microorganism, which absorbs and uses only a fraction of this energy during exposure (Bolton 1999). The term light dose is also commonly used as an alternative for fluence.

If a microorganism is irradiated in a non-absorbing suspension at a known fluence rate (light power per area) for a defined time, the light dose applied on the microorganism can be calculated, and the dose-dependent inactivation rate can be determined (Bolton and Linden 2003). The inactivation rate constants have thus been determined for many microorganisms, some of which are used as indicator microorganisms to indicate the efficacy of a photochemical treatment process.

The biological fluid can however contain concomitant substances, which can absorb, or particles, which can scatter the pathogenicidally effective light, such as proteins, vitamins and phenolic compounds, or fat liposomes and cell debris. Most of the incident light is consumed by these concomitant substances or shielded by the particles, and only a fraction of the light actually reaches and becomes effective on the target microorganism. Therefore the irradiation time necessary to inactivate such a microorganism in such a biological fluid to the desired order of magnitude exceeds the time to achieve the same inactivation in a non-absorbing aqueous suspension of that microorganism and can be taken into account using the methods according to the present invention.

A wide variety of natural screening compounds protect organisms from the deleterious effects of intense high-energy light. These might however act not only by the capturing and quenching of light-generated radicals or excited molecules, but also by simple absorption of the photobiologically active light spectrum. The addition of such presumably protective additives, e.g. of reactive oxygen species quenchers such as flavonoids or ascorbic acid, to a transparent or an already absorbing biological fluid according to the invention can therefore result in additional absorbance and reduced light penetration, if the additive absorbs at the germicidal wavelengths. The addition of 0.1 or 0.5% ascorbic acid to apple juice exposed in a flat 0.2-mm deep flow-through cuvette by a Hanovia Bio-Steritron lamp decreased the residence time-dependent inactivation rate of microorganisms to ~50% and ~20% of the juice without additives (Mack et al. 1959).

In a preferred embodiment of the present invention, the effective dose is measured using chemical dosimetry. A dosimetric solution is a solution prepared from reagents, which undergo a substantial photochemical reaction at the wavelengths to be measured, thereby generating a photoproduct that can be measured. The photoproduct can be measured with sufficient sensitivity in layers thin in relation to the absorption coefficient of the solution, so that only a small fraction of the incident radiation is absorbed within this layer, thereby enabling a fluence determination because light energy radiating onto an area of a layer passes the layer practically unabsorbed. Preferred embodiments are provided in Examples 1 to 6, 10 to 13, and 15 to 17.

A number of chemical actinometers are generally known and are sufficient to use the invention. For example, a dosimetric solution suitable for the UV-C irradiation can be selected from the group consisting of alkali metals, alkaline earth metal and ammonium salts of iodide, and aqueous uridine phosphate.

A feature of the present invention is that the method for validation of devices used for the photoinactivation of microorganisms allows to apply a dosimeter solution with a predetermined absorbance at the irradiation wavelength, or preferably with a predetermined absorbance and a predetermined viscosity to match the absorbance or both the absorbance and the viscosity of the biological fluid to be light-irradiated for microorganism inactivation at the irradiation wavelength.

A number of UV-C-sensitive chemical dosimeters especially suitable for concentrated, i.e. highly absorbing, biological fluids can be used with the instant invention. For example, diluted potassium iodide-potassium iodate actinometers, preferably, but not limited to, containing $\geq 6.96$ mM KI and 1.16 mM $KIO_3$, possess a high absorbance corresponding to the absorbance of such a biological fluid, for example, but not limited to, $a_{253.7}$ at least about 2/cm, a high quantum yield, and a high specific extinction coefficient of triiodide. This dosimeter solution can be prepared with the corresponding concentrations of potassium iodide and potassium iodate to match absorption coefficients of biological fluids preferably, but not limited to, with an absorption coefficient $a_{253.7}$ at least about 2/cm, and it is usable in thin layer cuvettes, preferably, but not limited to, with an optical path length of about 0.1 to about 1 mm, preferably of about 0.1 to about 0.7 mm, more preferably of about 0.1 to about 0.5 mm, more preferably of about 0.1 to about 0.3, more preferably of about 0.3 to about 1 mm, more preferably of about 0.5 to about 1 mm, more preferably of about 0.7 to about 1 mm. By the addition of polyvinylpyrrolidone (PVP), which is known for its stabilizing effect on tri-iodide, the sensitivity of the iodide/iodate solution is increased, and the viscosity of the protein solution may be matched with great accuracy.

Another preferable UV-C-sensitive chemical dosimeter especially suitable for dilute, i.e. low-absorbing, biological fluids is a sodium benzoate actinometer, which allows fluorimetric determination of the photo product in a thin layer-fluorescence cell, and which can be diluted for example, but not limited to, to match absorption coefficients, $a_{253.7}$ from about 0.1/cm to about 2/cm, preferably from about 0.4/cm to about 2/cm, more preferably from about 0.8/cm to about 2/cm, preferably from about 1.2/cm to about 2/cm, more preferably from about 1.6/cm to about 2/cm, for thin-layer fluorescence cuvettes preferably, but not limited to, with an optical path length of at least about 1×10 mm.

Still another preferable UV-C-sensitive chemical dosimeter especially suitable for very dilute, i.e. almost non-absorbing biological fluids is a potassium peroxodisulfate/tert-butanol actinometer, which also can be diluted to match absorption coefficients preferably, but not limited to, of $a_{253.7}$ up to about 0.5/cm. The dosimeter solutions are preferably, but not limited to, used in cuvettes with 0.5 to 1 cm, preferably of about 0.7 to about 1 cm path length. The photoproduct, hydrogen ions, can be measured using a pH meter by immersion of a suitable, preferably miniaturized, pH electrode.

In a preferred embodiment of the invention, the dosimetric solution can comprise agents or combinations of agents such as alkali metal iodide, alkaline earth metal iodide, ammonium iodide, aqueous uridine phosphate, alkali metal benzoate, alkaline earth metal benzoate, ammonium benzoate, alkali metal peroxodisulfate, alkaline earth metal peroxodisulfate, ammonium peroxodisulfate, tert-butanol, polyvinylpyrrolidone, bentonite, mica, montmorillonite, nontronite, hectorite, kaolinite, halloysite, dickite, a clay mineral, chalk, silica, fumed silica, baryte, gypsum, talcum, magnesia, alumina, bismuth oxychloride, zinc oxide, an alkaline earth sulphate, an alkaline earth carbonate, an alkaline earth phosphate, an alkaline earth hydroxyphosphate, an alkaline earth halogen phosphate, an insoluble silicate, an insoluble alumosilicate, an insoluble carbonate, an insoluble sulphate, an insoluble phosphate, an insoluble hydroxyl phosphate, a halogen phosphate, a perfluorinated hydrocarbon or a derivative thereof, a perfluorinated carboxylic acid or a salt thereof, and polyvinylpolypyrrolidone.

Preferably, the dosimetric solution can comprise a diluted potassium iodide-potassium iodate actinometer, a diluted potassium iodide-potassium iodate-polyvinylpyrrolidone actinometer; preferably the dosimetric solutions match the absorbance of the biological fluid at the photoinactivating wavelengths used, or the absorbance and the viscosity of the biological fluid.

If the biological fluid's turbidity, which may contribute to the overall absorbance, has to be matched, than a suitable turbidity-causing additive comprising without limitation minerals such as bentonite, montmorillonite, mica, montmorillonite, nontronite, hectorite, kaolinite, halloysite, dickite, any other suitable clay mineral, silica, fumed silica, chalk, gypsum, baryte, or polymers such as polyvinylpolypyrrolidone (PPVP) may be added to the diluted and absorbance- and/or viscosity-matching potassium iodide-potassium iodate-polyvinylpyrrolidone actinometer or to any other suitable actinometer. Preferably, the dosimetric solution can comprise a diluted sodium benzoate actinometer. More preferably, the dosimetric solution may also comprise a diluted absorbance-matching potassium peroxodisulfate/tert-butanol actinometer.

The dosimetry reagents are small dissolved molecules present in a considerable excess, which will easily diffuse to the irradiated zone. Accordingly, the dosimetry reagents will be converted by the incident light photons to the photochemical reaction product. With lamps operating at essentially constant intensity, the same number of light photons will irradiate the reactor volume and will apply essentially the same effective dose (mJ/cm$^2$) in a given time interval yielding a certain chemical dose rate ((mJ/cm$^2$)/min). Intensity of the lamps can be taken into account by controlling the total irradiating lamp dose. For a protein solution with bacteriophages or viruses, the dose rate will preferably be essentially the same for a given absorbance and viscosity.

The decadic absorption coefficient of a biological sample solution can be measured in a spectrophotometer in a cuvette sufficiently thin to keep the absorbance within the spectrophotometer's measurement range. The absorption coefficient is calculated by dividing the result by the optical path length (typically in centimeters), and the Napierian absorption coefficient is calculated by multiplying the decadic absorption coefficient with the natural logarithm of 10.

The viscosity can be determined by measurement of the flow-time in a capillary viscosimeter and multiplying the result with the capillary viscosimeter constant as it is generally known in the art.

The optical path length of the thin-layer cuvette used with the absorption-matching diluted actinometric solutions can preferably be kept small, so that only a small fraction of incident light is absorbed within the cuvette.

By calibrating using partially-absorbing diluted actinometric solutions in such thin layers, fluence may preferably be applied with the greatest accuracy possible. The absorption can be, for example, 27.3% for a solution with the decadic absorption coefficient at 253.7 nm $a_{253.7}$=15/cm in a 0.02 cm cuvette, or 19.9% for a solution with $a_{253.7}$=2/cm in a 0.1 cm cuvette, which means that the dose effective through the optical path length is 72.7% of the incident irradiant energy for the first and 80.1% for the latter (Morowitz 1950). Accordingly, the Morowitz correction factor is 72.7% for the first example given and 80.1% for the second. The self-absorption error can thus be easily calculated and corrected. For an accurate calibration, it is in general advisable not to use Morowitz correction factors below 50%, which means that the cuvette optical path length should not exceed the distance, where the light intensity has been reduced to 25% of its initial value.

For establishing a dosimetric calibration plot, a light source with a known irradiance can be measured, for example, by electronic radiometry, spectroradiometry, or chemical actinometry with a concentrated and fully absorbing actinometer solution. After determination of the irradiance incident from the light source, a cuvette containing the diluted absorbance-matching or absorbance- and viscosity-matching dosimetric solution is irradiated at a defined geometry and irradiance for a defined time to apply a defined surface dose, and the obtained actinometric signal is measured and plotted against the light dose.

This calibration can be accomplished by using, for example, a lamp, a shutter within the optical path to expose the cuvette for a defined exposure time, and a cuvette mounted parallel to the lamp at the end of the optical path. Such shutters are used, for example, as film-plane shutters in photographic cameras, and the shutter mechanism is accurately controlled by mechanical clockwork, or preferably by an electronic oscillator. The oscillator-driven shutter and the fixed cuvette position ensure a reproducible and accurate exposure of the cuvette. To produce this, a commercially available 35 mm or medium format film single-lens reflex or rangefinder camera body can be modified by attachment of a lamp fixture to the camera lensmount, and attachment of a cuvette to an aperture milled into the camera back. Preferably, the aperture in the camera back itself should have dimensions enabling the entire surface of the cuvette to be illuminated, while the edges of the aperture act as a partial collimator. To improve stability of lamp intensity and the actinometric quantum yield, the lamp and the cuvette insert can be thermostated by such devices as a fan, a circulating liquid, or a Peltier element.

Figure 12:
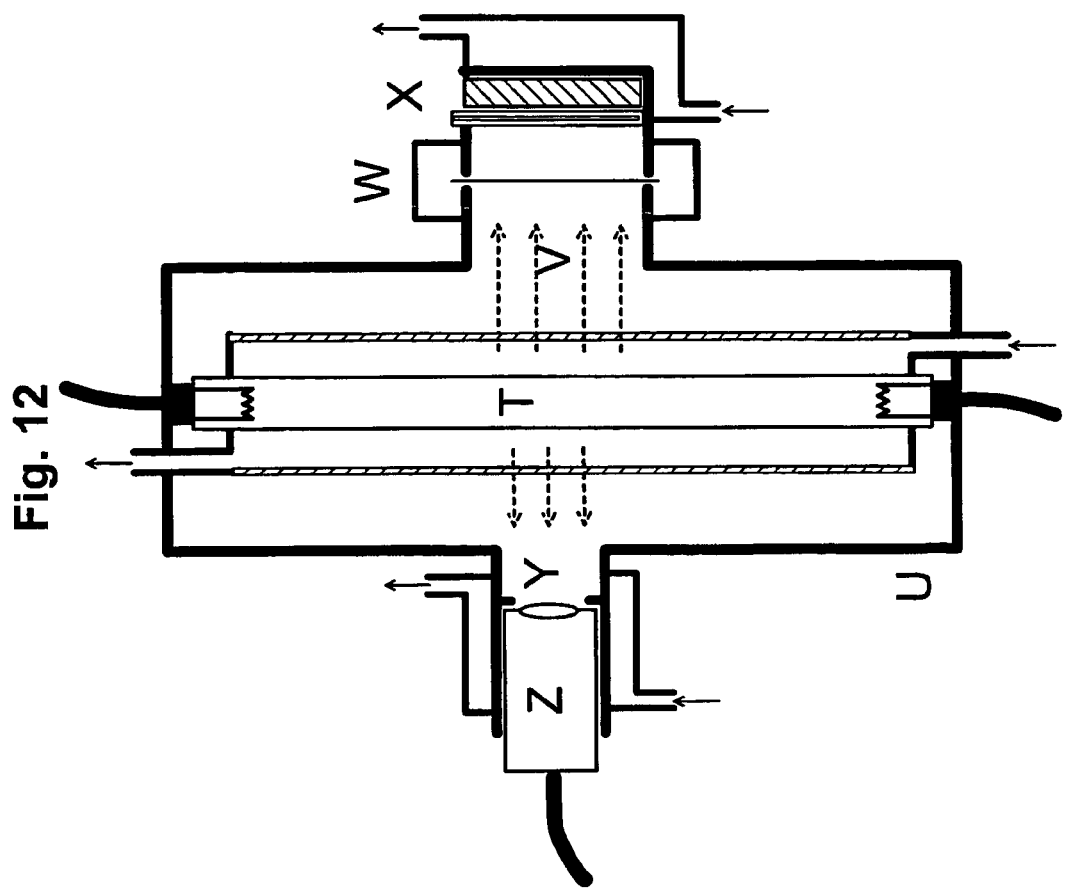
FIG. 12 depicts an exemplary calibration device of the instant invention (cf. Example 17).

The device for calibration may preferably comprise a light source, a light exit aperture allowing the light to radiate into an collimator aperture, a shutter, and a cuvette slot mounted in a thermostated housing with a light entrance aperture allowing light to radiate onto the cuvette or optical cell containing the dosimeter solution. A preferably thermostated mount may be provided for the attachment of radiometer sensors, wherein light radiates simultaneously from the light source both through the shutter onto the cuvette and through the aperture onto the entrance window of the sensor, to monitor the light source through the calibration process, or to check the time-constant properties of such a sensor by comparison with an actinometer solution according to the state-of-the-art contained in the simultaneously exposed cuvette or optical cell. Very preferably the shutter is driven by an accurate timer to achieve an exact and reproducible exposure time of the cuvette or optical cell. A preferred calibration device is shown in FIG. 12. The preferably tubular lamp (T) mounted in a housing (U) is preferably thermostated or current-stabilized, very preferably both thermostated and current-stabilized, to achieve an essentially constant light radiance through the calibration process. As indicated in FIG. 12, the thermostatization is preferably achieved by a light-transparent liquid flowing past the lamp. The light, indicated by the arrows pointing away from the lamp, is radiating through an aperture (V) past the time-controlled opened shutter (W) onto the cuvette inserted together with its distance adapter, if the cuvette is thinner than the maximum space in the holder, into the cuvette holder (X), which is preferably thermostated. The cuvette containing the actinometry or the model dosimetry solution is accurately and precisely exposed during the opening of the shutter. An optional aperture (Y) located on a place other than that for the aperture (V), but preferably in a way so that the light radiates spatially similar from the lamp into both apertures (V and Y), may accommodate an electronic sensor (Z), such as preferably, but not limited to, one of the sensors used for the reactor radiometry, providing an accurate method to recalibrate the sensor based on the ratio of the intensities preferably measured simultaneously by actinometry in the cuvette holder (X) and by radiometry with the sensor (Z). The sensor (Z) may also be used for the monitoring and recording of the lamp intensity during the calibration exposure, and for the subsequent intensity correction, if the lamp intensity changed during this calibration exposure. The use of such a device for calibration is also described in Example 17 and can also be applied to check and re-calibrate radiometer sensors by attaching a mount for a radiometer sensor to the lamp fixture, so that light emitted from the lamp can be measured simultaneously by the actinometer cuvette and the radiometer sensor.

According to a preferred embodiment of the method for determining an effective dose of light to inactivate microorganisms present in a biological fluid, the defined fluence can be modified by changing the defined irradiance and/or by changing the defined time determined by the flow rate of the biological fluid in the flow-through-reactor. The defined fluence can also be altered by changing the wavelength or spectrum of wavelengths of the emitted light since the susceptibility of the microorganisms to irradiation based inactivation at a given intensity of light emission is also a function of the wavelength or spectrum of wavelengths of the light.

To achieve a higher flow-rate the manufacturer Wedeco Visa AG of the aforementioned thin-layer irradiators recommends increasing the flow-through capacity either by connecting several single irradiators serially, or by using them in a parallel configuration. The dose can be increased by a longer residence time through using a lower flow rate, or by increasing the number of serially connected irradiators at an essentially constant flow-rate. To improve flow characteristics, a helical flow guide can be inserted in the annular gap (Harrington and Hills 1968). Static mixing by baffles is used in the blood processing apparatus described in U.S. Pat. No. 6,586,172, which uses assisted air flow cooling for the removal of heat from the UV lamp.

In this regard, a more efficient method with a higher degree of mixing will narrow the residence time distribution and increase the inactivation rate. Such a higher degree of mixing can be achieved for example, but not limited to, by the imposition of transversal mixing on the longitudinal flow, as effected statically by baffles, or the dynamically by the generation of Taylor-vortices or Dean-vortices.

To measure the effective light dose, for example, a volume of the dosimetric solution equal to the product volume is irradiated in the irradiation device, and a small sample volume is drawn at a defined time and filled into the thin-layer cuvette, and the light-generated reaction product is measured. The signal obtained from the irradiated dosimetry solution used is recorded, and compared with the corresponding calibration plot. The dose is then read out from the calibration plot. Alternatively, at least one means for measuring the effective light dose is contained in the reactor. In the case of a flow-through-reactor such means may be fitted before and after the irradiation inactivation zone.

The calibration of an UV-C irradiation device by absorption- and viscosity matching or absorption and turbidity- and viscosity-matching chemical dosimetry can for example be done experimentally on a very simple UV-C flow-through irradiator, such as a helically coiled UV-transparent tube wrapped around the illuminating low-pressure Hg vapor lamp.

The chemical method of dosimetry with actinometric solutions is able to measure an average light dose (fluence) applied to the sample volume filled into a thin-layer cuvette. The photochemical reactants are usually present in excess, any local surplus of the photochemical reaction product is readily mixed and diluted, and the concentration of the reaction product increases in an ideally linear ratio to the number of photons applied.

Generally, the same number of photons will inactivate the same fraction of the remaining viable microorganisms per volume or titer, and any decrease in the logarithm of the titer is linear. Furthermore, a local excess of light intensity cannot reduce the number of viable microorganisms to less than zero, while a locally insufficient light dose will leave a residual number of viable microorganisms present in the sample.

Preferably the method further comprises monitoring the intensity of the one or more light sources during the irradiation in order to determine an irradiating dose. More preferably the light is in the UV range, preferably in the UV-C range. Radiometric monitoring of a light source is a conventional practice for flow-through devices. Lamp power can be continuously monitored and the signal displayed or recorded. Advantageously the optical path between the light source and the radiometric sensor is not obscured by the fluid to be treated, so that the fluid does not attenuate the light intensity. If such an attenuation cannot be avoided due to design constraints, the un-attenuated lamp intensity has to be measured preferably before and after the irradiation of the fluid, so that an average intensity can be calculated.

To establish a dosimetric calibration plot, the chemical dosimetry solution is spread into a thin film of defined depth, and absorbs only a small fraction of incident light. The film is exposed to a light dose and undergoes a substantial and quantifiable change by conversion of a chemical species to yield a light absorption or a fluorescence emission at a defined wavelength, or a pH increase. The actinometric signal is measured and plotted against the light dose.

The corresponding solution can then be irradiated in a mixed batch volume, and a volume is drawn and the light-generated reaction product is measured. The signal obtained from the irradiated dosimetry solution is recorded and compared with the corresponding calibration plot. This will yield an effective dose corresponding to a signal increase in the dosimetric calibration plot. The dose rate is then calculated as dose-increase divided by the irradiation time unit. The effective dose is the dose as defined above.

The dosimetric solution simulates a target protein solution because the dosimetric solution has the same absorbance at defined wavelengths as the protein solution and preferably also the same viscosity. Measuring conversion of chemical species formed by light, such as triiodide, can be correlated with an effective LTV-dose. Chemical dosimetry ensures that protein solutions with different absorbances will receive the same effective target UV dose. For details it is referred to Examples 1 to 5 and 6.

According to a preferred embodiment of the method for determining an effective dose of light to inactivate microorganisms present in a biological fluid, the method further comprises determining the dose-distribution by titration of the number of viable microorganisms before and after, or before, during and after irradiating the biological fluid spiked before or during, or before and during the irradiation with the viable microorganisms. In another embodiment, the biologically effective light dose (fluence) is determined by biodosimetry, which refers to a determination by the photoinactivation of microorganisms. Biodosimetry can be done with batch as well as with flow-through-irradiation devices and has been conventionally used as a suitable method for measurement of residence time distribution (Qualls and Johnson 1983) and light dose distribution (Cabaj and Sommer 2000). A preferred embodiment are described in Examples 3 to 6, and 12 to 17.

In a preferred embodiment, biodosimetry can be used in combination with chemical dosimetry to determine mixing efficiency (cf. Example 3 to 6 and 12 to 17).

Preferably, the biological fluid according to the invention may contain microorganisms selected from species of the taxonomic monera kingdom, spores of the species of the monera kingdom, non-pathogenic or microorganisms species of the fungi kingdom, spores of the species of the fungi kingdom, archaea, prokaryotes, preferably bacteria, eukaryotes, viruses to ensure that such or similar microorganisms are killed or reduced in activity, and bacteriophages.

Preferably the viruses are selected from Parvoviridae viruses, Minute Murine Virus (MMV), Canine Parvovirus (CPV), Bovine Parvovirus (BPV), Porcine Parvovirus (PPV), Feline Parvovirus (FPV)), Circoviridae viruses, Circinoviridae viruses, Picornaviridae viruses, preferable Hepatitis A Virus (HAV) and Encephalomyocarditis Virus (EMC), Anelloviridae viruses, Enteroviridae RNA viruses, Microviridae DNA bacteriophages, and Leviviridae RNA bacteriophages.

To ensure that the components of interest such as proteins and other important biological molecules are preserved in the biological fluids subjected to light inactivation treatment according to the invention, the biological activity of the proteins or e.g. of vitamins can be measured using functional assays for such analytes generally known in the art, such as the elastase inhibition assay described in Example 4 or the amidolytic FX assay as described in Examples 13 and 16. These activity assay analytes may preferably be included into the biodosimetric solutions. Preferably, the absorbance, viscosity and/or turbidity of the biodosimetric fluid is adjusted such that the dosimetric solution including the added activity assay analytes matches the absorbance, viscosity and/or turbidity of the biological fluid determined after the activity assay analytes have been added to the fluid. Such assays ensure that while effectively inactivating the contaminating microorganisms, the biological fluid and/or its components of interest retain the desired biological activity.

Microorganisms, such as bacteriophages, viruses, and bacteria ideally exhibit exponential decay in viability. This means that a given dose will inactivate the same fraction of viable microorganisms, for example, if 1 mJ/cm$^2$ reduces the initial titer to $\frac{1}{10}$th, then 2 mJ/cm$^2$ to $\frac{1}{100}$th, 3 mJ/cm$^2$ to $\frac{1}{1000}$th, and so on. If all microorganisms were exposed equally by transporting all microorganisms only once to the irradiation zone, then all microorganisms would receive an inactivating hit. However, even the smallest microorganisms such as single-stranded DNA bacteriophages are large particles (~25 nm) compared with proteins, and are moved by convection and flow of the protein solution. In a reactor, some microorganisms are transported during a defined time interval several times to the irradiation zone, while others only once, and others not at all. So the inactivation rate, based on the chemically determined dose-rate, increases with mixing. Accordingly, the faster the microorganism inactivation proceeds, the shorter the necessary irradiation time, and the smaller the required effective dose has to be. Therefore, protein or other biological activity will preferably be retained at a higher mixing efficiency.

Biodosimetric inactivation by a microorganism titer of a biological fluid spiked before or during, or before and during the irradiation with the viable microorganisms is measured before, during and/or after UV-irradiation. For example, this can be accomplished by counting the number of residual colonies of viable bacteria, or lysed bacteria plaques which correspond to the number of bacteriophages still alive. The titer of viable microorganisms as colony- or as plaque-forming units (cfu and pfu, respectively) is then calculated as $\log_{10}$ ((cfu or pfu)×$10^{dilution\ factor}$) per mL of diluted sample volume titrated on a petri dish.

The biodosimetry allows validation that different protein solutions have been irradiated with essentially the same effective dose at the same mixing efficiency when the phage inactivation rate (log [number phages inactivated]/effective UV dose) is similar or essentially identical. Biodosimetry is particularly suitable for validation of different samples if these do not contain any substances toxic or inhibitory to the microorganisms or their hosts. Accordingly, biodosimetry can be used with virtually all biological fluids.

In another preferred embodiment of the invention biodosimetry can be performed using microorganisms as defined above.

The biological fluid can be irradiated in thin-film or in transversally-mixed tubular reactors, for example. If the light does not radiate directly onto the fluid surface, the material of the fluid-containing conduits in the light-irradiated inactivation zone has to be essentially transparent to the photoinactivating wavelengths. For UV light having less than about 350 nm, borosilicate glass, and for UV light having less than about 300 nm, specialty glasses, such as iron-free borosilicate glass, phosphate glass, high-silica glass, or fused quartz glass are sufficiently transparent, as well as some specialty plastics, preferably fluoropolymers, are particularly preferred. A wide variety of microorganism photoinactivation reactors can thus be designed to treat fluids of different opacity at different flow-rates. The fluid can comprise at least one additive to reduce damage and loss of biological activity or a substance of interest in the fluid.

In a preferred embodiment of the method for determining an effective dose according to the invention, the method can be performed in conjunction with at least one other sterilization or microorganism inactivation method. Various inactivation, sterilization, disinfection or preservation methods are known, such as, but not limited to, thermal and non-thermal methods, or the addition of chemical preservatives. Different types of microorganisms can have different susceptibilities to different treatments. Therefore, combinations of different treatments to ensure inactivation of all the different viruses present are often necessary. A particular benefit of the irradiation treatment of the present invention is that certain types of virus, which are resistant to other readily available treatments, are susceptible to irradiation treatment.

In another embodiment, the instant method for determining an effective dose according to the invention is used in combination with various other known methods for sterilization of biological fluids and viral inactivation. Various methods are well known in the art and include conventional wet heat treatment or pasteurization comprising incubation of fluid at an elevated temperature for a given period of time with or without stabilizers, as generally used for albumin. An alternative is dry heat treatment comprising incubation of freeze-dried fluid components at an elevated temperature for a given period of time as used for components such as Factor VIII. Another method includes ultra-filtration and solvent detergent treatment. With this method the fluid is intimately admixed with a solvent detergent system such as 1% tri(n-butyl)phosphate (TNBP) and 1% Triton X-100 or Tween 80, and incubated together for a given period of time followed by removal of the solvent detergent system, conveniently by hydrophobic chromatography. Details of solvent detergent treatments are described in WO 94/28120; and U.S. Pat. Nos. 4,946,648; 4,481,189; and 4,540,573.

In another embodiment of the instant method for determining an effective dose according to the invention is used in combination with a solvent detergent treatment. One feature of solvent detergent treatment is that it can give rise to significant increases in the absorbance of fluids treated. Therefore the ability of the present invention to achieve effective viral inactivation in fluids with relatively high absorbance is a particular advantage.

In another embodiment of the invention, the instant method for determining an effective dose according to the invention, the biological fluid comprises at least one additive, to reduce damage and/or loss of biological activity of the fluid. Various protective additives are known of this type such as vitamin E for protecting cells against damage, ascorbate to protect against loss of functional activity of plasma constituents, and quenchers of free radicals and active forms of oxygen including histidine, rutin, quercetin and other flavonoids, and other stabilizers such as sugar alcohols including mannitol and amino acids for reducing loss of functional activity of blood components. Because the generation of singlet oxygen would require dissolved oxygen, the removal of oxygen dissolved in the solution, e.g. by evacuation, before irradiation and replacement of air during irradiation by an inert gas, e.g. by nitrogen, can exert a beneficial effect on substances of interest. In case the protective additives have an influence on the susceptibility of the microorganisms to irradiation, in order to account for the effect of the protective additives on the effective dose for inactivating microorganisms, dosimetry may be adjusted as set forth e.g. in Example 16.

According to the method of the invention the effective dose is the dose, which inactivates essentially all, preferably at least about 99.9%, more preferably 99.99%, even more preferably 99.999% of the microorganisms present in the biological fluid. Even more preferred is that the method is operated in a flow-through reactor. Preferred embodiments are provided in Examples 2, 5, 6, 11, 15, and 17.

According to another aspect of the invention there is provided a method for determining an effective dose of monochromatic or polychromatic light from one or more light sources to inactivate microorganisms present in a non-transparent biological fluid, comprising measuring the effect of the monochromatic or polychromatic light on a dosimetric solution matching the turbidity of the biological fluid at the photoinactivating wavelengths used, the turbidity and absorbance of the biological fluid, the turbidity and the viscosity of the biological fluid, the turbidity and the absorbance and the viscosity of the biological fluid, the absorbance of the biological fluid, or the viscosity and absorbance of the biological fluid, based on a light dose calibration by i) irradiating the dosimetric solution in a layer of an optical path-length sufficiently thin to absorb only a fraction of the incident light at a predetermined defined irradiance for a defined time to apply a defined fluence (light dose) resulting in a change of a measurable physical or chemical magnitude, and ii) by reading out the dose corresponding to the change in the magnitude measured during or after the light irradiation of the dosimetric solution in the light irradiation reactor, wherein step i) is executed before step ii) or vice versa.

In a preferred embodiment the biological fluid is a fluid as defined above.

A non-transparent biological fluid within the meaning of the invention preferably relates to a colloidal biological fluid which appears visually clear or hazy, but display light scattering along the optical path e.g. of a light beam. Preferably the colloidal biological fluid contains particles of a size in a colloidal dispersion between about 0.1 nm and about 100 nm, preferably between about 1 nm and about 100 nm, more preferably between about 10 nm and about 50 nm. Even more preferably, the light scattering is enhanced near the molecular absorption maximum of a colloidally dispersed macromolecule contained in a colloidal biological fluid, so that scattered light may contribute to pathogen photoinactivation. For a preferred colloidal biological fluid such as a protein solution, it is possible to extrapolate the fraction of the total absorbance contributed by the turbidity by extrapolation from turbidity measurements at non-absorbed wavelengths to the absorbed wavelength. The molecular absorbance has then to be calculated by subtraction of the extrapolated turbidity from the spectrophotometrically measured total absorbance. To simulate the scatter properties of such a colloidal dispersion in a colloidal biological fluid, it may be possible to fractionate a turbidity-causing agent as described above such as a clay mineral by sedimentation, and use the fraction of the desired particle site, to match the turbidity in a dosimetry model solution.

It is even more preferred if the non-transparent biological fluid is a biological fluid containing suspended particles having particle sizes of at least about 100 nm which are generally known in the field and described in detail above. Turbidity of such a biological fluid such as apple cider or citrus or vegetable juice can, for example, be determined by absorbance measurement before and after removal of the suspended particles through e.g. filtration or centrifugation. The absorbance of the clarified solution without any suspended particles is caused by the molecular chromophores. The difference between the measured absorbance values of the turbid fluid and the clarified fluid is the turbidity.

It is also preferred if the non-transparent biological fluid is a liquid emulsion such as milk, which is a fat-in-water-emulsion, scattering light in a way that turbidity contributes most to the total light attenuation. For UV dosimetry model emulsions comprising reagents as described above, chemically inert and UV-transparent emulsifiers and emulgated liquids would be required, preferably perfluorinated carboxylic acid salts and perfluorinated hydrocarbons or derivatives thereof.

In order to adjust the dosimetric solution to match the absorption and turbidity of a non-transparent biological fluid, in a first step the absorbance of the non-transparent biological fluid is determined at the photoinactivation wavelength used (turbid absorbance value). Then, upon removal of the turbid components of the biological fluid, preferably by filtration, the absorbance of the biological fluid is determined again at the photoinactivation wavelength (non-turbid absorbance value). A dosimetric solution having an absorption value at the photoinactivation wavelength matching the non-turbid absorbance value is prepared. Preferably the dosimetric solution's viscosity value also matches the viscosity of the biological fluid, in which fluid the turbid components have been removed. The preparation of such dosimetric solutions has been described in detail above. Subsequently, a turbidity-causing agent described in detail above, is added so that the absorbance value of the dosimetric solution matches the turbid absorbance value at the photoinactivation wavelength. Further details for the calibration of such dosimetric solutions and preferred embodiments of the invention can be derived from Examples 4 and 10.

According to a preferred embodiment of the method for determining an effective dose of light to inactivate microorganisms present in a non-transparent biological fluid, about 100%, preferably about 80%, preferably about 60%, preferably about 50%, preferably about 30%, or less of the incident irradiance is absorbed along the optical path length.

According to another preferred embodiment, the defined fluence can be modified as described above. Preferably the method further comprises monitoring the intensity of the one or more light sources during the irradiation in order to determine an irradiating dose. More preferably the light is in the UV range. Such monitoring has also been explained in detail above.

Preferably, the method for determining an effective dose of light to inactivate microorganisms present in a non-transparent biological fluid further comprises determining the dose-distribution by titration of the number of viable microorganisms before and after, or before, during and after irradiating the biological fluid spiked before or during, or before and during the irradiation with the viable microorganisms as detailed above. In another embodiment, the biologically effective light dose (fluence) is determined by biodosimetry, preferably by a combination of chemical dosimetry and biodosimetry as has been described in detail above. Preferably the method further comprises monitoring the intensity of the one or more light sources during the irradiation in order to determine an irradiating dose as described in detail above. More preferably the light is in the UV range, even more preferably in the UV-C range.

Preferably the dosimetric solution is a solution as described in detail above.

Even more preferably, the dosimetric solution comprises a diluted potassium iodide-potassium iodate actinometer, or a diluted potassium iodide-potassium iodate/polyvinylpyrrolidone actinometer, or a diluted sodium benzoate actinometer, or a diluted potassium peroxodisulfate/tert-butanol actinometer.

It is further preferred that if the dosimetric solution contains a turbidity-causing agent described above. The dosimetric solutions are preferably adjusted to the absorbance, or absorbance and turbidity, or absorbance and viscosity and turbitity of the biological fluid at the photoinactivation wavelength as described in detail above and in Examples 4 and 10.

The microorganisms useable according to the method of the invention have also been described above.

Preferably, the method for determining an effective dose of light to inactivate microorganisms present in a non-transparent biological fluid may be carried out in conjunction with at least one other sterilization or microorganism inactivation method introduced above. More preferably the biological fluid comprises at least one additive to reduce damage and loss of biological activity of the fluid as described above. Even more preferably the method is performed with a solvent detergent treatment as shown above.

According to the method of the invention the effective dose is the dose defined above.

It is even more preferred that the method is operated in a flow-through reactor, preferably in a flow-through-reactor, comprising irradiating the biological fluid with an effective dose of monochromatic or polychromatic light from one or more light sources, wherein the effective dose is determined according to the method described in detail above and in Examples 3, 5, 16, and 17.

In addition, in another aspect of the invention there is provided a method for the inactivation of microorganism in a non-transparent biological fluid, comprising irradiating the biological fluid with an effective dose of monochromatic or polychromatic light from one or more light sources, wherein the effective dose is determined according to the method as detailed above. Such methods may be operated in any kind of irradiation reactor, preferably in batch-reactors or flow-through-reactors (cf. Example 3 to 6, 12, 13, and 15 to 17).

Preferably, in the method of determination the effective dose and the methods of inactivation, a UV-photoinactivation flow-through-reactor is used in which one or more light sources are encased by an envelope thermostat, through which envelope thermostat a thermostated and essentially light-transparent liquid is flowing to remove heat from the lamp, thereby ensuring an essentially constant lamp intensity. Preferably the flow-through reactor is a reactor type selected from the group consisting of a gravity-driven thin-film-generating type, a turbulent actively mixed flow type, a centrifugally driven thin-film-generating type, a coiled tube type, a baffled tube type, a motionless mixer tube type, a turbulent statically mixed flow-tube type, a laminar-tube type, and a turbulent flow-tube type, all of which are described in detail below.

In still another aspect of the invention there is provided a UV-photoinactivation flow-through-reactor, in which one or more light sources are encased by an envelope thermostat, through which envelope thermostat a thermostated and essentially light-transparent liquid is flowing to remove heat, preferably excess heat, from the lamp, thereby ensuring an essentially constant lamp intensity. Preferably the liquid film is a film of a biological fluid. Even more preferably the light emitted by the one or more light sources is used to photoinactivate the biological fluid. Preferably the envelope thermostat is composed of a material containing or consisting of UV-translucent, UV-resistant, and essentially chemically inert quartz glass, preferably borosilicate glass, and a translucent, UV-resistant, and essentially chemically inert polymer, such as fluoropolymer.

Excessive heat within the meaning of the invention would preferably be any thermal or infrared energy sufficient to heat up the biological fluid in the reactor, preferably in the optical path of the reactor, to a temperature causing undesired activation or loss of biological activity and finally irreversible denaturation of the fluid constituents. This temperature may depend on the fluid's composition and on the presence of stabilizers. For most enzymes and coagulation proteins heating the biological fluid to the physiological temperature optimum at about 37° C. may lead to undesired activation and subsequent consumption. More preferably, excessive heat refers to a temperature of the biological fluid in the reactor where most unstabilized plasma proteins will aggregate, i.e. at temperatures of about 55 to about 60° C. or higher. In overheated fruit juices, and the like, an off-flavor may develop.

Preferably the flow-through-reactor according to the invention is a reactor type selected from the group consisting of a gravity-driven thin-film-generating type such as the Dill irradiator, a coiled tube type (Bayha 1951), a baffled or other motionless mixer-elements containing tube type, a turbulent statically mixed flow-tube type, a laminar-flow tube type, and a turbulent flow-tube type as described in detail above.

The flow-through-reactors according to the invention provide stabilization of the lamp intensity to achieve an essentially constant radiant power through the irradiation process, reducing irradiance fluctuations associated with reactors known in the art (cf. Examples 7, 8, and 13). Further means for stabilizing light irradiance include voltage adjustment (Cortelyou et al. 1954) which can be used in combination with thermostatization. Direct thermostatization of the light source, as introduced by the flow-through-reactors according to the invention, does however warrant both an essentially constant lamp intensity and the removal of heat, preferably excessive heat. Preferably, thermostatization is achieved by pure (distilled or de-ionized) water or by any other light-transparent, light-insensitive, non-toxic and non-inflammable liquid. Preferably, the temperature and/or the flow rate of the thermostatization liquid in the thermostat envelope may also be adjusted in response to measured temperature deviations from the desired lamp temperature, which allows regulation of the degree of cooling of the lamp(s), depending on the degree of the deviation of the actual lamp temperature from the target temperature.

Preferably, light sources are also used for reactors having a fluid depth exceeding the light penetration depth, such as stirred batch reactors, or actively or passively mixing flow-through-reactors.

According to preferred embodiments of a flow-through-reactor according to the invention two modes to thermostat a low-pressure metal vapor lamp by a liquid are introduced in FIGS. 14a and 14b, which depict the cross-sectional view of the corresponding arrangements. Liquid thermostatization of the entire radiant lamp surface ensures an even lamp wall temperature distribution by avoiding condensation of metal vapor at cold spots as possible with the state-of-the-art metal heat pipe cooling (Benesi 1956), and also prevents the deposition of dust on the lamps which is associated with air ventilation based lamp cooling (U.S. Pat. No. 6,586,172).

In FIG. 14a, the tubular lamp (A) is surrounded by an inner envelope tube (B) and an outer envelope tube (C), which are preferably mounted concentrically and fabricated of a material sufficiently transparent at the pathogenicidally photoinactivating light wavelength. Between the lamp (A) and the inner envelope tube (B) there is a gap (D) preferably filled either by a gas or evacuated, the width of which may be chosen to optimize the sufficiently transparent thermostating liquid's (E) temperature, the liquid flowing through the gap between the inner envelope tube (B) and the outer envelope tube (C), so that overheating of the biological fluid is avoided. The width of the fluid-bearing gap (E) may be optimized to ensure an efficient removal of heat according to the needs of the application desired. This arrangement is particularly preferable for helical tubular flow-through reactors as described in US Patent application 2003/0049809 A1, where the preferably concentric tubular flow conduit is attached directly or preferably very closely to the lamp's envelope tube. This arrangement is also very preferable for the use of high-intensity Hg amalgam lamps, which compared to normal low-pressure Hg lamps emit a threefold UV-C (253.7 nm) surface radiance. However, at a lamp wall temperature optimum of around 80° C., this would require an effective protection of the biological fluid from such high and denaturing temperatures. Such a protection can be achieved by optimization of the gap width (D) determining the heat transfer effectiveness to the thermostating liquid (E).

In another preferred embodiment, a simplified arrangement (FIG. 14b) omitting the inner envelope tube and the air gap is provided, thus achieving a direct thermostatization of the lamp (A) by the thermostating liquid (E) flowing in the gap between the lamp (A) and the outer envelope tube (C). This arrangement is particularly preferable for low-pressure Hg vapor lamps emitting the maximum UV-C (253.7 nm) surface radiance at a lamp wall temperature around 40° C., if a sufficient thermally insulating distance to the irradiation reactor avoids overheating of the biological fluid to be treated.

Most preferably, a gravity-driven thin-film irradiator such as the Dill irradiator and its derivatives, or a helical tube or helical envelope irradiator would operate more safely and gently at an essentially constant light intensity without excessive warming of the product, if the light source used for the illumination of such a reactor is thermostated by a flowing liquid. Even more preferable such flowing liquid thermostatization of the light sources is also used for reactors having a fluid depth exceeding the light penetration depth, such as stirred batch reactors, or actively or passively mixing flow-through-reactors.

Any given UV-dose can be measured in $mJ/cm^2$. Irradiating dose is the total lamp power over time. However, only part of this irradiating dose will become effective as measured by chemical dosimetry and inactivation of bacteriophages. For example, a 30 L batch reactor can require an irradiating lamp dose that is about 1000 times higher than the effective target dose. As shown above, determination of an effective dose by chemical dosimetry also yields irradiation time. In the case of slightly changing lamp power, the irradiation time can be replaced by the irradiating dose. This is determined by recording lamp intensity during the irradiation runs of the model dosimetry solutions. While the virucidally effective target dose is determined, intensity counts are summed up over the irradiation time to obtain the radiometric target lamp dose corresponding to the effective target dose. Control of the process by irradiating lamp dose can compensate for changes in lamp power and can increase the accuracy of the instant method.

In another aspect of the invention there is provided a method of controlling the light sum dose of monochromatic or polychromatic light emitted from one or more light sources to effectively inactivate microorganisms present in a biological fluid in a batch reactor, comprising the steps of:

a) determining the absorption-dependent irradiation source target light sum dose based on the effective dose of monochromatic or polychromatic light to inactivate microorganisms present in the biological fluid, the irradiation light dose rate and the irradiation time necessary to effectively inactivate the microorganisms in the batch reactor;

b) recording the irradiation light dose rate and the irradiation time during inactivation of the microorganisms present in the biological fluid in the batch reactor;

c) calculating the absorption-dependent irradiation source light sum dose based on the measurements in step b);

d) comparing the absorption-dependent irradiation source light sum dose determined in step c) with the absorption-dependent irradiation source target light sum dose determined in step a); and e) discontinuing light exposure of the biological fluid once the absorption-dependent irradiation source light sum dose is equal to or greater than the absorption-dependent irradiation source target light sum dose. Preferably the method is continued until the absorption-dependent irradiation source light sum dose is essentially equal to the absorption-dependent irradiation source target light sum dose despite irradiation light dose rate variations and/or intermediate switching off of at least one of the one or more light sources. More preferably, the effective dose is determined as described in detail above. Even more preferably, the recording of the irradiation light dose rate and the irradiation time is carried out using at least one electronic radiometer, at least one chart recorder, and/or at least one sum counter.

A preferred embodiment of the method is described in Examples 7, 8, and 15. Preferably the methods also accounts for irradiation fluctuations.

The target light sum dose may preferably be determined as follows: First the batch reactor is validated for different model dosimetric solutions having different absorption coefficients to determine the effective dose rate (in $(mJ/cm^2)/min$, the irradiation light dose rate (in $(mJ/cm^2)/min$, and the irradiation time necessary for a given effective dose. The effective dose of monochromatic or polychromatic light to inactivate microorganisms present in the biological fluid is determined preferably by chemical dosimetry as has been described in detail above. Then the irradiation light dose rate and irradiation time are monitored as described in detail in the next paragraph. The absorption-dependent irradiation source light sum dose is calculated as the radiometer sum signal increases over the irradiation time. In general, the irradiation light dose rate is orders of magnitudes higher than the chemical dose rate, because the radiometer sensors receive the UV light practically un-attenuated by any absorbing medium. The irradiation time for a given absorption-dependent irradiation source target light sum dose effective in the biological fluid is multiplied by the absorption-dependent irradiation source light dose rate to calculate the absorption-dependent irradiation source target light sum dose as the irradiation parameter.

Preferably the recording of the irradiation light dose rate and the irradiation time is carried out using standard equipment such as at least one electronic radiometer, at least one chart recorder, and/or at least one sum counter as detailed above and in Example 7 and 8. Lamp power (irradiation light dose rate) can be continuously monitored and the signal displayed or recorded. Advantageously the optical path between the light source and the radiometric sensor is not obscured by the fluid to be treated, so that the fluid does not attenuate the light intensity. If such an attenuation cannot be avoided due to design constraints, the un-attenuated lamp intensity has to be measured preferably before and after the irradiation of the fluid, so that an average intensity can be calculated. The electronic radiometer preferably comprises a drift-insensitive photoelectric radiometer sensor. Such recording permits calculation of the absorption-dependent irradiation source light sum dose based on the measurements of the irradiation light dose rate over irradiation time. Even if the irradiation fluctuates or is temporarily discontinued, such setup allows accurate determination of the absorption-dependent irradiation source light sum dose the biological fluid has been exposed to. In a preferred embodiment, by comparison of the absorption-dependent irradiation source light sum dose with the absorption-dependent irradiation source target light sum dose it is possible to determine or even anticipate the time point when the irradiation inactivation may be discontinued in order to make sure that the biological fluid essentially received the effective dose of irradiation to effectively inactivate the microorganisms while at the same time the method preferably also ensures that the biological fluid is essentially not affected by being excessively exposed to the irradiation. To this end the means for comparing the absorption-dependent irradiation source light sum dose with the absorption-dependent irradiation source target light sum dose may be connected to a switch which turns of the power supply of the light source employed to irradiate the biological fluid. Alternatively any other means effective to discontinue exposure of the biological fluid to the irradiation is also suitable and is generally known in the art.

Preferably, the method is continued until the absorption-dependent irradiation source light sum dose is essentially equal to the corresponding absorption-dependent irradiation source target light sum dose despite irradiation light dose rate variations and/or intermediate switching off of at least one of the one or more light sources. Such an absorption-dependent irradiation source target light sum dose can also be derived from interpolation between absorption-dependent irradiation source target sum light doses determined for different absorbances. The method has been described in detail in Example 6 and 7.

Batch irradiation has the advantage over the flow-through irradiation methods that the entire batch volume is exposed by mixing to an average intensity until effective inactivation of all microorganisms has been achieved (Brooks 1920).

A batch irradiation reactor may either comprise a container for the fluid to be treated, which is at least partially fabricated of a material essentially and sufficiently transparent at the photoinactivating pathogenicidal wavelength, and which is illuminated from light sources mounted outside, or a vessel for that fluid, where the contained fluid volume is either irradiated from light sources mounted above the liquid surface, or by light sources immersed into the fluid. The entire volume is stirred and mixed so that an essentially effective and homogeneous exposure of all volume fractions to the photoinactivating pathogenicidal light is assured. Until present no such reactor has been applied in practice due to the lack of a suitable process validation and control method.

Preferably, the external light sources radiate the light onto the irradiation container such that the lamp sensors are not obscured by the absorbing fluid to be treated and the essentially un-attenuated light intensity is thus received by the sensors, lamp intensity measurements are preferably made continuously. The radiometric target lamp dose increases in a linear ratio with the absorption of the protein solution. Lamps operating at a lower intensity will take more irradiation time to reach the radiometric target lamp dose.

The following examples illustrate embodiments of the invention, but do not limit the scope of the invention in any manner.

EXAMPLE 1

Absorption Coefficients of the Iodide/Iodate Actinometer Solution at High Dilution and Dosimetric Response of the Iodide/Iodate Actinometer Solutions A solution containing 0.24 M KI and 0.04 M $KIO_3$ in 0.01 M borate buffer, pH=9.25, was diluted 0.2-, 0.4-, 0.6- and 0.8-fold with 0.01 M borate buffer and the absorption measured in a 0.1 mm cuvette. FIG. 1 shows that the absorption coefficient depends in a linear ratio ($a_{253.7}$=69/cm×dilution factor) on the concentration.

Figure 2:
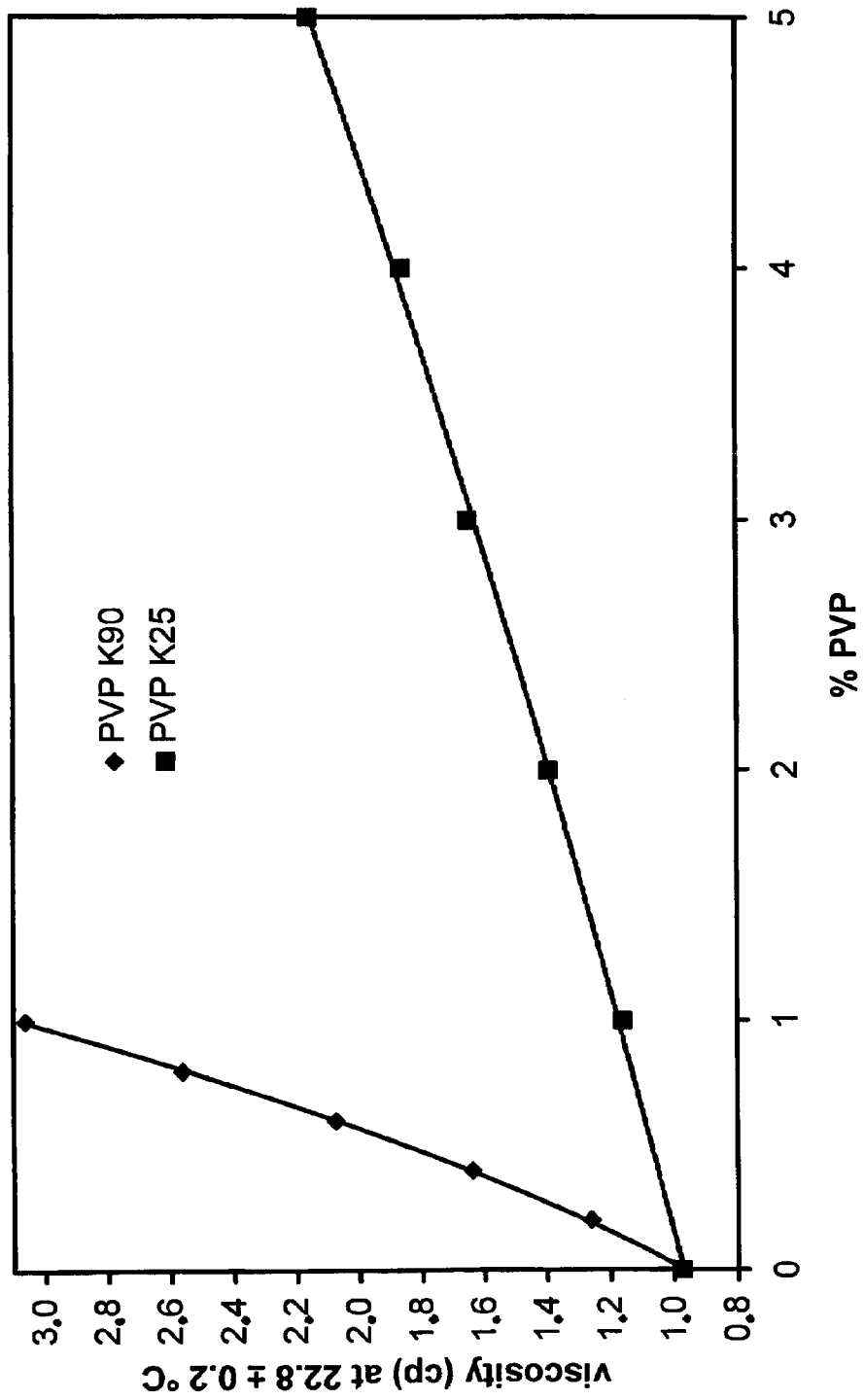
FIG. 2 depicts the non-linear relation between increase in viscosity and polyvinylpyrrolidone concentration (cf. Example 1).

Solutions containing 10 g polyvinylpyrrolidone K90 (PVP K90; average molar mass 360000 Da) in 1 L 0.01 M and 50 g PVP K25 (average molar mass 29000 Da) in 0.1 M borate buffer were diluted 0.2-, 0.4-, 0.6-, 0.8-fold in the corresponding buffer and the viscosity of the dilutions and the buffer were measured in a Schott 0.40 mm Ubbelohde capillary viscosimeter thermostated at 22.8° C. It can be seen from FIG. 2 that the viscosity increases with the concentration in a non-linear ratio.

Figure 3:
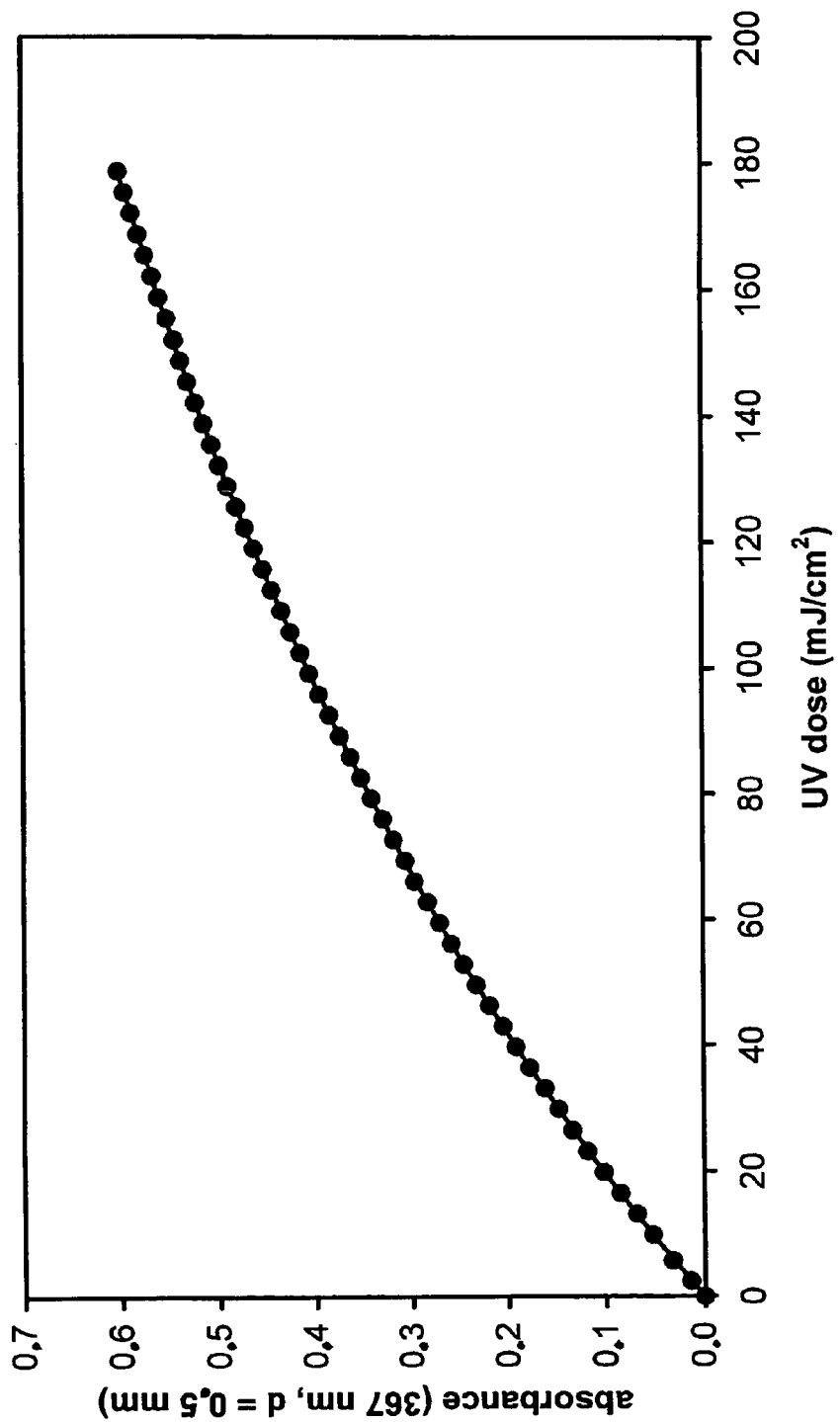
FIG. 3 depicts the calibration plot for the 2.5/cm model solution (cf. Example 1).
Figure 4:
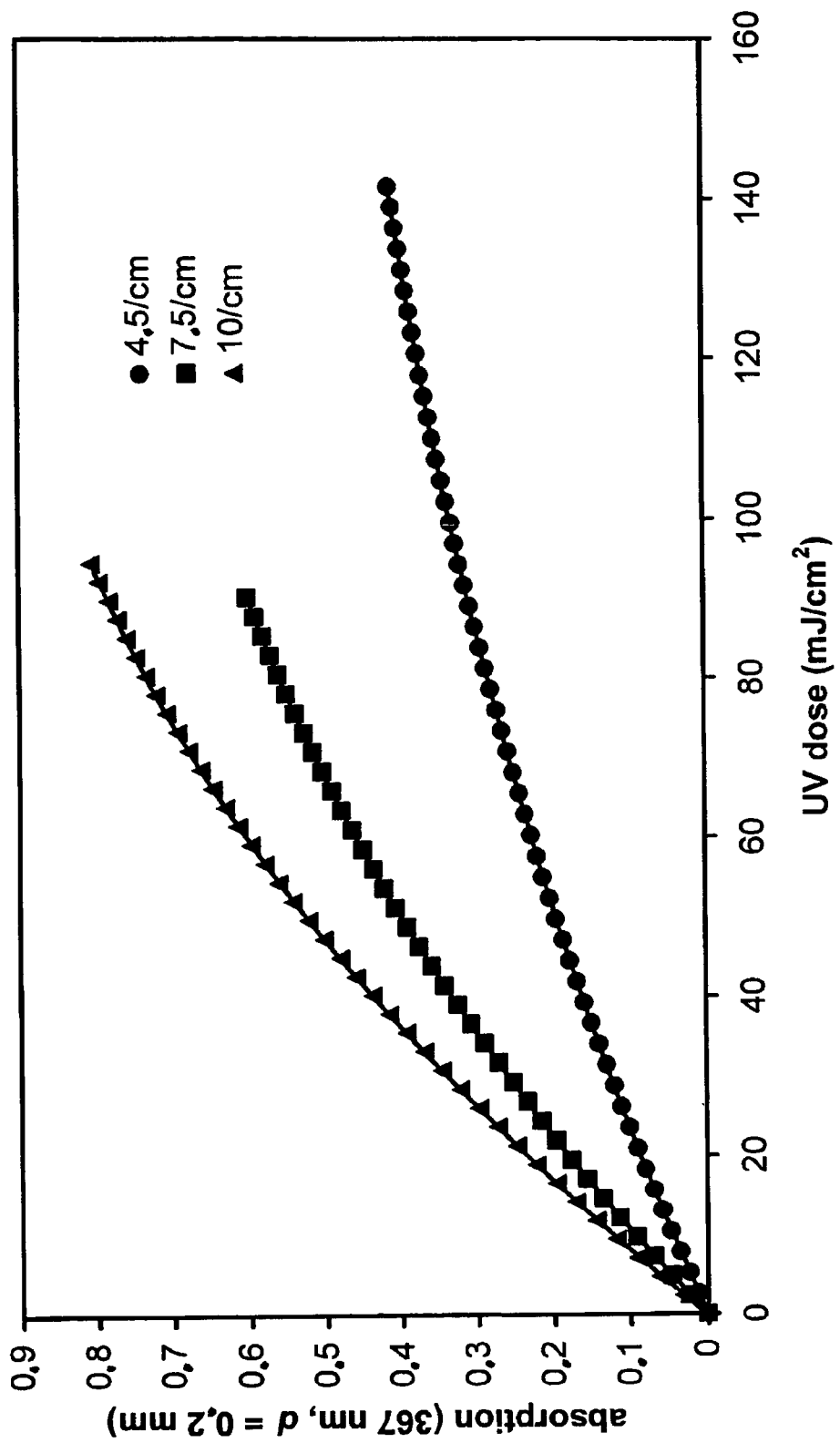
FIG. 4 depicts the calibration plots for the 4.5/cm, 7.5/cm and 10/cm model solutions (cf. Example 1).

Dosimetry solutions with a decadic absorption coefficient $a_{253.7}$=2.5/cm and a viscosity of 1 cp (0.00852 M KI+0.00142 M $KIO_3$+1.543 g PVP K25/L), 4.5/cm and 1 cp (0.01548 M KI+0.00258 M $KIO_3$+1.543 g PVP K25/L), 7.5/cm and 1 cp (0.02591 M KI+0.00432 M $KIO_3$+1.543 g PVP K25/L), and 10/cm and 1.25 cp (0.03478 M KI+0.00580 M $KIO_3$+1.916 g PVP K90/L) were prepared in 0.1 M borate buffer, pH=9.25, and calibration plots were recorded by incremental exposure in thin layer cuvettes (0.5 mm for 2.5/cm; 0.2 mm for 4.5/cm, 7.5/cm, and 10/cm) in a calibration device as described in Example 18 and above. The Morowitz correction factor (Morowitz 1950) was applied to correct for the self-absorption in the thin layer cuvette containing the model solution. FIG. 3 depicts the calibration plot for the 2.5/cm model solution and FIG. 4 the calibration plots for the 4.5/cm, 7.5/cm and 10/cm model solutions.

EXAMPLE 2

Determination of the Irradiation Dose Effective in a Helical Flow-Through-Reactor A floating immersion lamp for water tank UV disinfection (Microfloat 1/0, Aqua
Concept GmbH Karlsruhe, Germany) equipped with an 11 W UV-C lamp in a 23 mm diameter envelope tube was mounted upside down and a 17.5-cm long fluoropolymer coil with a coil diameter of ⅞ inch (2.22 cm), 5-mm tube diameter and 0.63-mm wall thickness (manufactured by Markel Corp., Plymouth Meeting, Pa., USA, from Hyflon MFA produced by Solvay Solexis S. p. A., Bollate, Italy) was wrapped tightly around the lamp so that the 15 cm-illumination length was fully used by the coil. A Dr. Gröbel UV-Elektronik RM-12 Radiometer with a daylight-blind UVC-TLB sensor mounted at the middle of the coil was used to check the lamp intensity when the coil was rinsed with deionized water before the start and after the end of the dosimetry measurement. Using an Ismatec BVP peristaltic pump with a ISM719 three-roller pump head and silicon rubber tubing with a wall thickness of 5 mm ID×1.5 mm, the model solutions were pumped through the coiled tube reactor at flow rates of 100, 200, 300, 400, 500, and 600 mL/min, and the dose read out in the calibration plot from the absorption in a 0.2 mm cuvette at 367 nm.

TABLE 1

| mL/min | UV-dose 2.5/cm mJ/cm$^2$ | UV-dose 4.5/cm mJ/cm$^2$ | UV-dose 7.5/cm mJ/cm$^2$ | UV-dose 10/cm mJ/cm$^2$ |
|---|---|---|---|---|
| 600 | 27.37 | 16.27 | 9.27 | not done |
| 500 | 35.02 | 20.84 | 11.51 | not done |
| 400 | 41.34 | 23.82 | 13.57 | not done |
| 300 | 55.49 | 31.74 | 18.01 | 14.57 |
| 200 | 82.32 | 47.49 | 27.53 | 22.10 |
| 100 | 158.90 | 90.25 | 53.06 | 43.07 |
| RM-12 reading (mW/cm$^2$) | start 10.16 end 9.81 mean 9.99 | start 10.70 end 10.78 mean 10.74 | start 11.07 end 11.15 mean 11.11 | start 11.28 end 11.30 mean 11.29 |

The correlation of the UV-dose to the inverse flow rate (=residence time in min/mL) is linear with a correlation coefficient $R^2$>0.999.

EXAMPLE 3

Irradiation of Human Serum Albumin and $a_1$-Antitrypsin for Virus Inactivation in the MFA Coil Based on Chemical Dosimetry and Biodosimetry Human serum albumin (20%) was diluted with 20 mM phosphate-buffered 0.15 M NaCl (phosphate-buffered saline, PBS) and bacteriophage Phi-X 174 lysate (~1×10$^9$ plaque-forming units (PFU)/mL) added in a 1:100 (v/v) spiking ratio to obtain a protein solution with an absorption coefficient of $a_{253.7}$=7.5/cm and a viscosity of 1.05 cp. The solution was pumped through the MFA coil as described in Example 2. The lamp intensity was measured as in Example 2 (with an average intensity of 11.40 mW/cm$^2$). Phi-X 174 titers of 0.9 mL sample solution were determined after serial decadic dilution by titration on the host bacteria. The inactivation rate was calculated from petri dishes having at least 10 up to 200 lytic plaques. The applied doses were corrected for the radiometric intensity (irradiation/dosimetry) ratio.

TABLE 2

| mL/min | log$_{10}$ pfu Phi-X 174/mL | UV dose (mJ/cm$^2$) |
|---|---|---|
| unirradiated | 7.36 | 0.00 |
| 200 | (0.05 = 1 pfu/0.9 mL) | 28.25 |
| 300 | 1.05 | 18.48 |
| 400 | 2.90 | 13.92 |
| 500 | 3.42 | 11.81 |

From the corresponding bacteriophage titers it can be seen that a dose-dependent inactivation rate of −0.3369 log$_{10}$ pfu/(mJ/cm$^2$) is achieved.

Human $a_1$-antitrypsin ($a_1$-proteinase inhibitor, ARALAST®) was obtained purified from plasma and diluted to an absorption coefficient of $a_{253.7}$=4.5/cm. The bacteriophage spiking ratio was 1:100 (v/v). The mean lamp intensity was 11.45 mW/cm$^2$. The applied doses were corrected for the radiometric intensity (irradiation/dosimetry) ratio. Antitrypsin activity was determined by the neutrophil elastase inhibition assay.

TABLE 3

| mL/min | log$_{10}$ pfu Phi-X 174/mL | $\Delta$log$_{10}$ pfu/mL | UV dose (mJ/cm$^2$) | Elastase inhibition (% of unirradiated) |
|---|---|---|---|---|
| unirradiated | 6.66 | 0.00 | 0.00 | 100.00% |
| 600 | 1.12 | −5.53 | 17.34 | 94.31% |
| 500 | 0.82 | −5.83 | 22.21 | 93.09% |
| 400 | 0.00 | −6.66 | 25.39 | 97.74% |
| 300 | 0.00 | −6.66 | 33.83 | 89.02% |
| 200 | 0.00 | −6.66 | 50.62 | 98.37% |
| 100 | 0.00 | −6.66 | 96.20 | 90.36% |

It can be seen that by application of chemical dosimetry and biodosimetry for a flow-through irradiation process, the lowest dose can be determined where a complete inactivation of target microorganisms is achieved.

EXAMPLE 4

Irradiation of Apple Juice for UV Pasteurization in the MFA Coil Based on Chemical Dosimetry Apple juice ($a_{253.7}$=10.1/cm, $\eta$=1.25 cp) was purchased pasteurized. Baker's yeast (*Saccharomyces cerevisiae*) was purchased fresh in food grade quality, and 50 mL of the apple juice were seeded with 100 mg fresh baker's yeast and incubated for 3 h at 37° C. The pasteurized apple juice was spiked with the yeast suspension (9.5 mL to 950 mL juice) and irradiated at a flow rate of 100, 150, and 200 mL/min. The mean lamp intensity was 11.46 mW/cm$^2$. The dose for 150 mL/min was interpolated from the results obtained in Example 2. The applied doses were corrected for the radiometric intensity (irradiation/dosimetry as in Example 2) ratio. The yeast cells were titrated at ambient light in orange serum agar, and residual infectivity was determined by a fermentation test of 50 mL unirradiated and irradiated juice incubated at 37° C. for up to 72 h. Flavor was evaluated on the unirradiated and the irradiated samples (neutral=pasteurized apple juice).

TABLE 4

| mL/min | log$_{10}$ cfu S. cerevisiae/mL | UV dose (mJ/cm$^2$) | fermentation in 50 mL at 37° C. detected after | flavor |
|---|---|---|---|---|
| unirradiated | 5.60 | 0.00 | 16 h | neutral |
| 200 | 3.40 | 22.60 | 24 h | sl. smoky |
| 150 | 3.35 | 29.60 | 40 h | sl. smoky |
| 100 | 0.52 | 44.08 | 64 h | smoky |

From the results it can be seen that the relatively high dose of >40 mJ/cm$^2$ necessary to inactivate >5 log$_{10}$ cfu/mL baker's yeast in highly UV-C absorbing apple juice can be accurately evaluated by chemical dosimetry.

EXAMPLE 5

Use of Dosimetry and Biodosimetry for the Evaluation of a Taylor Vortex-Generating Flow-Through-Reactor A Taylor vortex reactor equipped with an outer quartz tube (7 cm inner diameter, 2.7 mm wall thickness, 13.2 cm in height) and a rotating concentric inner stainless steel cylinder (diameter 54.85 mm) with a total volume of 196.1 mL was illuminated from the side with up to six low-pressure mercury lamps, each mounted in a quartz envelope tube immersed into a concentric toroidal water bath with a concentric inner quartz window, and equipped with a stainless steel reflector behind. The flow rate of the liquid passing the vertically mounted cell upwards could be adjusted by a Watson-Marlow 505 U peristaltic pump. The rotation rate of the cylinder was also adjustable. Cooling water from a thermostat was pumped through the lamp envelope water bath to keep the lamp temperature and the UV-C-output essentially constant. After each change of an experimental parameter, 5 cell volumes were pumped through the cell before a sample was drawn.

The flow rate was changed while the rotation rate was kept constant at 60 rpm. The UV dose was measured by the model solutions given in Example 2. At 60 rpm, the following doses displayed in table 5 were measured with 6 lamps:

TABLE 5

| mL/min | UV-dose 2.5/cm mJ/cm$^2$ | UV-dose 4.5/cm mJ/cm$^2$ |
| --- | --- | --- |
| 288.0 | 24.51 | not done |
| 230.4 | 29.83 | 17.07 |
| 172.8 | 38.49 | 20.79 |
| 115.2 | 55.27 | 30.60 |
| 86.4 | 70.25 | 41.58 |
| 57.6 | 100.28 | 58.57 |
| 36.8 | 138.31 | 71.97 |

Figure 7:
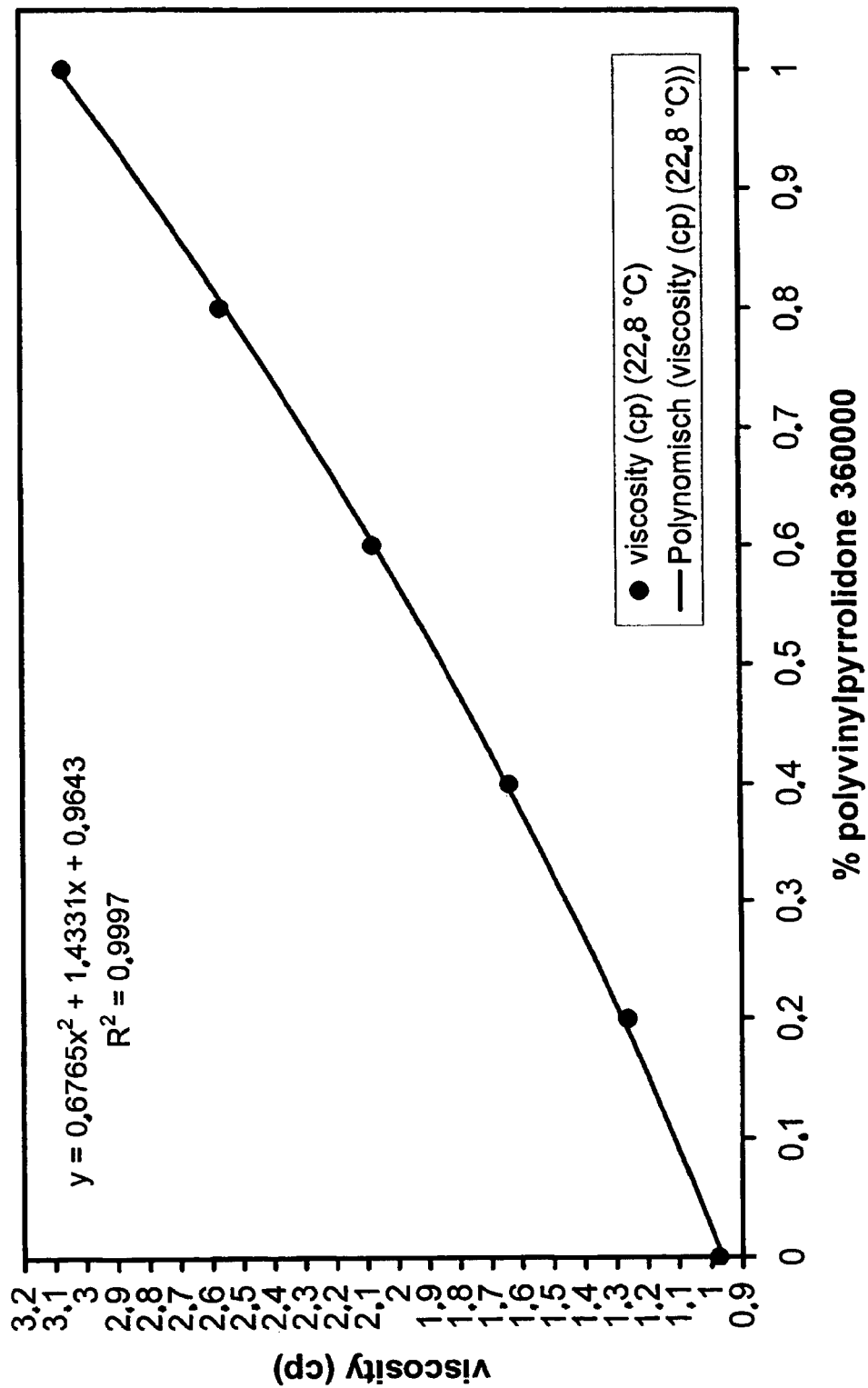
FIG. 7 depicts the non-linear relationship between increase in viscosity and polyvinylpyrrolidone concentration (cf. Example 10).

The correlation between residence time (=1/flow rate) and dose is not linear, which indicates the actively increased residence time dispersion (as depicted in U.S. Pat. No. 6,576,201, FIG. 7) at low flow rates and high rotation rates.

The model solution of Example 2 ($a_{253.7}$=10/cm, h=1.25 cp) was pumped through the cell and illuminated with 6 lamps with the flow rate kept constant while the inner cylinder rotation rate was changed. The results are displayed in Table 6.

TABLE 6

| rpm Taylor cell | UV dose (mJ/cm$^2$) at 48 mL/min | UV dose (mJ/cm$^2$) at 67.2 mL/min |
| --- | --- | --- |
| 45 | 29.51 | 23.47 |
| 60 | 32.09 | 23.67 |
| 75 | 31.69 | 22.47 |
| 90 | 31.41 | 25.72 |
| 105 | 31.59 | not done |

The model solution of Example 2 ($a_{253.7}$=7.5/cm, □=1 cp) was pumped through the cell and illuminated with 6 lamps with the flow rate kept constant at 192 mL/min while the rotation rate was changed. The bacteriophage-spiked albumin solution as described in Example 3 was then irradiated and the bacteriophage titer determined. The results are displayed in Table 7.

TABLE 7

| rpm Taylor cell | UV dose (mJ/cm$^2$) | log$_{10}$ pfu Phi-X 174/mL |
| --- | --- | --- |
| unirradiated | 0.00 | 6.85 |
| 30 | 10.41 | not done |
| 60 | 11.12 | 4.60 |
| 90 | 11.12 | 4.48 |
| 120 | 10.98 | 4.89 |
| 150 | 11.25 | 4.94 |
| 180 | 10.90 | 4.84 |

TABLE 7-continued

| rpm Taylor cell | UV dose (mJ/cm$^2$) | log$_{10}$ pfu Phi-X 174/mL |
| --- | --- | --- |
| 240 | 10.89 | 4.98 |
| 300 | 10.90 | 5.08 |

The same model solution was pumped through the Taylor cell at varying flow rates and a constant rotation rate of 60 rpm. The dose was measured and a linear correlation with the residence time was obtained. The bacteriophage-spiked albumin solution as described in Example 3 was then irradiated and the bacteriophage titer determined. The average lamp intensity of he six lamps was measured during the dosimetry and the phage irradiation to calculate the radiometric correction factor. The results are displayed in Table 8.

TABLE 8

| | mW/cm$^2$ | | | | | | |
| --- | --- | --- | --- | --- | --- | --- | --- |
| | lamp 1 | lamp 2 | lamp 3 | lamp 4 | lamp 5 | lamp 6 | avg. |
| dosimetry | 12.96 | 10.42 | 10.95 | 14.85 | 11.59 | 13.30 | 12.35 |
| phages | 13.20 | 10.73 | 11.05 | 15.18 | 11.70 | 13.03 | 12.48 |

The radiometric correction factor, by which the doses determined at the dosimetry had to be multiplied to calculate the doses effective during the bacteriophage irradiation, was determined to be 1.011.

TABLE 9

| flow rate (mL/min) | residence time (min/mL) | UV dose (mJ/cm$^2$) dosimetry | UV dose (mJ/cm$^2$) phages | log$_{10}$ pfu Phi-X 174/mL | inactivation □log$_{10}$ pfu/mL |
| --- | --- | --- | --- | --- | --- |
| unirradiated | | 0.00 | 0.00 | 7.29 | 0.00 |
| 153.6 | 0.00651 | 12.75 | 12.89 | 4.65 | −2.64 |
| 192 | 0.00521 | 10.24 | 10.36 | 5.05 | −2.24 |
| 259.2 | 0.00386 | 7.65 | 7.73 | 5.35 | −1.93 |
| 384 | 0.00260 | 5.11 | 5.17 | 5.86 | −1.43 |
| 768 | 0.00130 | 2.28 | 2.31 | 6.51 | −0.78 |

From the corresponding bacteriophage titers displayed in Table 9 it can be seen that a dose-dependent inactivation rate of approximately −0.2 (log$_{10}$ pfu/mL)/(mJ/cm$^2$) is achieved.

A similar experiment was done with a model solution ($a_{253.7}$=2.6/cm, □=1 cp) and only 2 lamps. Then a bacteriophage-spiked albumin solution with the same absorption and viscosity was irradiated. The radiometric correction factor (bacteriophage solution/dosimetry) was 0.988. The results are displayed in Table 10.

TABLE 10

| flow rate (mL/min) | residence time (min/mL) | UV dose (mJ/cm$^2$) dosimetry | UV dose (mJ/cm$^2$) phages | log$_{10}$ pfu Phi-X 174/mL | inactivation Dlog$_{10}$ pfu/mL |
| --- | --- | --- | --- | --- | --- |
| unirradiated | | 0.00 | 0.00 | 7.00 | 0.00 |
| 153.6 | 0.00651 | 14.68 | 14.50 | 3.46 | −3.54 |
| 192 | 0.00521 | 11.90 | 11.75 | 3.79 | −3.21 |
| 259.2 | 0.00386 | 8.83 | 8.72 | 4.45 | −2.55 |
| 384 | 0.00260 | 6.06 | 5.99 | 5.11 | −1.89 |
| 768 | 0.00130 | 3.06 | 3.02 | 5.90 | −1.10 |

A similar experiment at a constant flow rate of 192 mL/min and a variable inner cylinder rotation rate was done with a bacteriophage-spiked albumin solution ($a_{253.7}$=4.5/cm, η=1.05 cp) based on a dosimetry with the corresponding model solution. Here, an additional sample was drawn from the front volume leaving the cell (which has a lower dose due to its shorter residence time). The results are displayed in Table 11.

TABLE 11

| rpm Taylor cell | UV dose (mJ/cm$^2$) | log$_{10}$ pfu Phi-X 174/mL | Inactivation (Dlog$_{10}$ pfu/mL) |
|---|---|---|---|
| unirradiated | 0.00 | 6.82 | 0.00 |
| 60 (start) | 16.79 | 2.98 | −3.84 |
| 60 | 18.40 | 2.55 | −4.27 |
| 90 | 18.22 | 3.03 | −3.80 |
| 120 | 18.06 | 3.64 | −3.19 |
| 150 | 17.99 | 3.74 | −3.08 |
| 180 | 18.22 | 3.91 | −2.91 |
| 240 | 18.10 | not done | |
| 300 | 18.24 | not done | |
| 30 | 18.70 | not done | |

From the results obtained by the combination of chemical and biological dosimetry it can be seen that the residence time dispersion (as depicted in U.S. Pat. No. 6,576,201, FIG. 7) can be measured by a combined application of these methods.

EXAMPLE 6

Validation of Batch Reactors Using Chemical Dosimetry, Biodosimetry, and Radiometry A large-scale microorganism inactivation photoinactivation reactor, having a cylindrical quartz tube (25 cm inner diameter, 5 mm wall thickness, 75 cm length), a flat top lid and a bulged bottom milled from stainless steel and equipped with filling and sampling ports, and a stacked propeller stirrer with three three-blade propellers and a wiper blade at each outer blade edge, was surrounded with 10 water-thermostated UV-C-lamps (Philips TUV 55W HO) mounted in lamp boxes as described in Example 18, with each lamp monitored with a Dr. Groebel UVC-SE radiometer sensor. The maximum capacity of this reactor is 30 L. The lamp power was recorded using a radiometer sensor for each lamp on a chart recorder, and the relative lamp power normalized to the first run set as 100%.

In the 30 L photoinactivation reactor, albumin solution spiked with bacteriophage Phi X 174 ($a_{253.7}$=7.1/cm, η=1.05 cp) was irradiated after a dosimetry calibration with a model solution of the same absorbance and viscosity. A stirring speed of 90 rpm was set. A dose rate of 1.1634 mJ/cm$^2$ had thus been determined, and bacteriophage inactivation samples were drawn every 2 min 8 s up to 17 min 4 s, i.e. at dose increments of 2.48 mJ/cm$^2$ up to a target dose of 20 mJ/cm$^2$. Samples were simultaneously drawn at a bottom and a top sampling port to investigate the homogeneity of mixing. The results are displayed in Table 12.

TABLE 12

| UV dose (mJ/cm$^2$) | log$_{10}$ pfu/mL (top) | log$_{10}$ pfu/mL (bottom) |
|---|---|---|
| 0.00 | 7.84 | 7.87 |
| 2.48 | 6.85 | 6.69 |
| 4.96 | 5.91 | 5.79 |
| 7.45 | 4.61 | 4.79 |
| 9.93 | 3.51 | 3.82 |
| 12.41 | 2.98 | 2.98 |

TABLE 12-continued

| UV dose (mJ/cm$^2$) | log$_{10}$ pfu/mL (top) | log$_{10}$ pfu/mL (bottom) |
|---|---|---|
| 14.89 | 2.09 | 1.93 |
| 17.38 | (1.00) | (1.19) |
| 19.86 | (0.05) | (0.35) |

From the bacteriophage titers >10 pfu/0.9 mL a top inactivation rate of −0.3940 log$_{10}$ (pfu/mL)/(mJ/cm$^2$) and a bottom inactivation rate of −0.3912 log$_{10}$ (pfu/mL)/(mJ/cm$^2$) were determined. An average dose-dependent inactivation rate of −0.3926 log$_{10}$ (pfu/mL)/(mJ/cm$^2$) indicates a good homogeneity and an effective mixing, and a narrower dose-distribution compared with the flow-through inactivation rates of −0.3369 log$_{10}$ pfu/(mJ/cm$^2$) in Example 3 and of approximately −0.2 log$_{10}$ pfu/(mJ/cm$^2$) in Example 4. Compared to the un-attenuated bacteriophage inactivation rate of −0.44 log$_{10}$ pfu/(mJ/cm$^2$) the batch irradiation shows the most homogeneous and uniform exposure of the microorganisms to the UV-C light due to the most effective mixing.

A laboratory-scale microorganism inactivation photoinactivation reactor, consisting essentially of a cylindrical quartz vessel (7 cm inner diameter, 3 mm wall thickness, 13 cm in height) with a flat plastic top lid with sampling ports and a bulged plastic bottom, and equipped with a stacked impeller stirrer with near-wall wiper blades (2 impellers, adjustable stirring speed), was illuminated from the side with two 10 W low-pressure mercury lamps. The maximum capacity of this reactor is 450 mL. The lamp intensity was recorded by a digital dual sensor-radiometer (Dr. Groebel UV-Elektronik RM21 with UVC-SE sensors) on a computer. The dose increment during the biodosimetry irradiation was calculated from the multiplication of the lamp dose increment in the biodosimetry sampling time interval times by the chemical dosimetry dose rate and division of the result by the lamp dose rate obtained during the dosimetry calibration.

In the 450 mL photoinactivation reactor, the same bacteriophage-spiked antitrypsin solution as in Example 3 was irradiated after a dosimetry calibration with the same model solution as in Example 2 had been done. The dose rate was 2.5989 (mJ/cm$^2$)/min, and samples were drawn every 1 min 1 s up to 8 min 8 s. The elastase inhibiting activity at a dose of 20 mJ/cm2 was 97% of the unirradiated solution. The results are displayed in Table 13.

TABLE 13

| UV dose (mJ/cm$^2$) | log$_{10}$ pfu Phi-X 174/mL | Δlog$_{10}$ pfu Phi-X 174/mL |
|---|---|---|
| 0.00 | 7.28 | 0.00 |
| 1.83 | 6.11 | −1.17 |
| 4.45 | 5.02 | −2.26 |
| 7.02 | 4.01 | −3.27 |
| 9.65 | 2.80 | −4.48 |
| 12.24 | 1.75 | −5.53 |
| 14.87 | (0.82) | −6.46 |
| 17.46 | (0.00) | −7.28 |
| 20.05 | (0.00) | −7.28 |

A dose-dependent inactivation rate of −0.4406 log$_{10}$ (pfu/mL)/(mJ/cm$^2$) indicates a good homogeneity and an effective mixing, and a narrow dose-distribution apparently effects a reduction of −5.53 log$_{10}$ pfu/mL even at 12.24 mJ/cm$^2$ compared with 17.34 mJ/cm$^2$ in the flow-through method described in Example 3.

EXAMPLE 7

Determination of an Absorption-Dependent Irradiation Source Target Light Sum Dose of the 30 L Reactor by the Combined Use of Chemical Dosimetry and Radiometry to Ensure a Lamp-Failure Safe Robust Process The 30 L reactor described in Example 5, but equipped with 9 individually switchable thermostated lamps with reflectors, was validated with 10 different model dosimetric solutions and 4 lamps ($a_{253.7}$=3/cm to 12/cm in 1/cm increments, ☐=1.15 cp) to determine the effective dose rate (in (mJ/cm2)/min, the irradiating light dose rate (in (mJ/cm2)/min, and the irradiation time necessary for an effective dose of 20 mJ/cm2. The irradiation intensity of the lamps was monitored with electronic radiometers and recorded with a chart recorder, and a sum counter was installed to sum up the signals from all radiometers during the irradiation. The absorption-dependent irradiation source light sum dose is calculated as the radiometer sum signal increase with the irradiation time. The irradiation light dose rate is orders of magnitudes higher than the chemical dose rate, because the radiometer sensors receive the UV light practically unattenuated by any absorbing medium. The irradiation time for a given target dose effective in the solution, e.g. 20 mJ/cm2, is multiplied by the irradiation light dose rate to calculate the absorption-dependent irradiation source target light sum dose as the irradiation parameter. The results are displayed in Table 14.

TABLE 14

| Absorption coefficient $\alpha_{253.7}$ (1/cm) | Absorption-dependent irradiation source light sum dose $H_{lamp}$ for 20 mJ/cm$^2$ |
| --- | --- |
| 3 | 13393 |
| 4 | 18204 |
| 5 | 25230 |
| 6 | 29942 |
| 7 | 33770 |
| 8 | 38310 |
| 9 | 43704 |
| 10 | 48085 |
| 11 | 54620 |
| 12 | 60027 |

From Table 14 it can be seen that the absorption-dependent irradiation source light sum dose of the lamp correlates in a linear relation with the absorbance, expressed by the formula $H_{lamp}$=5058.9×$a_{253.7}$−1413 with a correlation $R^2$=0.9972 close to unity. The absorbance-dependent irradiation source target light sum dose, which itself is independent of any change in intensity, is therefore the ideal parameter for a robust irradiation process to ensure that the appropriate target dose has been applied. The irradiation process is controlled by the absorption-dependent irradiation source light sum dose in a way that upon attaining this pre-determined absorption-dependent irradiation source target light sum dose, which is interpolated to every absorbance in the validation range, the lamps are turned off to terminate the irradiation.

EXAMPLE 8

Simulation of Lamp Failure During the Absorption-Dependent Irradiation Source Target Light Sum Dose-Controlled Irradiation Process and Demonstration of the Correct Applied Target Dose Effective in the Solution A model solution ($a_{253.7}$=8/cm, ☐=1.15 cp) was irradiated in the 30 L reactor as described in Example 5. Two experiments were done in which after 10 min one of the four lamps was switched off and either replaced by turning on a different lamp, or not by continuing and terminating the irradiation only with 3 lamps. The irradiation light dose rates were determined by chemical dosimetry, and upon attaining the absorption-dependent irradiation source target light sum dose $H_{lamp}$=39058 mJ/cm$^2$ as calculated from the formula in the validation described in Example 6, the lamps were turned off, and a sample was drawn to determine the dose effective in the solution.

In the first experiment with the replacement of the lamp after 10 min with another lamp, the absorption-dependent irradiation source light sum dose was reached after 16 min 43 s, and a dose of 19.7 mJ/cm$^2$ was measured in the model solution. In the second experiment without lamp replacement, the absorption-dependent irradiation source light sum dose was reached after 19 min 55 s, and a dose of 19.9 mJ/cm$^2$ was measured in the model solution.

From the effective doses measured after the irradiation time, which was required to attain the pre-determined absorption-dependent irradiation source target light sum dose, it can be seen that the absorption-dependent irradiation source target light sum dose-controlled process is even insensitive and robust against failure of a lamp during the irradiation process, because the absorption-dependent irradiation source target light sum dose ensures the application of the correct effective dose.

EXAMPLE 9

Adjustment of Model Solutions to Match the Absorption and the Turbidity of Turbid Fluids with High and Low Molecular Absorbance Naturally turbid apple cider was filtered through a 0.22 μm syringe filter. The absorbance of the unfiltered cider at 253.7 nm was 18/cm, while the filtered clear cider had only 10.4/cm, both with a viscosity of 1.25 cp.

To a iodide/iodate/PVP model solution matching the absorbance and the viscosity of the filtered cider ($a_{253.7}$=10.4/cm, ☐=1.25 cp), bentonite was added to match the turbidity of the turbid cider. A concentration of 2 g bentonite was found to add the turbidity of 7.6/cm. The results are displayed in Table 15.

TABLE 15

| bentonite g/L | $a_{253.7}$/cm |
| --- | --- |
| 0 | 10.4 |
| 0.1 | 11.0 |
| 0.2 | 11.5 |
| 0.3 | 11.9 |
| 0.4 | 12.3 |
| 0.5 | 12.5 |
| 0.75 | 13.3 |
| 1.0 | 15.6 |
| 1.5 | 17.0 |
| 2.0 | 18.0 |
| 2.5 | 18.4 |

Figure 5:
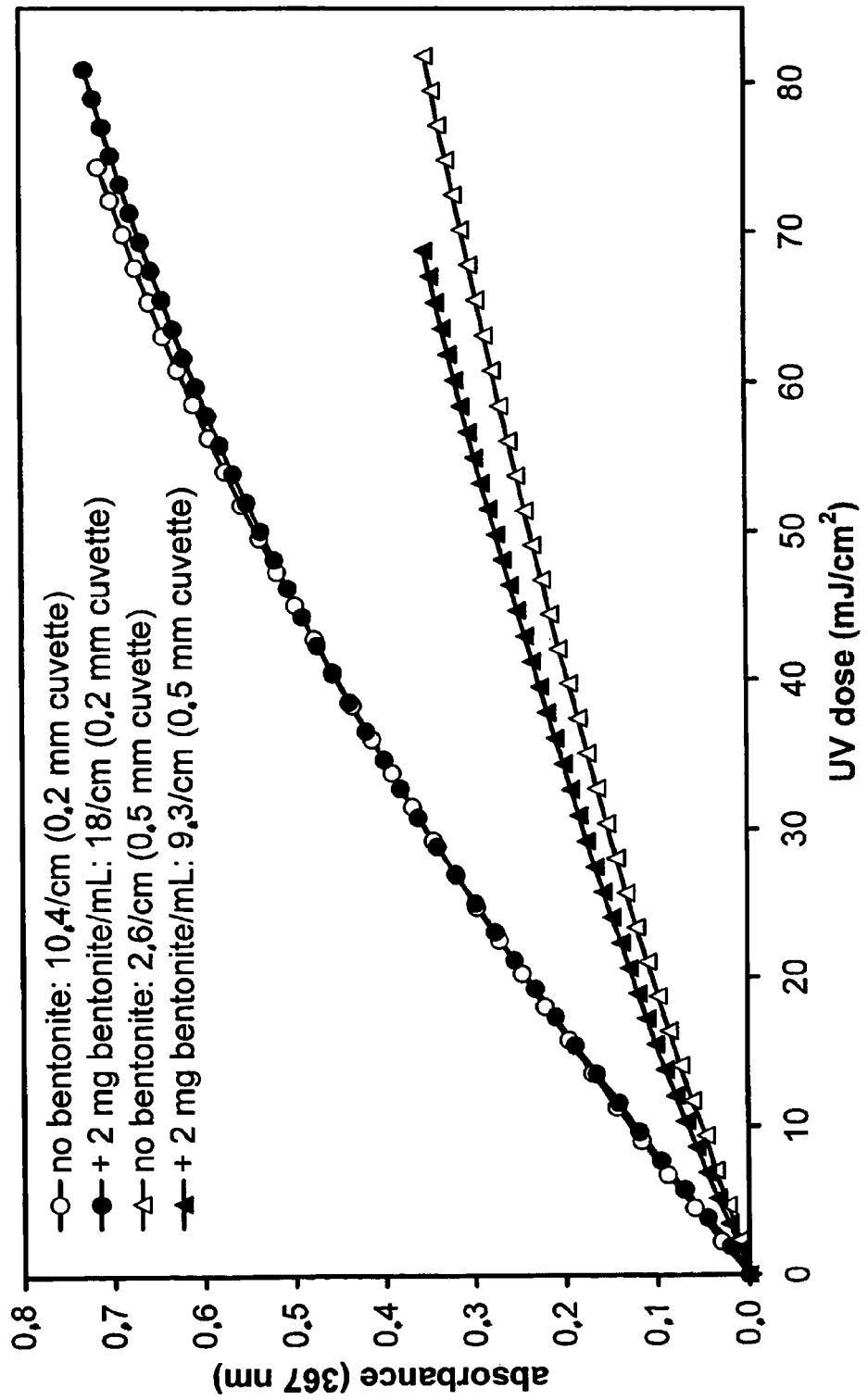
FIG. 5 depicts the calibration plots for model solutions with defined molecular absorbance and the same solutions with 2 g bentonite/L to add turbidity from suspended particles (cf. Example 10).

The calibration plots as depicted in FIG. 5 showed only a slight decrease in sensitivity with the turbid solution, for which the Morowitz correction factor (Morowitz 1950) for both absorbance and turbidity had been applied. For a solution with an absorption coefficient of 2.6/cm and a viscosity of 1 cp (=1.543 g PVP K25/L), 2 g bentonite/L were added to achieve a total absorbance of 9.3/cm. As seen from FIG. 5, there was also no relevant difference in the calibration plot. 100 mL of the clear and the turbid model solutions were irradiated in a stirred 4 cm quartz test tube inserted into the same lamp housing as described in Example 5 to be illuminated with 2 facing lamps or 1 lamp. Samples of 1 mL were drawn every 4 minutes during the irradiation time of 40 min. The lamp intensities were recorded during each irradiation, with the second irradiation of the 18/cm solution having the 1.0416-fold lamp intensity of the first irradiation of 10.4/cm solution, and the second irradiation of the 9.3/cm solution having the 0.9928-fold lamp intensity of the first irradiation of the 2.6/cm solution The dose rates theoretically depending on the inverse absorption coefficient 1/a did not show the expected difference of 100% for 10.4/cm and 57% for 18.0/cm or 100% for 2,6/cm and 28% for 9.3/cm, but instead the difference was (with 2 lamps) 1.748 (mJ/cm$^2$)/min for 10.4/cm and 1.603 (mJ/cm$^2$)/min divided by 1.0416=1.539 (mJ/cm$^2$)/min for 18.0/cm, i.e. 88% for the turbid solution with the high molecular absorbance, and (with 1 lamp) 3.415 (mJ/cm$^2$)/min for 2.6/cm and 1.854 (mJ/cm$^2$)/min divided by 0.9928=1.868 (mJ/cm$^2$)/min, i.e. 55% for the turbid solution with the low molecular absorbance. This demonstrates that the additional turbidity scatters the light into the solution, which is measurable by chemical dosimetry.

EXAMPLE 10

Figure 6:
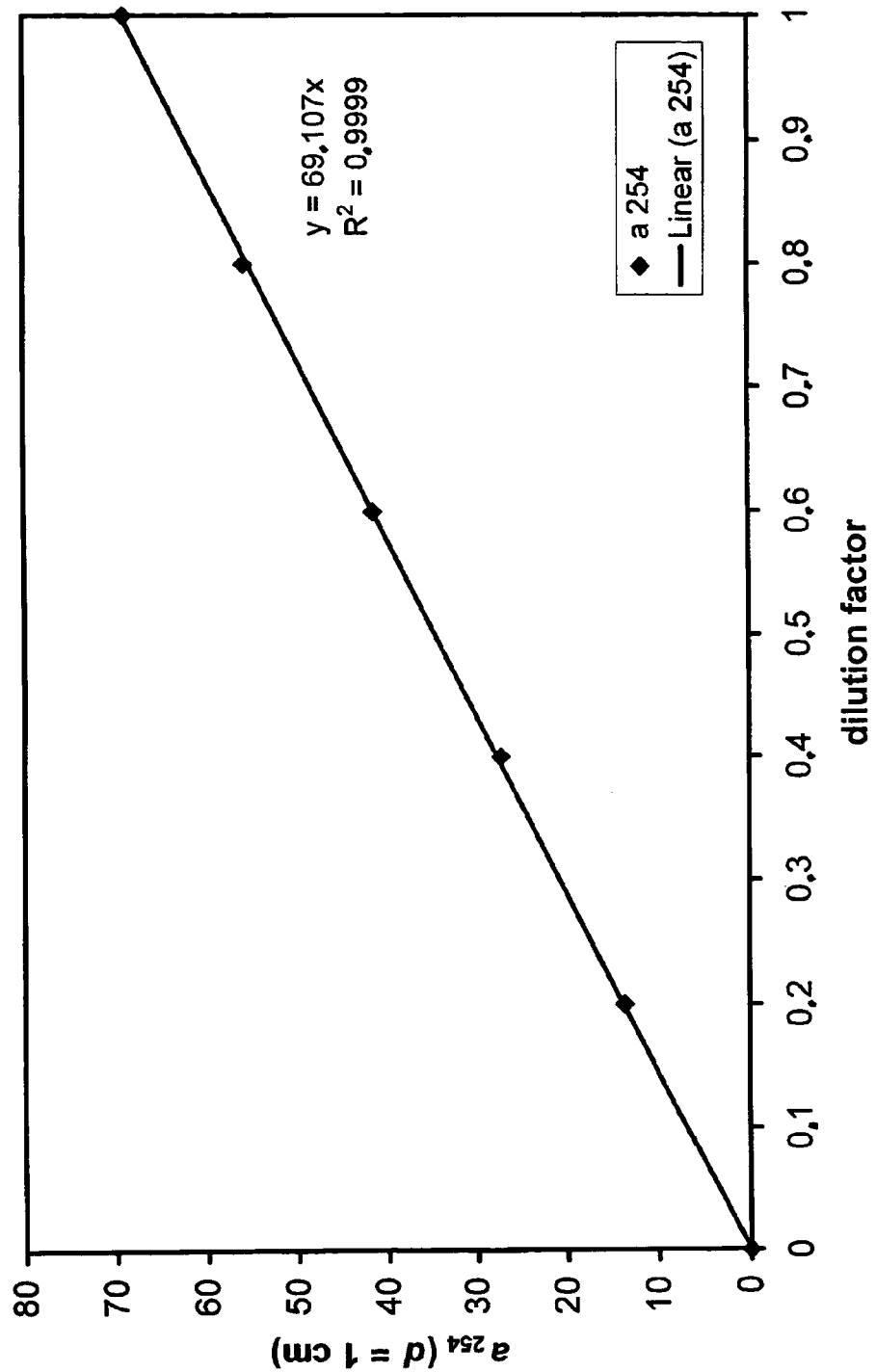
FIG. 6 depicts the linear relationship between an absorption coefficient and concentration (cf. Example 10).

Absorption Coefficients of the Iodide/Iodate Actinometer Solution at High Dilution, Dosimetric Response of the Iodide/Iodate Actinometer Solutions, and Stabilization of the UV-C Generated Tri-Iodide by Polyvinylpyrrolidone A solution containing 0.24 M KI and 0.04 M in 0.01 M borate buffer, pH=9.25, was diluted 0.2-, 0.4-, 0.6- and 0.8-fold with 0.01 M borate buffer and the absorption measured in a 0.1 mm cuvette. FIG. 6 shows that the absorption coefficient depends in a linear ratio ($a_{253.7}$=69/cm×dilution factor) on the concentration.

A solution containing 10 g polyvinylpyrrolidone K90 (PVP K90; average molar mass 360000 Da) in 1 L 0.01 M borate buffer was diluted 0.2-, 0.4-, 0.6-, 0.8-fold and the viscosity of the dilutions and the buffer were measured in a Schott 0.40 mm Ubbelohde capillary viscosimeter thermostated at 22.8° C. It can be seen from FIG. 7 that the viscosity increases with the concentration in a non-linear ratio.

Figure 8:
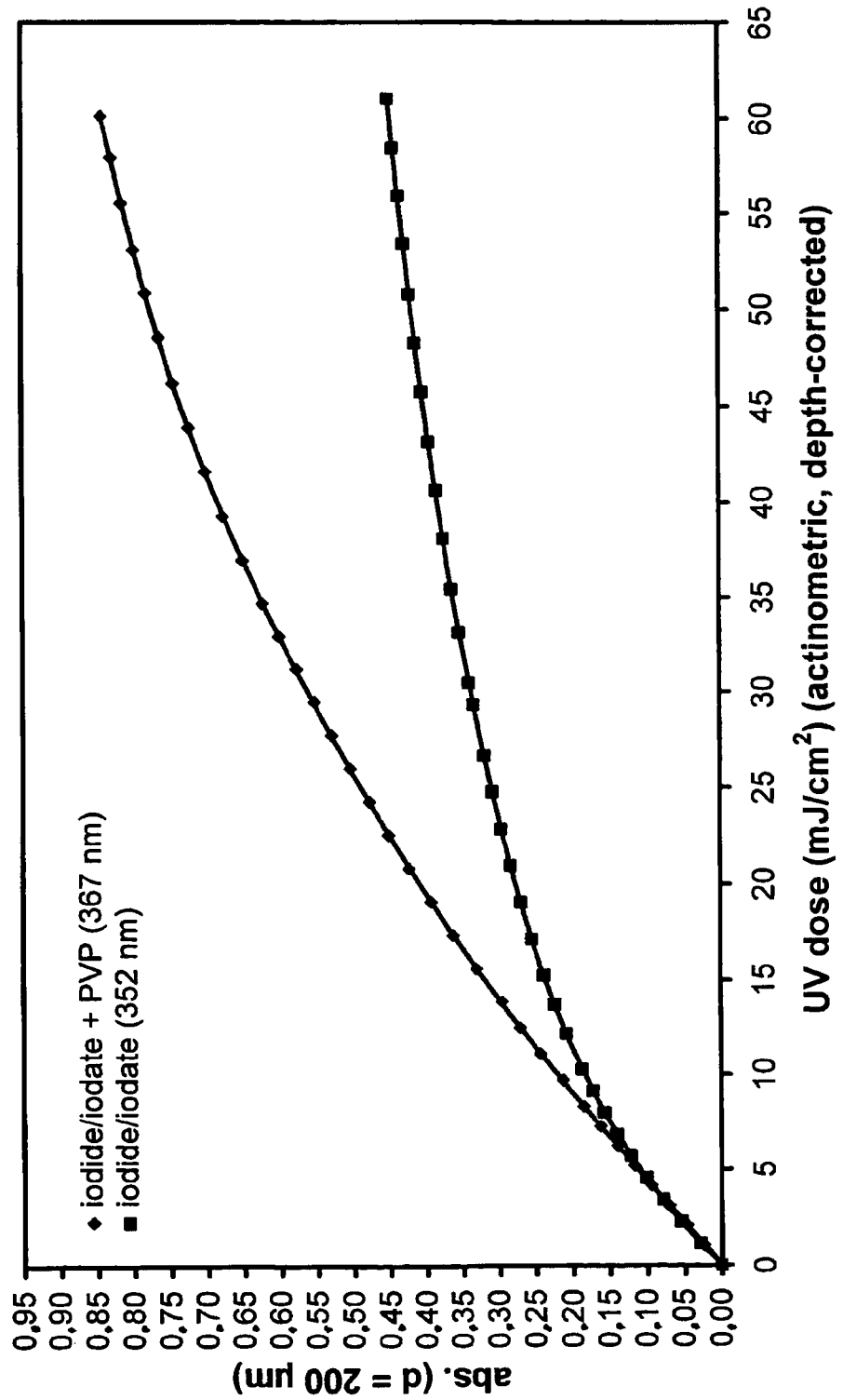
FIG. 8 depicts the increase in absorbance with applied surface dose, and increase in sensitivity with KI/KIO3 concentration (cf. Example 10).

Dilutions of the stock solution containing 0.24 M KI and 0.04 M in 0.01 M borate buffer, pH=9.25, were prepared to a defined absorption at 253.7 nm of 6.1/cm (0.0212 M KI+0.0035 M KIO$_3$+0.95 g PVP K90/L; for prothrombin complex eluate from DEAE sephadex anion exchange gel (Brummelhuis 1980) and 16/cm (0.06 M KI+0.01 M KIO$_3$+ 6.25 g PVP K90/L; for a 2.5% (w/v) fibrinogen solution), and filled into the 0.2 mm cuvettes. The thin-layer calibration was done by placing the cuvette filled with the dosimetry solution for a defined time under a CAMAG TLC lamp with a known irradiance (measured with the Rahn actinometer) at the cuvette position. The absorbance was measured at 367 nm. From FIG. 8 it can be seen that the absorbance increases with the applied surface dose, and that the sensitivity increases with the KI/KIO$_3$ concentration.

Figure 9:
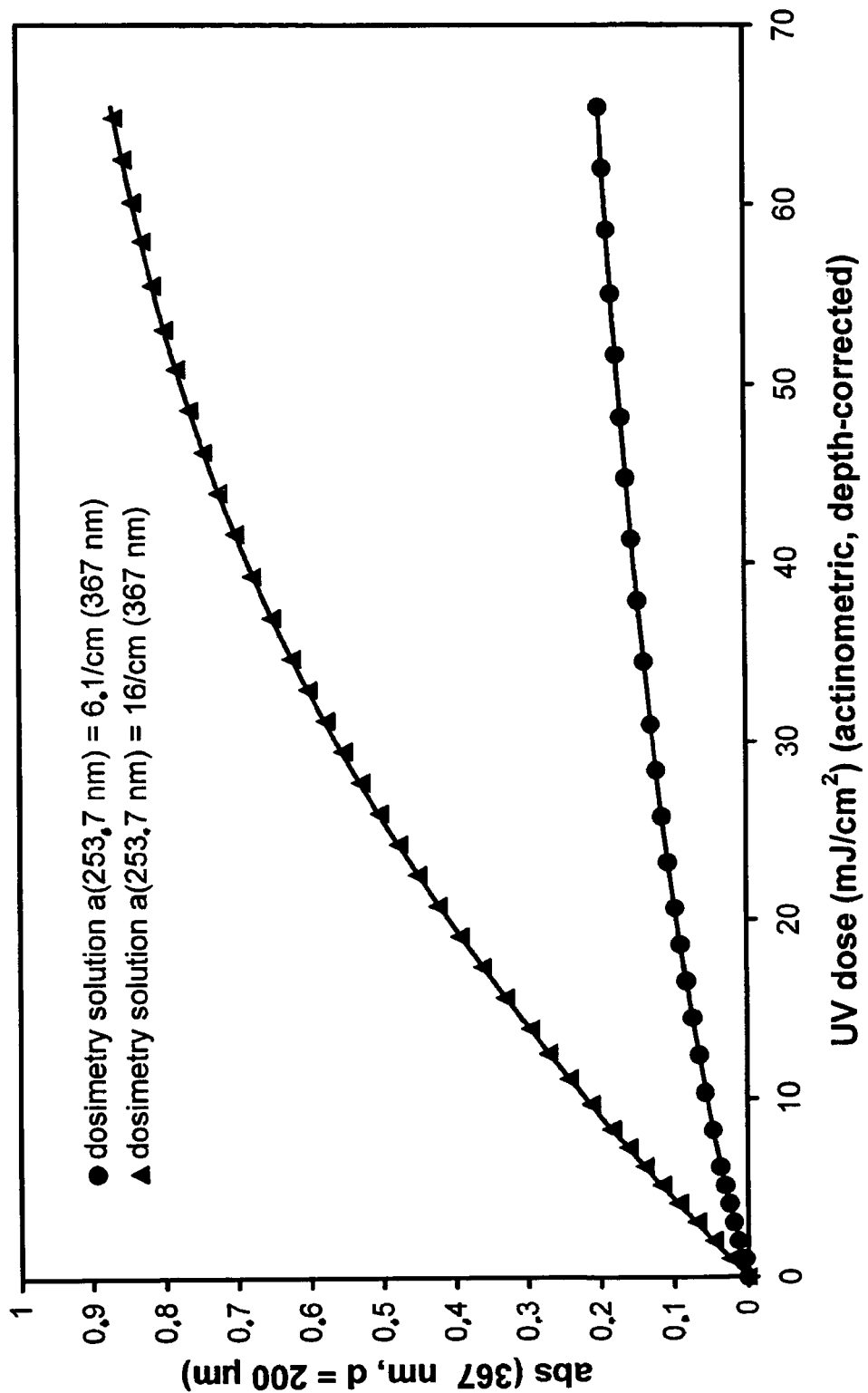
FIG. 9 depicts the sensitivity improvement with PVP (cf. Example 10).

A dosimetry solution containing 0.06 M KI and 0.01 M KIO$_3$ in 0.01 M borate buffer, pH=9.25, with an absorption coefficient of $a_{253.7}$=16/cm, and a solution with the same KI and KIO$_3$ concentration and 6.25 g polyvinylpyrrolidone (PVP) K 90/L were prepared. The thin-layer calibration was done by placing a 0.2 mm cuvette filled with the dosimetry solution for a defined time under the CAMAG TLC lamp as described above. The absorbance was measured at 352 nm (KI+KIO$_3$ only) or 367 nm (KI +KIO$_3$+PVP). From FIG. 9 it can be seen that PVP improves the sensitivity of the method.

EXAMPLE 11

Determination of the Irradiation Time in a Batch Photoinactivation Reactor with Fixed Geometry with Actinometric Dosimetry Solutions Dosimetry solutions with decadic absorption coefficients $a_{253.7}$ of 2.1/cm (0.0072 M KI+0.0012 M KIO$_3$+0.5 g PVP K90/L, for FVIII concentrate), 6.1/cm (see Example 10), 10/cm (0.0346 M KI+0.0058 M KIO$_3$+1.21 g PVP K90/L; for a 2% (w/v) immunoglobulin G solution), and 16/cm (see Example 10) were prepared and calibration plots recorded as described in Example 6. A quartz test tube 4 cm in diameter was filled with 100 mL dosimetry solution, stirred with a magnetic stirrer bar on a magnetic stirrer, and irradiated between 2 low-pressure mercury vapor lamps equipped with polished stainless steel reflectors. At predefined intervals, samples were drawn and filled into the 0.2 mm cuvettes for spectrophotometric measurement, and the dose was read out from the calibration plot. The dose-rate was then calculated as (mJ/cm$^2$)/min, and the inverse dose rate, i.e. the specific irradiation time per unit dose as min/(mJ/cm$^2$). The results are displayed in Table 16. The constant $k_1$ for the relation between the absorption coefficient and the (specific) irradiation time can be calculated:

$$t=k_1 \times a$$

TABLE 16

| solution $a_{253.7}$ = | 2.1/cm | 6.1/cm | 10/cm | 16/cm |
|---|---|---|---|---|
| dose-rate ((mJ/cm$^2$)/min) | 14.40 | 3.68 | 2.71 | 1.56 |
| Specific irradiation time (min/(mJ/cm$^2$)) | 0.0694 | 0.2714 | 0.3688 | 0.6410 |
| constant $k_1$ (average = 0.0386) | 0.0330 | 0.0445 | 0.0369 | 0.0401 |

By calculation of the linear regression of the specific irradiation-time depending on the absorption coefficient a linear correlation of $R^2$=0.989 is obtained. This result demonstrates that the dosimetry based on absorption- and viscosity-matching model solutions with thin-film calibration is suitable for the validation of stirred batch photoinactivation reactors.

EXAMPLE 12

Inactivation of MMV and Phi-X 174 in Thin Layer- and Batch Irradiation

MMV stock solution from cell culture supernatant (~10$^8$ tissue-culture infectious doses (TCID$_{50}$)/mL) and bacteriophage Phi-X 174 lysate (~1×10$^9$ plaque-forming units (PFU)/mL) from propagation in *Escherichia coli* were diluted in 20 mM phosphate-buffered 0.15 M NaCl (phosphate-buffered saline, PBS) and 2.5 mL were irradiated with different UV-C doses in 32 mm polystyrene petri dishes shaken horizontally under a CAMAG TLC lamp. The irradiance at the sample surface distance was determined with a Dr. Groebel RM21-radiometer with a daylight-blind UV-C sensor, and the self-absorbance of the solution measured in a spectrophotometer to correct for the effective fluence (UV dose) (Morowitz 1950). MMV and Phi-X 174 titers were determined by titration on host cell culture and host bacteria respectively. The results are displayed in Table 17.

TABLE 17

| UV dose (mJ/cm$^2$) | $\log_{10}$ pfu Phi-X 174/mL | UV dose (mJ/cm$^2$) | $\log_{10}$ TCID$_{50}$ MMV/mL |
|---|---|---|---|
| 0.00 | 6.41 | 0 | 6.54 |
| 2.25 | 5.79 | 2 | 5.31 |
| 4.50 | 4.37 | 4 | 4.42 |
| 6.75 | 3.46 | 6 | 3.52 |
| 9.00 | 2.36 | 8 | 2.93 |
| 11.25 | 1.35 | 10 | 2.37 |
|  |  | 12 | 1.44 |
| Inactivation rate | −0.468 $\log_{10}$(pfu/mL)/ (mJ/cm$^2$) |  | −0.405 $\log_{10}$(TCID$_{50}$/mL)/(mJ/cm$^2$) |

Into a 100 mL quartz bottle with a 4 cm stirrer bar 80 mL MMV- or Phi-X 174-spiked protein solution (prothrombin complex DEAE sephadex eluate, $a_{253.7}$=6.9/cm) were filled, placed on a magnetic stirrer, stirred at ~250 rpm, and irradiated from the side with a CAMAG TLC lamp. The calibration was done with a model solution ($a_{253.7}$=6.9/cm) as described in Example 11. Samples for virus or bacteriophage titration were drawn at time intervals calculated after the measured dose-rate and titrated to determine the titer of surviving infectious virus or bacteriophage. The results are displayed in Table 18.

TABLE 18

| UV dose (mJ/cm$^2$) | $\log_{10}$ (pfu Phi-X 174/mL) | UV dose (mJ/cm$^2$) | $\log_{10}$ (TCID$_{50}$ MMV/mL) |
|---|---|---|---|
| 0.00 | 7.27 | 0.00 | 6.77 |
| 1.69 | 5.96 | 6.86 | 3.46 |
| 3.37 | 5.52 | 13.70 | 0.61 |
| 5.06 | 4.78 |  |  |
| 6.74 | 3.95 |  |  |
| 8.42 | 3.11 |  |  |
| 10.10 | 2.39 |  |  |
| 11.79 | 1.28 |  |  |
| inactivation rate | −0.480 $\log_{10}$(pfu/mL)/ (mJ/cm$^2$) |  | −0.425 $\log_{10}$(TCID$_{50}$/mL)/(mJ/cm$^2$) |

From the inactivation rates of Phi-X 174 and MMV it can be deduced that their sensitivity to UV-C light at 253.7 nm is similar. Therefore Phi-X 174 was used as a biodosimeter. It can also be seen that the inactivation rates for the UV-C-absorbing liquid in the batch-stirred device are almost the same due to efficient method of mixing ensuring the transport of the microorganisms to the irradiation zone.

EXAMPLE 13

Use of Dosimetry and Biodosimetry for the Optimization of a Stirred Batch-Reactor The 450 mL batch reactor (7 cm inner diameter, 3 mm wall thickness, 13 cm in height) as described in Example 6 equipped with a stacked impeller stirrer (3 impellers, adjustable stirring speed) was illuminated from the side with two low-pressure mercury lamps, each mounted in an envelope of two concentric quartz tubes and equipped with a stainless steel reflector behind. Cooling water from a thermostat was pumped through the lamp envelope to keep the lamp temperature and the UV-C-output constant.

The stirring rate was adjusted to 60 rotations per minute (rpm) (slow stirring), 150 rpm (medium-fast stirring), and 240 rpm (fast stirring). The UV dose-rate for the irradiation of 450 mL absorption- and viscosity-matching model solution for bacteriophage-spiked prothrombin complex eluate ($a_{253.7}$=8.0/cm, $\square$=1.15 cp, 27.83 mM KI, 4.64 mM KIO$_3$, 1.3 g PVP K90/L in 0.1 M borate buffer, pH=9.25) was determined as described in Example 11. It was discovered that higher borate concentrations ($\geqq$0.1 M) than given in the literature (0.01 M) effect a higher sensitivity and a better stability of the dosimeter solution. The bacteriophage-spiked prothrombin complex eluate was irradiated and the bacteriophage inactivation determined as described in Example 12. As an additional parameter, the activity of coagulation factor X (FX) was measured using the amidolytic assay for doses of 0, 10, 15, 20, 25, 50, 75, and 100 mJ/cm$^2$. The results are displayed in Table 19.

TABLE 19

| stirring rate | 60 rpm | 150 rpm | 240 rpm |
|---|---|---|---|
| UV-C dose-rate (dosimetry) ((mJ/cm$^2$)/min) | 1.770 | 1.794 | 1.799 |
| Phi-X 174 inactivation rate (biodosimetry) ($\log_{10}$(pfu/mL))/(mJ/cm$^2$) | −0.277 | −0.399 | −0.460 |
| UV-C dose required to inactivate 5 $\log_{10}$(pfu/mL) | 18.05 | 12.53 | 10.87 |
| FX inactivation rate (U FX/mL)/(mJ/cm$^2$) | −0.0054 | −0.0048 | −0.0051 |
| FX inactivation at 20 mJ/cm$^2$ (% unirradiated) | 88 | 88 | 89 |

From this experiment, it can be seen that the optimization of a virus inactivation batch photoinactivation reactor can be done by model solution dosimetry and biodosimetry, because both methods of validation give information about the effectiveness of mixing. It is also evident that at the highest stirring rate possible for a protein solution (to avoid the generation of foam), the fastest microorganism inactivation will be achieved. The benefit of such an optimization is that with the most effective mixing, the safety margin for the virus inactivation at a target dose e.g. of 20 mJ/cm$^2$ is the highest, or the target dose can be reduced to conserve additional biological activity of the protein.

EXAMPLE 14

Validation and Process Monitoring for the Batch Irradiation of Prothrombin Complex Eluate Using Chemical Dosimetry, Biodosimetry, and Radiometry The 30 L virus inactivation photoinactivation as described in Example 6 with a stacked impeller stirrer with three three-blade impellers and a wiper blade at each outer blade edge, was surrounded with 10 water-thermostated UV-C-lamps (Philips TUV 55W HO) mounted in a thermostated lamp box as described in example 18, each monitored with a Dr. Groebel UVC-SE radiometer sensor. The lamp power was recorded using a radiometer sensor for each lamp on a chart recorder, and the relative lamp power normalized to the first run set as 100%.

29.5 L prothrombin complex eluate were spiked with 0.5 L Phi X-174 lysate (~4×10$^9$ pfu/mL) from *E. coli*. The resulting solution had an absorption coefficient of $a_{253.7}$=6.0/cm. The reactor dose-rate was determined prior to the virus inactivation experiments with an absorption- and viscosity-matching model solution as described in Example 11 containing 20.87 mM KI, 3.48 mM KIO$_3$, and 1.304 g PVP K90/L in 0.1 M borate, pH=9.25, with a dose rate of 1.3435 (mJ/cm$^2$)/min at a stirring speed of 90 rpm and a lamp dose rate relative to the first bacteriophage irradiation run of 98.5%. An irradiation time of 14 min had been determined for a target dose of 20 mJ/cm$^2$, and an essentially constant dose-rate was assumed. To demonstrate the effect of the lamp power as an error source, the lamp temperature was lowered for the third run from 28° C. to 24.5° C. to reduce the lamp power to about 90% of the maximum. The inactivation rate of Phi-X 174 (based on the assumed a constant dose rate) was determined as described in Example 12 and expressed as (log (pfu/mL))/(mJ/cm$^2$). The results are displayed in Table 20.

TABLE 20

|  | run No. 1 (=100%) | run No. 2 | run No. 3 |
|---|---|---|---|
| lamp power | 100% | 101.4% | 89.3% |
| Phi-X 174 inactivation rate k (uncorrected) | −0.4272 | −0.4331 | −0.3742 |
| Phi-X 174 inactivation rate, corrected for lamp power | −0.4272 | −0.4275 | −0.4190 |

It can be seen that the lamp power is a parameter of the batch irradiation process, and that both dosimetric dose-rates and biodosimetric inactivation rates have to be normalized to the lamp power.

EXAMPLE 15

Process Design for the Batch Irradiation of Protein Solutions Based on a Radiometric Target Dose Determined by Dosimetry and Radiometry The 450 mL photoinactivation reactor described in Example 6 was validated for the dose-rates and irradiation times for the irradiation of model solutions with absorption coefficient of 6.0/cm, 7.0/cm, 8.0/cm, 9.0/cm and 10.0/cm. A sample volume of 450 mL was stirred at 200 rpm. The lamps turned on and the dose rate was determined by the measurement of model solution samples drawn at 3, 6, 9, 12, 15, 18, 21, and 24 min. The lamp intensity was monitored and recorded by a dual-head radiometer connected to a computer.

Figure 10:
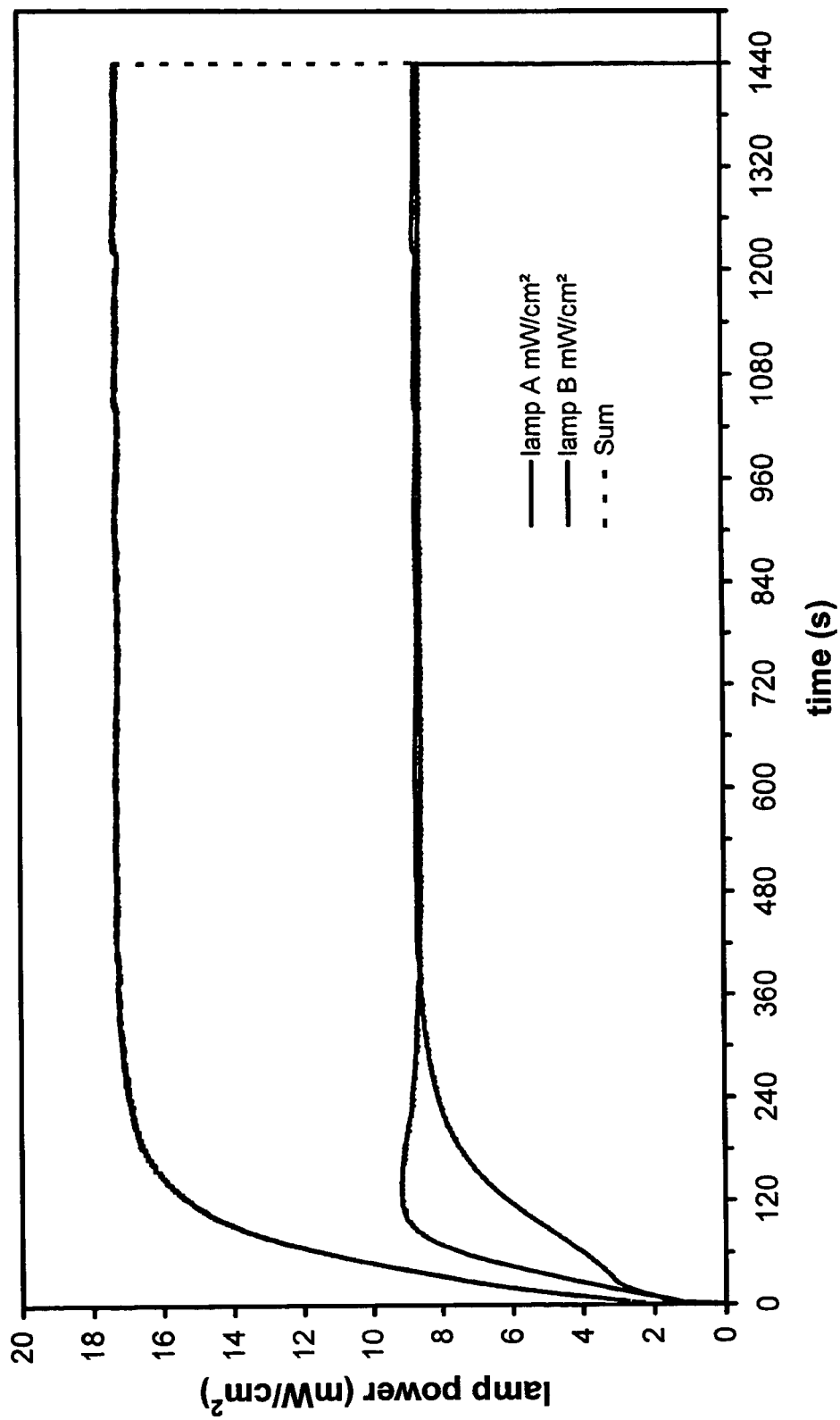
FIG. 10 depicts the lamp intensity changes (cf. Example 15).
Figure 11:
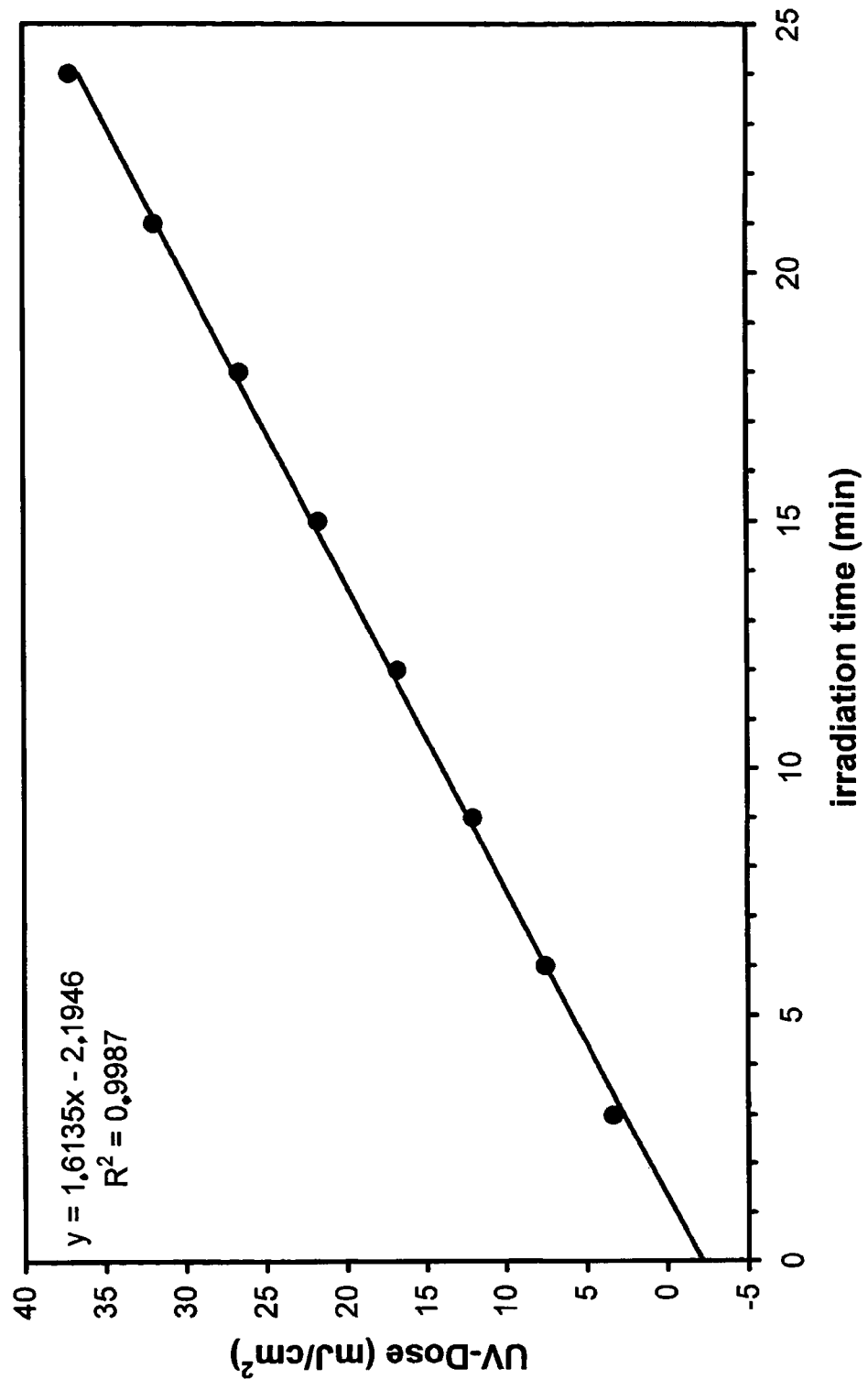
FIG. 11 depicts the dose-increase with error expressed as a y-axis constant (cf. Example 15).

FIG. 10 shows that the lamp intensity reaches its maximum 3 minutes after being turned on, and that the dose applied during the first 3 minutes is lower than the essentially constant dose-increase applied in the following 3 minute time-intervals. FIG. 11 shows the corresponding dose-increase with the error expressed as they-axis constant below zero. Therefore, the y-axis constant of the dose-rate equation was added to the target dose (20 mJ/cm$^2$) to obtain the corrected augmented target dose, the irradiation time calculated by dividing the augmented target dose by the dose-rate, and the lamp intensities measured in 1 second intervals (mW/cm$^2$) summed up over the irradiation time to obtain a target radiometric lamp dose (mJ/cm$^2$) depending on the absorption coefficient. The results are displayed in Table 21. The constant k$_2$ can be calculated:

$$Q = k_2 \times a$$

TABLE 21

| absorption coefficient $a_{253.7}$ | 6.0/cm | 7.0/cm | 8.0/cm | 9.0/cm | 10.0/cm |
|---|---|---|---|---|---|
| target radiometric lamp dose Q (mJ/cm$^2$) | 11879 | 13674 | 16038 | 18660 | 21102 |
| constant k$_2$ (average = 2024) | 1980 | 1953 | 2004 | 2073 | 2110 |

From the above table it can be seen that the radiometric target lamp dose increases with the absorption coefficient in a linear ratio (R$^2$=0.996).

EXAMPLE 16

Dosimetric Compensation for the UV-C Absorbing Effect of Ascorbate Tested as Protectant from Photodenaturation To FEIBA DEAE sephadex G50 eluate (18.2 mg protein/mL), sodium ascorbate was added to a concentration of 1 mmol/L. The absorption coefficient $a_{253.7}$ of the ascorbate-added FEIBA eluate was 16/cm compared to 7.3/cm for the native eluate.

For chemical dosimetry, model solutions containing 0.0254 M KI, 0.0042 M KIO$_3$ and 1.61 g PVP K90/L 0.1 M borate buffer, pH=9.25 (for $a_{253.7}$=7.3 cm) and 0.06 M KI, 0.01 M KIO$_3$ and 1.61 g PVP K90/L 0.1 M borate buffer, pH=9.25 (for $a_{253.7}$=16/cm) wer prepared, calibration plots were recorded with 0.2 mm thin-layer cuvettes, and 110 mL were irradiated in the batch photoinactivation reactor described in Example 11 with 1 lamp (for $a_{253.7}$=7.3/cm with a dose rate of 1.41 (mJ/cm$^2$)/min and 2 lamps (for $a_{253.7}$=16/cm with a dose-rate 1.33 (mJ/cm$^2$)/min). 110 mL of both the native FEIBA eluate and the ascorbate-added FEIBA eluate were irradiated at the respective dose-rate, and samples were drawn at 5; 10; 15; 20; 25; 30; and 35 mJ/cm$^2$. Factor X (FX) activity was determined as in Example 13. The results are displayed in Table 22.

TABLE 22

| UV dose (mJ/cm$^2$) | FX activity (% unirradiated) FEIBA native | FX activity (% unirradiated) FEIBA + 1 mM Na-ascorbate |
|---|---|---|
| 0 (unirradiated) | 100 | 100 |
| 5 | 94 | 101 |
| 10 | 95 | 93 |
| 15 | 86 | 98 |
| 20 | 89 | 91 |
| 25 | 84 | 85 |
| 30 | 85 | 89 |
| 35 | 84 | 88 |
| FX inactivation rate (U/(mJ/cm$^2$)) | −0.0045 (R$^2$ = 0.7886) | −0.0043 (R$^2$ = 0.7727) |

From the above table, it can be seen that there is no relevant difference in the FX inactivation rate (U FX/(mJ/cm$^2$)) between the native and the ascorbate-added FEIBA eluate. Therefore, ascorbic acid, which is itself highly UV-C absorbing, does not exert a photoprotective action on the FX protein. As demonstrated, such an increase by an additive in UV-C absorbance can be easily compensated by the described absorbance-matching chemical dosimetry.

EXAMPLE 17

Calibration of a Dosimeter Solution with an Lamp-Intensity- and Quantum Yield-Stabilized and Exposure Time-Controlled Calibration Device For reproducible and accurate exposure of a dosimeter solution in the thin-layer cuvette, a cuvette slot with a water-thermostated jacket was mounted onto the hinged back of a single lens reflex camera, and an aperture was milled into this back to expose the cuvette through the camera shutter. The camera's lens bayonet was mounted on the flange of a lamp housing containing a low-pressure mercury vapor lamp in a water-thermostated quartz glass jacket.

The lamp thermostating temperature was controlled with an externally circulating water thermostate to operate the lamp at its maximum UV-C output. The cuvette slot temperature was set within the range of the defined quantum yield of the iodide/iodate actinometer as given by Rahn (1997) and controlled with an externally circulating water cryostate. The camera shutter was set to 1 s exposure time and the shutter accuracy was determined using a photodiode connected to the microphone plug of a computer sound card. The shutter was found to maintain a constant exposure time of 1.000±0.002 s.

For the determination of the irradiance effective at the cuvette entrance window, the 0.6 M iodide/0.1 M iodate actinometer solution (Rahn 1997), which absorbs all incident photons completely, was filled into the 0.2 mm cuvette and exposed incrementally for 1, 2 and 3 s in the thermostated cuvette slot to ensure an essentially constant quantum yield. Before the exposure, the spectrophotometer absorbance at 352 nm was set to zero, and after each exposure step, the absorbance increase was measured in the spectrophotometer at 352 nm. From the absorbance increase, the concentration of triiodide, from the temperature-dependent quantum yield, the number of incident photons, and from the photon energy and the cuvette cross-sectional area, the irradiance E was calculated. E (in mW/cm$^2$) can thus be calculated from the absorbance increase Dabs at the exposure time t (in s), the cuvette surface A (in cm$^2$) and the cuvette volume V (in L), the extinction coefficient e at the optical path length d (264.5 for 0.01 cm), the energy W/einstein at 253.7 nm=471528 J, and the quantum yield $\Phi$=0.7545 at 21° C. (Rahn 1997), the according to the formula E=($\Delta$abs×V×W×1000)/(e×A×$\Phi$×t)×t). So after 1 s exposure time, an absorbance increase of 0.0392 corresponded to an irradiance of 0.9262 mW/cm$^2$, after cumulative 2 s, the cumulative absorbance increase of 0.0781 corresponded to 0.9227 mW/cm$^2$, and after 3 s, a cumulative absorbance increase of 0.1170 corresponded to 0.9215 mW/cm$^2$. The average irradiance was 0.9235 mW/cm$^2$ with a standard deviation of 0.0020 mW/cm$^2$, demonstrating a very precise exposure for calibration by the electronically controlled shutter.

A dosimeter solution corresponding to an UV-C absorbance of $a_{253.7}$=6.5/cm and a viscosity of 1.16 cp was filled into a 0.2 mm cuvette and exposed in 3 s increments up to 75 s. After every exposure increment, the absorbance increase at 367 nm was read out with the unirradiated solution as the blank. The obtained calibration plot correlated with a second-order equation where the absorbance at 367 nm depends on the exposure fluence H. The results are displayed in Table 23.

$abs$(367 nm, 0.2 mm)=$A \times H^2 + B \times H + C$

TABLE 23

| coefficient | |
|---|---|
| A | −0.0000257179 |
| B | 0.0074523297 |
| C | 0.0006009852 |
| correlation | |
| R$^2$ | 0.999986 |

The correlation R$^2$ close to unity indicates the precision of the calibration plot recorded by the means of an electronically controlled shutter. The second-order equation has the additional advantage that for an absorption value determined e.g. at the dose-rate measurement as described in Example 18, a plausible solution of this equation can be calculated easily. Calibration plots may also be segmented and such a second-order equation may be calculated for each segment to obtain a correlation R$^2$ as close to unity as possible. An example of such calibration device is provided in FIG. 12.

EXAMPLE 18

Temperature-Stabilization of an UV-Lamp as Usable in a Reactor Described in Examples 2, 4-6, 13, and 14

Figure 13:
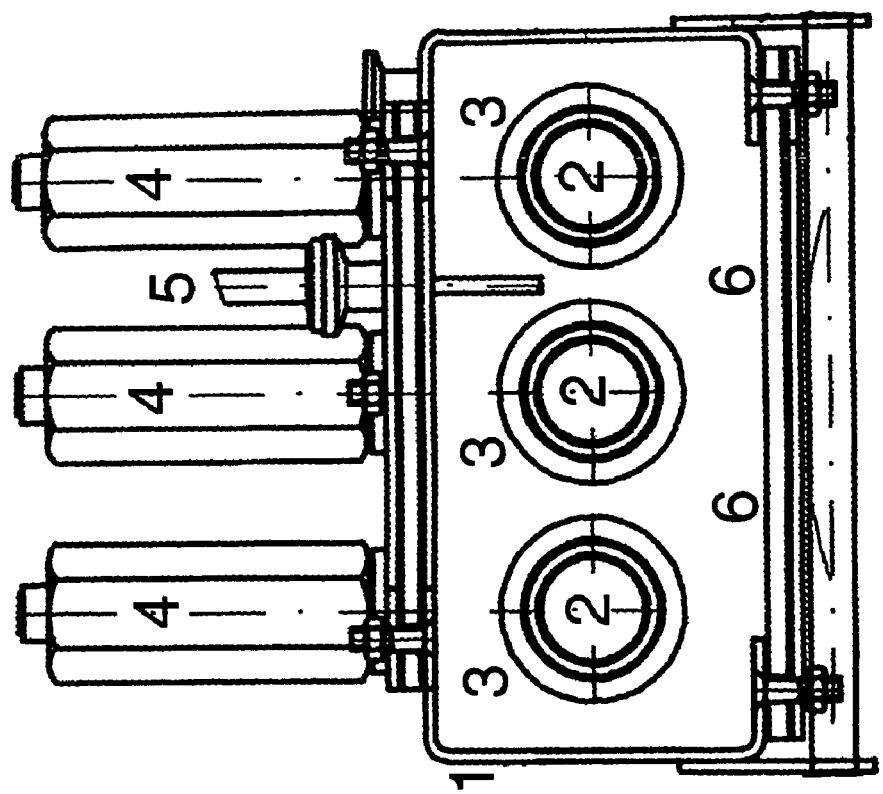
FIG. 13 depicts a cross-section of a thermostated lamp fixture with light intensity and temperature sensors (cf. Example 18).

Philips TUV55 HO lamps (55 W, 28 mm diameter, 900 mm length) were mounted in a lamp box (FIG. 13) with a stainless-steel housing (1) containing three lamps (2) in concentric thermostating envelope quartz glass tube (3), so that the thermostating water flows in the gap between the quartz glass envelope tube (3) and the stainless steel wall (1). Every lamp is monitored by a Dr. Groebel UVC-SE radiometer sensor (4) and the temperature is measured by a PT100 probe (5). At the front side of the steel housing there is a quartz glass window through which the UV-C light radiates onto the reactor vessel. The quartz tube had an inner diameter of 30 mm and a wall thickness of 3 mm. Water was pumped at a flow of 6 L/min from a circulating cryostat. The temperature was increased from 15 to 30° C. and the light intensity measured in ~0.5° C. intervals. The results are displayed in Table 24.

TABLE 24

| T (° C.) | E (mW/cm$^2$) |
|---|---|
| 15.1 | 6.585 |
| 15.6 | 6.675 |
| 16.1 | 6.755 |
| 16.6 | 6.795 |
| 17.1 | 6.905 |
| 17.6 | 6.955 |
| 18.1 | 7.045 |
| 18.6 | 7.075 |
| 19.1 | 7.120 |
| 19.6 | 7.175 |
| 20.2 | 7.235 |
| 20.6 | 7.275 |
| 21.1 | 7.295 |
| 21.6 | 7.345 |
| 22.1 | 7.385 |
| 22.6 | 7.400 |
| 23.1 | 7.420 |
| 23.6 | 7.425 |
| 24.1 | 7.435 |
| 25.1 | 7.405 |
| 25.6 | 7.470 |
| 26.1 | 7.435 |
| 26.6 | 7.455 |
| 27.1 | 7.465 |
| 27.6 | 7.450 |

TABLE 24-continued

| T (° C.) | E (mW/cm$^2$) |
|---|---|
| 28.1 | 7.450 |
| 28.6 | 7.435 |
| 29.1 | 7.405 |
| 29.6 | 7.390 |
| 30 | 7.370 |

The maximum intensity was attained at 27° C., which as a gentle temperature would not overheat the product, in contrast to direct thermostatization, where the cooling water temperature has to be around 40° C. By an increase of the air gap between the lamp surface and the inner tube of the thermostating envelope and the water flow rate, even lower temperatures can be effective in assuring the maximum lamp UV-C intensity. Around or next to such a thermostated lamp, every type of flow-through-reactor or batch reactor can be operated without the danger of product damage by heat, in particular by excessive heat.

REFERENCE LIST

Anderle H, Matthiessen H P, Spruth M, Kreil T, Schwarz H-P, Turecek P L: Assessment of the efficacy of virus inactivation by UV-C treatment of therapeutic proteins. Proceedings (CD-ROM) of the 2$^{nd}$ International Congress on Ultraviolet Technologies, International Ultraviolet Association, Vienna, Jul. 9-11, 2003 (CD-ROM published by and available from the International Ultraviolet Association, P.O. Box 1110, Ayr, ON, Canada N0B 1E0, http://www.iuva.org)

Bayha H: Die Ultraviolett-Entkeimung von Flüssigkeiten geringer Strahlen-durchlässigkeit (The ultraviolet disinfection of liquids with low radiation transmission). Zeitschrift für Hygiene 135 (1952), 1-26

Benesi E: Design of a centrifugal filmer for the ultraviolet irradiation of liquids. General Motors Engineering Journal 3 (1956), 2-8

Bering E, Meyer H: Methoden zur Messung der Wirksamkeit violetter and UV-Strahlenquellen (Methods for the measurement of the effectiveness of violet and ultraviolet radiation sources). Strahlentherapie 1 (1912), 189-207.

Bitton G, Henis Y, Lahav N: Effect of several clay minerals and humic acid on the survival of Klebsiella aerogenes exposed to ultraviolet irradiation. Applied Microbiology 23 (1972), 5: 870-874

Bolton J R: Ultraviolet principles and applications. EPA Newsletter 66 (1999), 9-36

Bolton J R, Linden K G: Standardization of methods for fluence (UV dose) determination in bench-scale UV experiments. Journal of Environmental Engineering 129 (2003), 3: 209-215

Brauer H-D, Schmidt R: A new reusable chemical actinometer for UV irradiation in the 248-334 nm range. Photochemistry and Photobiology 37 (1983), 5:587-591.

Brooks S C: The kinetics of inactivation of complement by light. Journal of General Physiology 3 (1920): 169-123

Brummelhuis H G J: Preparation of the prothrombin complex. In: Methods of plasma protein fractionation, edited by Curling J M, London: Academic Press, 1980, p. 117-128.

Bowen E J: The chemical aspects of light, 2$^{nd}$ revised edition, Oxford: Clarendon Press 1949

Cabaj A, Sommer R: Measurement of ultraviolet radiation with biological dosemeters. Radiation Protection and Dosimetry 91 (2000), 1-3: 139-142

Caillet-Fauquet, Di Giambattista M, Draps M-L, Sandras F, Branckaert T, de Launoit Y, Laub R: Continuous-flow UVC irradiation: a new, effective, protein activity-preserving system for inactivating bacteria and viruses, including erythrovirus B19. J. Virol. Meth. 118 (2004): 131-139

Calvert J G, Rechen H J L: Precision actinometry at low light intensities with malachite green leucocyanide. Journal of the American Chemical Society 74 (Apr. 20, 1952), 2101-2103.

Cortelyou J R, McWhinnie M A, Riddiford M S, Semrad J E: The effects of ultraviolet irradiation on large populations of certain water-borne bacteria in motion. II. Some physical factors affecting the effectiveness of germicidal ultraviolet irradiation. Applied Microbiology 2 (1954), 269-273

Dainton F S, Sills S A: Use of nitrous oxide to discriminate between various forms of hydrogen atoms existing in aqueous solutions of potassium iodide irradiated with ultraviolet light. Nature 186 (Jun. 11, 1960):879

Della Contrada J: Invention could revolutionize decontamination and purification of liquids. University at Buffalo Reporter 35 (27), Mar. 25, 2004, online edition: http://www-.buffalo.edu/reporter/vol35/vol35no27/articles/Patra-Pump.html, accessed May 10, 2004

Erdmann K: Versuche zur Aufhebung der koagulierenden Wirkungen von ultraviolettem Licht and von Röntgenstrahlen auf Euglobulin mit Strahlen-Schutzstoffen. Protoplasma 45 (1956). 3: 293-314

Favaro G. Actinometry: concepts and experiments. In: Drugs: Photochemistry and Photostability, Special Publications of the Royal Society of Chemistry 225 (1998), 295-304.

FDA (Food and Drug Administration, US Department of Health and Human Services): Kinetics of microbial inactivation for alternative food processing technologies. Washington, D.C. 2000. http://vm.cfsan.fda.gov/~comm/ift-uv.html Fisher G J, LeBlanc J C, Johns H E: A calorimetric determination of the quantum yield for the ionization of malachite green cyanide by ultraviolet radiation. Photochemistry and Photobiology 6 (1967), 757-767.

Forney L J, Pierson J A: Optimum photolysis in Taylor-Couette flow. American Institute of Chemical Engineers Journal 49 (2003) 3: 727-733

Gauglitz G. Modern chemical actinometry. EPA Newsletter (November 1983), 49-53

Gauglitz G, Hubig S: Azobenzene as a convenient actinometer: evaluation values for UV mercury lines and for the $N_2$ laser lines. Journal of Photochemistry 15 (1981), 255-257.

Gauglitz G, Hubig S: Chemical actinometry in the UV by azobenzene in concentrated solution: a convenient method. Journal of Photochemistry 30 (1985), 121-125.

Gauglitz G, Hubig S: Photokinetische Grundlagen moderner chemischer Aktinometer (Photokinetic bases of modern chemical actinometers). Zeitschrift für Physikalische Chemie, Neue Folge 139 (1984), 237-246.

Habel K, Sockrider B T: A continuous flow method of exposing antigens to ultraviolet radiation. Journal of Immunology 56 (1947), 273-279

Harrington W O, Hills C H: Reduction of the microbial population of apple cider by ultraviolet radiation. Food Technology 22 (1968), 117-120

Hiatt C W: Photodynamic inactivation of viruses. Transactions of the New York Academy of Science 23 (1960), 66-78

Kirk A D, Namasivayam C: Errors in ferrioxalate actinometry. Analytical Chemistry 55 (1983), 2428-2429.

Koutchma T, Keller S, Chirtel S, Parisi B: Ultraviolet disinfection of juice products in laminar and turbulent flow reactors. Innovative Food Science and Emerging Technologies 5 (2004), 2: 179-189

Koutchma T, Adhikari C: Effectiveness of the UV disinfection of juice. IUVA News 4 (2002), 5: 21-23.

Kuhn H J, Braslaysky S E, Schmidt R: Chemical actinometry. Pure & Applied Chemistry 61 (1989) 2:187-210.

Mack S D, Albrecht J J. Litchfield J H. Parker M E: Studies on the cold sterilization of liquid food using mercury radiation. II. Apple juice. Food Research 24 (1959), 383-391

Morowitz H J: Absorption effects in volume irradiation of microorganisms. Science 111 (1950), 229-230

Oppenheimer F, Benesi E, Taylor A R: The ultraviolet irradiation of biological fluids in thin-flowing films. American Journal of Public Health 49 (1959), 7: 903-923

Qualls R G, Johnson J D: Bioassay and dose measurement in UV disinfection. Applied and Environmental Microbiology 45 (1983) 3: 872-877

Rahn R O, Stefan M I, Bolton J R, Goren E, Shaw P-S, Lykke K R: Quantum yield of the iodide/iodate chemical actinometer: dependence on wavelength and concentration. Photochemistry and Photobiology 78 (2003), 2:146-152

Rahn R O, Xu P, Miller S L: Dosimetry of room-air germicidal (254 nm) radiation using spherical actinometry. Photochemistry and Photobiology 70 (1999), 3:314-318

Rahn R O: Potassium iodide as a chemical actinometer for 254 nm radiation: use of iodate as an electron scavenger. Photochemistry and Photobiology 66 (1997), 4:450-455

Rahn R O: Use of potassium iodide as a chemical actinometer. Photochemistry and Photobiology 58 (1993), 6:874-880

Rideal E K, Roberts R: The photochemistry of native proteins. Proceedings of the Royal Society A A205:391-408, 1951.

Sczechowskii J G, Koval C A, Noble R D: A Taylor vortex reactor for heterogeneous photocatalysis. Chemical Engineering Science 50 (1995) 20: 3163-3173

Schulz C R, Cervantes P, and Laplace C: Development of a flow-through actinometry monitor for dose measurements in UV disinfection reactors. Conference Prooceedings (on CD-ROM) of the International Ultraviolet Association's 1$^{st}$ International Congress on Ultraviolet Technologies, Washington D.C., Jun. 15-16, 2001.

Wang J, Mauser A, Chao S-F, Remington K, Treckmann R, Kaiser K, Pifat D, Hotta J: Virus inactivation and protein recovery in a novel ultraviolet-C reactor. Vox Sanguinis 86 (2004): 230-238

Wright H B and Sakamoto G: UV Dose required to achieve incremental log inactivation of bacteria, viruses, and protozoa. Trojan Technologies, London ON/Canada, 2001.

Zheleznova N V. Determination of the light flow intensity of uviol-type bactericidal lamps. Trudy Instituta hneni Pastera 52 (1979): 133-135

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All references cited herein, including all publications and all U.S. and foreign patents and patent applications, are specifically and entirely incorporated herein by reference. It is intended that the specification and Examples be considered exemplary only, with the true scope and spirit of the invention indicated by the following claims.

What is claimed is:

1. A method for determining an effective dose of monochromatic or polychromatic light from one or more light sources to inactivate microorganisms present in a non-transparent biological fluid comprising measuring the effect of the monochromatic or polychromatic light on a dosimetric solution matching the turbidity of the biological fluid at the photoinactivating wavelengths used, the turbidity and absorbance of the biological fluid, the turbidity and the viscosity of the biological fluid, the turbidity and the absorbance and the viscosity of the biological fluid, the absorbance of the biological fluid, or the viscosity and absorbance of the biological fluid, based on a light dose calibration by i) irradiating the dosimetric solution in a layer of an optical path-length sufficiently thin to absorb only a fraction of the incident light at a predetermined defined irradiance for a defined time to apply a defined fluence (light dose) resulting in a change of a measurable physical or chemical magnitude, and ii) by reading out the dose corresponding to the change in the magnitude measured during or after the light irradiation of the dosimetric solution in the light irradiation reactor, wherein step i) is executed before step ii) or vice versa, wherein the biological fluid is inactivated in a flow-through-reactor.

2. The method according to claim 1, wherein along the optical path length 50% or less of the incident irradiance is absorbed.

3. The method according to claim 1, wherein the biological fluid is inactivated in a flow-through-reactor and wherein the defined fluence can be modified by changing the defined irradiance and/or by changing the defined time determined by the flow rate of the biological fluid in the flow-through-reactor.

4. The method according to claim 1, further comprising determining the dose-distribution by titration of the number of viable microorganisms before and after, or before, during and after irradiating the biological fluid spiked before or during, or before and during the irradiation with the viable microorganisms.

5. The method according to claim 4, wherein the effective dose of light to inactivate microorganisms present in a biological fluid is a dose which inactivates at least about 99.9% of the viable microorganisms in the biological fluid.

6. The method according to claim 1, further comprising monitoring the intensity of the one or more light sources during the irradiation in order to determine an irradiating dose.

7. The method according to claim 1, wherein the light is in the UV range.

8. The method according to claim 1, wherein the dosimetric solution comprises an agent or a combination of agents selected from the group consisting of alkali metal iodide, alkaline earth metal iodide, ammonium iodide, aqueous uridine phosphate, alkali metal benzoate, alkaline earth metal benzoate, ammonium benzoate, alkali metal peroxodisulfate, alkaline earth metal peroxodisulfate, ammonium peroxodisulfate, tert-butanol, polyvinylpyrrolidone, bentonite, mica, montmorillonite, nontronite, hectorite, kaolinite, halloysite, dickite, a clay mineral, chalk, silica, fumed silica, baryte, gypsum, talcum, magnesia, alumina, bismuth oxychloride, zinc oxide, an alkaline earth sulphate, an alkaline earth carbonate, an alkaline earth phosphate, an alkaline earth hydroxyphosphate, an alkaline earth halogen phosphate, an insoluble silicate, an insoluble alumosilicate, an insoluble carbonate, an insoluble sulphate, an insoluble phosphate, an insoluble hydroxyl phosphate, a halogen phosphate, a perfluorinated hydrocarbon or a derivative thereof, a perfluorinated carboxylic acid or a salt thereof, and polyvinylpolypyrrolidone.

9. The method according to claim 1, wherein the dosimetric solution comprises a diluted potassium iodide-potassium iodate actinometer.

10. The method according to claim 1, wherein the dosimetric solution comprises a diluted potassium iodide-potassium iodate/polyvinylpyrrolidone actinometer.

11. The method according to claim 1, wherein the dosimetric solution comprises a diluted sodium benzoate actinometer.

12. The method according to claim 1, wherein the dosimetric solution comprises a diluted potassium peroxodisulfate/tert-butanol actinometer.

13. The method according to claim 1, wherein the dosimetric solution comprises a turbidity-causing agent.

14. The method according to claim 1, wherein the microorganisms are selected from the group consisting of species of the monera kingdom, spores of the species of the monera kingdom, species of the fungi kingdom, spores of the species of the fungi kingdom, prokaryotes, eukaryotes, and viruses.

15. The method according to claim 1, wherein the viruses are selected from the group consisting of Parvoviridae viruses, Minute Murine Virus, Canine Parvovirus, Bovine Parvovirus, Porcine Parvovirus, Feline Parvovirus, Circoviridae viruses, Circinoviridae viruses, Picornaviridae viruses, Hepatitis A Virus, and Encephalomyocarditis Virus, Anelloviridae viruses, Encephalomyocarditis Virus, Enteroviridae RNA viruses, Microviridae DNA bacteriophages, and Leviviridae RNA bacteriophages.

16. The method according to claim 1, wherein the method is performed in conjunction with at least one other sterilization or microorganism inactivation method.

17. The method according to claim 1, wherein the biological fluid comprises at least one additive to reduce damage and loss of biological activity of the fluid.

18. The method according to claim 1, wherein the method is performed with a solvent detergent treatment.

19. The method according to claim 1, wherein the biological fluid is a fluid selected from the group consisting of milk, whey, milk products, products derived from milk, fruit juices, products derived from fruit, vegetable juices, products derived from vegetable, native plant sap, transgenic plant sap, synthetic beverages, processed beverages, fermented beverages, alcoholic beverages, blood, plasma, plasma fractions, serum, fluids derived from blood, fluids derived from plasma, fluids derived from serum, fluids containing protein fractions, spinal fluid, cerebral fluid, lymph, saliva, semen, urine, prokaryotic cell culture supernatant, eukaryotic cell culture supernatant, prokaryotic cell lysate, eukaryotic cell lysate, a fluid intended for external therapeutical use, a fluid intended for enteral therapeutical use, a fluid intended for parenteral therapeutical use, a fluid intended for external cosmetic use, and a fluid intended for diagnostic use.

20. A method of controlling a light sum dose of monochromatic or polychromatic light emitted from one or more light sources to effectively inactivate microorganisms present in a biological fluid in a batch reactor, comprising the steps of:
a) determining an absorption-dependent irradiation source target light sum dose based on an effective dose of monochromatic or polychromatic light to inactivate microorganisms present in the biological fluid, an irradiation light dose rate and an irradiation time necessary to effectively inactivate the microorganisms in the batch reactor;
b) recording the irradiation light dose rate and the irradiation time during inactivation of the microorganisms present in the biological fluid in the batch reactor;
c) calculating the absorption-dependent irradiation source light sum dose based on the measurements in step b);
d) comparing the absorption-dependent irradiation source light sum dose determined in step c) with the absorption-dependent irradiation source target light sum dose determined in step a); and
e) discontinuing light exposure of the biological fluid once the absorption-dependent irradiation source light sum dose is equal to or greater than the absorption-dependent irradiation source target light sum dose.

21. The method of controlling the absorption-dependent irradiation source light sum dose according to claim 20, wherein the method is continued until the absorption-dependent irradiation source light sum dose is essentially equal to the absorption-dependent irradiation source target light sum dose despite irradiation light dose rate variations and/or intermediate switching off of at least one of the one or more light sources.

22. The method according to claim 20, wherein the effective dose is determined by measuring the effect of the monochromatic or polychromatic light on a dosimetric solution, comprising measuring the effect of the monochromatic or polychromatic light on a dosimetric solution matching the turbidity of the biological fluid at the photoinactivating wavelengths used, the turbidity and absorbance of the biological fluid, the turbidity and the viscosity of the biological fluid, the turbidity and the absorbance and the viscosity of the biological fluid, the absorbance of the biological fluid, or the absorbance and viscosity of the biological fluid, based on a light dose calibration by i) irradiating the dosimetric solution in a layer of an optical path-length sufficiently thin to absorb only a fraction of the incident light at a predetermined defined irradiance for a defined time to apply a defined fluence (light dose) resulting in a change of a measurable physical or chemical magnitude, and ii) by reading out the dose corresponding to the change in the magnitude measured during or after the light irradiation of the dosimetric solution in the light irradiation reactor, wherein step i) is executed before step ii) or vice versa.

23. The method according to claim 20, wherein the recording of the irradiation light dose rate and the irradiation time is carried out using at least one electronic radiometer, at least one chart recorder, and/or at least one sum counter.

24. The method according to claim 20, wherein the target light sum dose to inactivate microorganisms present in a biological fluid is a dose which inactivates at least about 99.9% of the viable microorganisms in the biological fluid.

* * * * *